US005855867A

United States Patent [19]
Katti et al.

[11] Patent Number: 5,855,867
[45] Date of Patent: Jan. 5, 1999

[54] HYDROXYMETHYL PHOSPHINE COMPOUNDS FOR USE AS DIAGNOSTIC AND THERAPEUTIC PHARMACEUTICALS AND METHOD OF MAKING SAME

[75] Inventors: Kattesh V. Katti; Srinivasa Rao Karra; Douglas E. Berning; C. Jeffrey Smith; Wynn A. Volkert; Alan R. Ketring, all of Columbia, Mo.

[73] Assignee: The Curators of the University of Missouri, Columbia, Mo.

[21] Appl. No.: 818,080

[22] Filed: Mar. 14, 1997

Related U.S. Application Data

[63] Continuation-in-part of Ser. No. 412,470, Mar. 29, 1995, abandoned.

[51] Int. Cl.$^6$ .............................. A61K 51/00; C07F 9/02; C07F 5/00; C07C 233/00
[52] U.S. Cl. ...................... 424/1.77; 424/1.49; 424/1.65; 424/1.69; 534/10; 534/14; 568/8; 568/10; 568/17; 556/18; 564/161
[58] Field of Search ................................. 424/1.49, 1.77, 424/1.69, 1.65, 9.34; 534/10, 11, 14, 15, 16; 556/18; 568/8, 10, 17; 564/161; 562/8

[56] References Cited

U.S. PATENT DOCUMENTS

| | | | |
|---|---|---|---|
| 4,439,196 | 3/1984 | Higuchi | 604/890 |
| 4,446,224 | 5/1984 | DeCant, Jr. et al. | 604/67 |
| 4,447,233 | 5/1984 | Mayfield | 604/152 |
| 4,475,196 | 10/1984 | La Zor | 371/29.1 |
| 4,486,194 | 12/1984 | Ferrara | 604/308 |
| 4,487,603 | 12/1984 | Harris | 604/152 |
| 4,795,626 | 1/1989 | Deutsch et al. | 424/1.65 |
| 4,959,217 | 9/1990 | Sanders et al. | 424/486 |
| 5,167,616 | 12/1992 | Haak et al. | 604/804 |
| 5,169,383 | 12/1992 | Gyory et al. | 604/798 |
| 5,225,182 | 7/1993 | Sharma | 424/85 |
| 5,635,158 | 6/1997 | Mazzi et al. | 424/1.69 |

OTHER PUBLICATIONS

Abrams et al., "Technetium–99m–human polyclonal IgG radiolabeled via the hydrazino nicotinamide . . . " *J Nucl Med* 31:2022–2028, (1990).

Abrams et al. "Synthesis and crystal and molecular structure of a technetium–hydralazino complex . . . " *Inorg Chim Acta* 173:133–135, (1990).

Chianelli et al. "99mTc–interleukin–2: a new radiopharmaceutical for the in vivo detection of lymphocytic infiltration" *J Nucl Biol Med* 38:476, (1994).

Deutsch, "Aspects of the chemistry of technetium phosphine complexes" *Radiochim Acta* 63:195–197, (1993).

Ellis et al., "Water–soluble tris (hydroxymethyl) phosphine complexes with nickel, palladim and platinum . . . " *Inorg Chem* 31:3026–3033, (1992).

Fritzberg et al., "Specific and stable labeling of antibodies with 99mTc with a dimide dithiolate chelating agent" *Proc. Natl. Acad. Sci., USA* 85:4025–4029, (1988).

Gustavson et al., "Synthesis of a new class of Tc–chelating agents . . . " *Tetrahedron Lett*, vol. 32, No. 40, pp. 5485–5488 (1991).

Jurisson et al., "Coordination compounds in nuclear medicine" *Chem Rev* 93:1137–1156, (1993).

Kelly et al., Technetium–99m–Tetrofosmin as a new radiopharmaceutical for myocardial perfusion imaging *J Nucl Med* 34:222–227 (1993).

Knight et al., "Thrombus imaging with 99mTc synthetic peptides based upon the binding domain of a monoclonal antibody . . ." *J Nucl Med* 35:282–288, (1994).

Lister–James et al., "A structure–activity–relationship (SAR) study of somatostatin receptor–binding peptides . . ." *J Nucl Med*, 35:257–258P, (1994).

Marmion et al., "Radiopharmaceutical development of TechneScan Q–12" *J Nucl Biol Med* 38:455–456, (1994).

Meares et al., "Chelate radiochemistry: cleavable linkers lead to altered levels of radioactivity in the liver" *Int J Cancer* 2:99–102, (1988).

Maina et al., "Synthesis, radiochemical and biological evaluation of 99mTc[N4(O)Phe]–octreotide . . ." *J Nucl Bio Med* 38:452, (1994).

Nock et al., "99mTc–N4–Lys–Biotin, a new biotin derivative useful for pretargeted avidin–biotin immunoscintigraphy. . ." *J Nucl Biol Med* 38:460, (1994).

Nowotnik and Nunn, "Technetium SPECT agents for imaging heart and brain" *DN and P* 5:174–183, (1992).

Parker, "Tumour targeting with radiolabeled macrocycle–antibody conjugates" *Chem. Soc. Rev.* 19:271–291, (1990).

Pasqualini et al., "Bis(dithiocarbamato)nitrido technetium–99m radid–pharmaceuticals: a class of neutral myocardial. . ." *J. Nucl. Med.* 35:334–340 (1994).

Rao et al., "Kinetics and mechanism of reactions of S–protected dithiol monoaminemonamide (MAMA) ligands with technetium" *Nucl Med Biol*, 19:889–895, (1992).

Troutner, "Chemical and physical properties of radionuclides" *Nucl Med Biol* 14:171 (1987).

Volkert et al., "Therapeutic radionuclides: production and decay property considerations" *J Nucl Med* 32:174–185, (1991).

Wilbur, "Radiohalogenation of proteins: an overview of radionuclides, labeling methods and reagents for conjugate labeling" *Bioconj Chem* 3:433–470, (1992).

Archer et al. (1995) in *Technetium and rhenium in chemistry and nuclear medicine*, editors Nicolini et al., Servizi Grafici Editoriali, Padova, 173.

Bandoli et al. (1984) An isothiocyanato complex of Technetium (II). Spectroelectrochemical and single–crystal x–ray.. *Inorg. Chem.*, 23:2898–2901.

(List continued on next page.)

Primary Examiner—Gary E. Hollinden
Assistant Examiner—Michael G. Hartley
Attorney, Agent, or Firm—Kohn & Associates

[57] ABSTRACT

A compound and method of making a compound for use as a diagnostic or therapeutic pharmaceutical comprises at least one functionalized hydroxyalkyl phosphine donor group and one or more sulfur or nitrogen donor and a metal combined with the ligand.

19 Claims, 9 Drawing Sheets

OTHER PUBLICATIONS

Beard et al., (1965) The preparation and properties of [Re(amine)$_4$O$_2$]+ type ions. *Inorg. Chem.*, 4:797–803.

Berning et al., (1996) In vitro and in vivo characterization of a 99mTc complex with tris(hydroxymethyl)phosphine (THP) *J. Nucl. Med. Biol.*, 23:617–622.

Betz et al., (1994) in *Basic Neurochem. Molecular Cell*, Raven Press Ltd., NY, 5th ed., pp. 681–699.

Blessing (1995) An empirical correction for absorption anisotropy *Acta Crystallogr.*, Sect. A, 51:33–38.

Brem et al. (1993) Polymers as controlled drug delivery devised for the treatment of malignant brain tumors. *Eur. J. Pharm. Biopharm.*, 39:2–7.

Clarke and Podbielski (1987) Medical diagnostic imaging with complexes of 99mTc. *Coord. Chem. Rev.*, 78:253–331.

DeRosch et al., (1992) Kit development for the Tc–99m myocardial imaging agent. *J. Nucl. Med.*, 33:850.

Greenwood and Earnshaw, (1993) in *Chemistry of the elements*, Pergamon Press, New York, Chapter 12, pp. 546–636.

Higley et al. (1993) Technetium–99m–1,2bis[bis(2–ethoxyethyl) phosphino]ethane: human biodistribution . . . *J. Nucl. Med.*, 34:30–38.

Hnatowich, (1990) Antibody radiolabeling, problems and promises. *Nucl. Med. Biol.*, 17:49–55.

Ichimura et al., (1984) Technetium electrochemistry. 2. Electro–chemical and spectroelectrochemical studies. . *Inorg. Chem.*, 23:1272–1278.

Jain et al., (1993) Biokinetics of technetium–99m–tetrofosmin: myocardial perfusion imaging agent. . *J. Nucl. Med.*, 34:1254–1259.

Jurisson et al., (1993) Coordination compounds in nuclear medicine. *Chem. Rev.*, 93:1137–1156.

Katti (1996) Recent advances in the chemistry of water–soluble phosphines–catalytic and biomedical aspects. *Current Science*, 70:219–225.

Katti et al., (1995) Coordination chemistry of phosphorus (III) and phosphorus(V) hydrazides. *Chem. Soc.Rev.*, 97–107.

Libson et al., (1983) Synthesis, characterization, and electro–chemical properties of tertiary diphosphine . . . *Inorg. Chem.*, 22(12), 1695–1704.

Marmion et al., (1995) in *Technetium and Rhenium in Chemistry and Nuclear Medicine–4*; Nicolini, M et al. eds; Servizi Grafici Editoriali, Padova, pp. 253–258.

Mayer and Kaska, (1994) Sterochemical control of transition metal complexes by polyphosphine ligands. *Chem. Rev.*, 94:1239–1272.

Maina et al. (1994) Synthesis, radiochemical and biological evaluation of 99mTc[N4 (O) Phe]–octreotide . . . *J. Nucl. Bio. Med.*, 38:452.

Orpen et al., (Harrison et al.) (1989) Water soluble, zero–valent, platinum–, palladium–, and nickel . . . *Chem. Soc. Chem. Commun.*, 1096–1097.

Pardridge (1992) Blood–brain barrier and new approaches to brain drug delivery. *West J. Med.*, 156(3) 281–286.

Pardridge (1992) Recent developments in peptide drug delivery to the brain. *Pharm. Toxicol.*, 71(1)3–10.

Pardridge [Bickel et al.](1993) Pharmacologic effects in vivo in brain by vector–mediated peptide drug delivery. *Proc. Natl. Acad. Sci. USA*, 90(7)2618–2622.

Reddy et al., (1996) Synthesis and characterization of dioxorhenium complexes derived from water–soluble diphosphine . . . *J. Chem. Soc., Dalton Trans.*, 4459–4462.

Reddy et al., (1996) Hydroxymethyl bis(phosphines) and their palladium (II) and platinum (II) complexes . . . *J. Chem. Soc., Dalton Trans.*, pp. 1301–1304.

Reddy et al., (1996) Chemistry in environmentally benign media. Synthesis and characterization of rhenium (V) . . . *Inorg. Chem.*, 35:1753–1757.

Reddy et al., (1995) Chemistry in environmentally benign media Part 1. Synthesis and characterization . . *Inorg. Chim. Acta.*, 240:367–370.

Refosco et al., (1993) Co–ordination of (o–aminophenyl) diphenyl–phosphine in complexes . . . *J. Chem. Soc. Dalton Trans.*, 605–618.

Sheldrick (1990) Phase annealing in SHELX–90: direct methods for larger structures. *Acta Cyrstallogr.*, A46:467.

Smith et al., (1996) New advances in the synthesis of water–soluble triphosphine and the development of tripodally . . . *J. Chem. Soc. Chem. Commun.*, 2557–2558.

Tisato et al., (1995) Syntheses and structural characterizations of six–coordinatoe Oxo–M(V) complexes . . . *Inorg. Chem.*, 34:1779–1787.

Vanderheyden et al., (1985) Comparison of the chemical and biological properties . . . *Inorg. Chem.*, 24:1666–1673.

Vanderheyden et al. (1984) Synthesis and characterization of cationic technetium complexes of 1,2–Bis(dimethylphosphino)ethane . . . *Inorg. Chem.*, 23:3184–3191.

SYNTHESIS OF Re-P₂S₂

SCHEME 1

$t_R = 6.34$ min
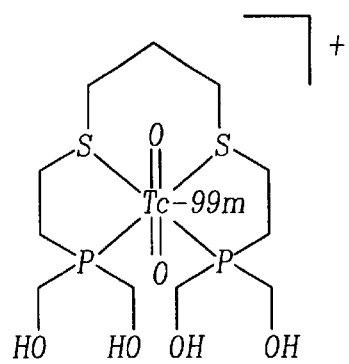
*Fig-16A*
$t_R = 6.35$ min
*Fig-16B*
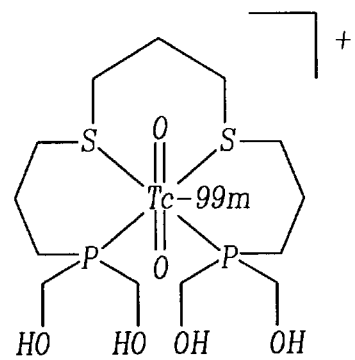

HYDROXYMETHYL PHOSPHINE COMPOUNDS FOR USE AS DIAGNOSTIC AND THERAPEUTIC PHARMACEUTICALS AND METHOD OF MAKING SAME

This is a continuation-in-part of application Ser. No. 08/412,470 filed on Mar. 29, 1995, now abandoned.

GRANT REFERENCE

The research carried out in connection with this invention was supported in part by a grant from the Department of Energy (DOE-DEFG0289ER60875). The Government has certain rights in the invention.

BACKGROUND OF THE INVENTION

1. Technical Field

The present invention relates to is pharmaceuticals and especially radiopharmaceuticals for use as diagnostic and therapeutic agents. More specifically, the present invention relates to compounds and methods of synthesizing compounds which utilize multi-dentate ligands which form stable complexes with metal compounds both with and without the need of external reducing agents for use as diagnostic or therapeutic radiopharmaceuticals.

2. Background Art

Because of the favorable physical properties, widespread availability, and low cost of $^{99m}$Tc, this radionuclide continues to be the most attractive candidate to formulate diagnostic radiopharmaceuticals for scintigraphic imaging studies in patients (Jurisson et al., 1993). Re, a chemical analogue of Tc, has two radioisotopes (i.e., $^{186}$Re and $^{188}$Re; $^{186/188}$Re) that have physical and production properties that make them among the most attractive beta-emitting radionuclides for formulation of new therapeutic radiopharmaceuticals (Volkert et al., 1991; Troutner, 1987). Since the chemical properties of Tc and Re are often identical (although, not always) many ligand systems can be used as a basis to synthesize bifunctional chelating agents (BFCAs) that are capable of forming chelates with $^{99m}$Tc that have the same structural and physicochemical properties as the corresponding $^{186/188}$Re chelates.

Development of sophisticated molecular probes in the design of new $^{99m}$Tc- and $^{186/188}$Re radiopharmaceuticals will provide for future advances in the diagnosis and treatment of patients. While many important single photon emission computed tomography (SPECT) radiopharmaceuticals are effectively used as specific tools for diagnosis of human disease, accelerated development of many new site-directed synthetic derivatives (e.g., immunologically derived molecules, receptor-avid molecules, etc.) will provide a multitude of opportunities for further technological advances for both diagnostic and therapeutic applications.

When developing effective site specific therapeutic or diagnostic radiopharmaceuticals, many important factors must be considered. It is essential that the metallic radionuclide (e.g. Re-188 or Tc-99m), upon interaction with a bifunctional chelating agent, should form an in vivo stable complex in high specific activities with 1:1 metal to ligand stoichiometry. These stringent requirements restrict the choice to only a few ligand backbones and, therefore, necessitates the design and development of new bifunctional chelating agents. Most importantly, a detailed understanding of the coordination chemistry of new ligand systems with non radioactive rhenium is important for the subsequent extention of these reactions at the tracer levels to label bifunctional chelating agents using Re-188.

Many difficulties encountered in the design of highly selective radiolabeled drug carriers must be overcome (e.g., problems in efficient drug delivery to target sites, in vivo metabolism, rates of clearance of radioactivity from non-target tissues relative to target tissues, etc.). The physicochemical characteristics of the $^{99m}$Tc- and $^{186/188}$Re-chelate moiety attached or fused to the site-directed molecule will play a crucial role as an inherent determinant of the effectiveness of the final drug product. In addition, the ability of $^{99m}$Tc or $^{186/188}$Re to label the final product under conditions amenable for routine formulation of radiopharmaceuticals is also an essential consideration.

Labeling of biomolecules with $^{99m}$Tc or $^{186/188}$Re to produce effective radiopharmaceuticals presents many challenges. It is necessary to produce $^{99m}$Tc and/or $^{186/188}$Re labeled drugs that have high in vitro and in vivo stabilities. Several different ligand frameworks have been developed that form $^{99m}$Tc or Re chelates exhibiting minimal or no measurable in vivo or in vitro dissociation. These chelates have provided radiopharmaceutical chemists with a selection of $^{99m}$Tc-chelates that have a range of physicochemical characteristics.

The formation of $^{99m}$Tc (viz Re) products in high yields with high radiochemical purity (RCP), however, usually requires the presence of large quantities of excess ligand during the formulation processes that are used for routine pharmaceutical preparation. Unfortunately, the high specific activities (i.e., GBq/$\mu$mole or Ci/$\mu$mole) required for radiolabeled site-directed synthetic derivatives being developed preclude the use of many of these chelation systems, thus, severely limiting the choice to only a few ligand backbones.

High specific activity (Sp. Act) radiolabeled agents can be prepared using either preformed $^{99m}$Tc- or $^{186/188}$Re bifunctional chelates (BFCs) or post-conjugation chelation with the radioactive metals where a chelating moiety is already appended (Parker, 1990) or fused (Lister-James et al., 1994; Knight et al., 1994) to the biomolecular targeting agent. Even though maximization of Sp. Act can be achieved by separation of the radiolabeled from the non-radiolabeled molecules, practically, it is more desirable to employ chelation systems that require small quantities of the chelates. In the formation of products that will be ultimately used as FDA approved $^{99m}$Tc/$^{186/188}$Re radiopharmaceuticals for routine patient care applications, it is most desirable to keep the number of steps for the formation of the drug-product to a minimum, ideally to one step, as is the case for most $^{99m}$Tc- "instant kits".

One of the few ligand systems shown to be effective for preparation of high yield, stable $^{99m}$Tc chelates using small quantities of chelator are the amido-thiol class of ligands (Fritzberg et al. 1988, Rao et al., 1992, and Chianelli et al, 1994). Generally, these types of multi-dentate ligands contain at least four donor atoms and one or two thiol donor groups in combination with two to three amido donor groups. Several $N_2S_2$ or $N_3S$ amido-thiol frameworks have been used to synthesize BFCAs and include diamidodithiol (DADS) ligands (Fritzberg et al., 1988), monoaminemonoamide (MAMA) ligands (Rao et al., 1992; Gustavson et al., 1991) and mercaptoacetylglycylglycylglycine (MAG$_3$) ligands (Chianelli et al., 1994). While the amido-thiol ligands make effective BFCAs for $^{99m}$Tc and $^{186/188}$Re, the range of their physicochemical properties are limited, conditions for routine labeling can be difficult to reduce to practical utility and external reducing agents (e.g., Sn(II) are usually present during labeling with $^{99m}$Tc or $^{186/188}$Re which can cause irreversible alteration of the site-directed moiety reducing or eliminating specific in vivo localization.

Other ligand systems that have also been used for $^{99m}$Tc labeling include $N_2S_2$-amine-thiol ligands, propylineaminoxime (PnAO) derivatives and the hydrazino nicotinamide (HYNIC) system. The former two derivatives form neutral lipophilic $^{99m}$Tc-chelates, that while beneficial in some respects, result in high non-specific binding in vivo and poor clearance from non-target tissues (Muna et al., 1994; Noch et al., 1994). The HYNIC system does not form a well-defined product with $^{99m}$Tc (Abrams et al., 1990a; Abrams et al., 1990b). All of these systems usually form chelates with $^{99m}$Tc with the necessity of external reducing agents.

Ligand backbones containing trivalent phosphine donor groups have been shown to be effective in forming stable $^{99m}$Tc and $^{186/188}$Re chelates in high RCP. Phosphines not only chelate $^{99m}$Tc (or Re), but they are capable of reducing both pertechnetate and perrhenate to lower oxidation states, and, therefore, do not necessarily require the presence of an external reducing agent (e.g., Sn(II)).

Diphosphine ligands have been extensively used in the development of $^{99m}$Tc-radiopharmaceuticals, particularly those that are used as $^{99m}$Tc-labeled myocardial perfusion agents (Deutsch, 1993; Nowotnik and Nunn, 1992; Kelly et al., 1993). Unfortunately, most of these chelates utilize alkylphosphine donor groups and the phosphines are rapidly oxidized (to phosphorus oxides) in aqueous solutions containing $O_2$ and require stringent conditions for manufacture of the drugs and for ultimate routine formation of the final product. For these reasons, ligands that contain alkyl phosphine donor groups have limited flexibility for the design of new drugs and do not form a rational basis to prepare most phosphine-based BFCAs for use in preparing site-directed radiopharmaceuticals.

Aromatic phosphines have also been reported for use with Tc and Re, however, the high lipophilicity of the resulting chelates minimize their potential utilization as BFCAs for in vivo applications.

A small ligand system containing phosphine donor groups with good solubility in aqueous solutions and not oxidized by $O_2$, but still capable of reducing $^{99m}$TcO$_4^-$ or $^{186/188}$ReO$_4^-$ and/or strongly chelating reduced Tc or Re, would find widespread applicability in formulating new radiopharmaceuticals or new BFCAs.

Bonding capabilities of phosphines with the early transition metals (e.g.; Technetium or Rhenium) are influenced not only by the σ phosphorus-metal interaction which uses the lone pair of electrons on the P$^{III}$ center and a vacant orbital on the metal center, but also by the distinct possibility of synergic π back-donation from a non-bonding dπ pair of electrons on the metal center into the vacant 3dπ orbital on the phosphorus. The σ and π bonds reinforce one another to produce strong phosphorus-metal bonds which are often stable even under in vivo conditions. (Greenwood and Earnshaw, 1993, Mayer and Kaska, 1994). Therefore, functionalized phosphines constitute an important family of ligands for use in nuclear medicine. For example, the Tc-99m based radiopharmaceuticals, Tetrafosmin and Technecard, which are currently being used as in vivo heart imaging agents, are derived from bis chelating and monochelating phosphines of the type (EtO(CH$_2$)$_2$)$_2$P(CH$_2$)$_2$P((CH$_2$)$_2$OEt) and P(CH$_2$CH$_2$OCH$_3$)$_3$, respectively. (Higley et al., 1993, Jain et al., 1993, DeRosch et al., 1992, Marmion et al., 1995). While bis chelating phosphines of the DMPE class (where DMPE stands for 1,2-bis(dimethylphosphino) ethane) are able to produce in vivo stable Tc-99m complexes (Deutsch et al., 1981, Deutsch, 1993, Glavon et al., 1982, Vanderheyden et al., 1984, Vanderhyden et al., 1985), the inherent oxidative instability of DMPE and related alkyl phosphines limits their utility in terms of ligand backbone modifications to produce bifunctional chelating agents (BFCAs) in the development of Tc-99m (or Re186/188) labeled biomolecules. On the other hand, aryl phosphines are usually too large or highly charged (e.g. sulfonated aryl phosphines) and, therefore, may be unsuitable in the design of BFCAs for use in nuclear medicinal applications (Cornils and Wiebus, 1995). Studies by Deutsch et al., applicant, and several others have demonstrated that technetium (or rhenium) forms in vivo stable and kinetically inert bonds with phosphines. (DeRosch et al., 1992, Bandoli et al., 1984, Vanderheyden et al., 1985, Vanderheyden et al., 1984, Libson et al, 1983, Ichimura et al., 1984). Therefore, new developments in the design of phosphine ligands may aid in the discovery of new, performance effective, radiopharmaceuticals. In particular, the synthesis of functionalized phosphine frameworks that would result in the formation of Tc-99m or Re-188 complexes with 1:1 metal to ligand stoichiometrics becomes important in the context of design and development of radiopharmaceuticals produced via the labelling of specific biomolecules (e.g. peptides or proteins), for use in tumor specific diagnosis or therapy of human metastases. In this approach of designing diagnostic or therapeutic radiopharmaceuticals, it is important that the bifunctional chelating agent (ligand) be bound to a point of the biomolecule away from the active site (e.g. amino acid sequence necessary for receptor binding). Radiolabelling of the biomolecule/ligand complex with Tc-99m or Re-188 can then be carried out via strong covalent interactions of the metal center with specific donor atoms of the ligand, with no destruction of receptor specificity as is shown in FIG. 1. Simple aryl or alkyl functionalized phosphines (e.g. PPh$_3$ or $(H_3C)_2PCH_2CH_2P(CH_3)_2$) produce strong and in vivo stable metal-phosphorus bonds. However, they are unsuited for use in the design of biomolecular labelled radiopharmaceuticals because, most often, the coordination chemistry of these ligands produces complexes with more than one ligand per metal center. The chemical modifications of $(H_3C)_2PCH_2CH_2P(CH_3)_2$ (DMPE) and other related alkyl phosphates present difficulties in forming complexes with one ligand per metal center. Furthermore, their oxidative instability and pyrophoric nature limit their use in the development of bifunctional chelating agents via ligand modification reactions. Several groups have investigated the coordination chemistry of technetium and rhenium with sulfur/nitrogen and phosphine containing ligands (Archer et al., 1995, Refosco et al., 1993, Tisato et al., 1995). However, the presence of bulky aryl substituents on the phosphines often limit their degree of solubility in aqueous solutions making them unsuitable for bifunctional chelating agents.

Most other bifunctional chelation systems require the presence of an external reducing agent (e.g., Sn$^{+2}$) or prereduction of $^{99m}$TcO$_4^-$ or $^{186/188}$ReO$_4^-$ to lower metal oxidation states (e.g. $^{99m}$Tc-glucoheptonate). Water soluble phosphine groups containing low molecular side arms attached to each phosphine P-atom would provide versatility in ligand design and could be used as both as a reducing agent for $^{99m}$TcO$_4^-$ (or $^{186/188}$ReO$_4^-$), under conditions used for routine $^{99m}$Tc-radiopharmaceutical preparation, and as an efficient complexing agent for the reduced forms of Tc or Re.

Applicants use a series of multi-dentate ligands containing functionalized hydroxyalkyl phosphines that are stable in aerated aqueous solutions and will form highly stable $^{99m}$Tc and $^{188}$Re chelates. Unlike prior art alkyl phosphine based ligands designed to reduce or chelate $^{99m}$Tc or $^{186/}$ 188Re, the hydroxyalkyl phosphine groups are not sensitive to the presence of oxygen when dissolved in aqueous solutions. Other water soluble phosphine ligands with good oxidative stability have also been used as reducing agents, however, the side chains attached to the phosphine donor P-atoms in these ligands are bulky and/or produce highly charged phosphines which limit their utility in radiopharmaceutical development (Pasqualine et al., 1994).

Most other bifunctional chelation systems require the presence of an external reducing agent (such as Sn(II) or NaBH$_4$) or prereduction in order to reduce the $^{99m}$TcO$_4^-$ (or $^{186/188}$ReO$_4^-$) from the +7 oxidation state to lower oxidation states (e.g., $^{99m}$Tc-GH) that are more readily chelated.

The ligands containing one or more hydroxyalkyl phosphine donor groups of the present invention require no external reducing agents, however, the ligand can be used as coordinating groups when used in conjunction with other reducing agents or $^{99m}$Tc-synthons. The resulting $^{99m}$Tc and Re complexes produced with these phosphine containing ligands exhibit excellent in vivo stability as well in aqueous solutions including human serum.

SUMMARY OF THE INVENTION AND ADVANTAGES

According to the present invention, there is provided a compound for use as diagnostic or therapeutic pharmaceuticals, the compound including a ligand and a metal combined with the ligand, the ligand comprising at least one hydroxyalkyl phosphine donor group and one or more sulfur or nitrogen donors and is capable of reducing the metal and thereby promoting formation of the compound.

The present invention further provides a method of making multi-dentate compounds for use as diagnostic and/or therapeutic pharmaceuticals including the following reactions:

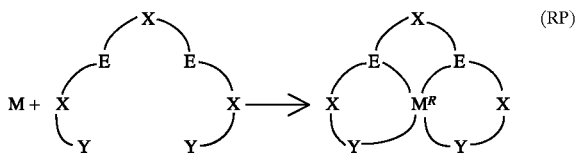
(RP)

wherein, M is a transition metal, M$^R$ is a transition metal in a reduced state; X is (CHR)$_n$ where (n=0, 1, 2, or 3) and R is hydrogen, carboxyl, or aromatic; E is N,

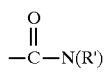

where R' is hydrogen or methyl, or S; and Y is a hydroxyalkyl phosphine of the formula P(A—OH)$_n$ where (n=1, 2, or 3) and where A is —CH$_2$, —C$_2$H$_4$, or iso- or normal —C$_3$H$_6$—.

The present invention further provides a method for radiological imaging including the steps of administering an effective amount of a compound of the formula:

(RP)

wherein, M is a transition metal, M$^R$ is a transition metal in a reduced state; X is (CHR), where (n=0, 1, 2, or 3) and R is hydrogen, carboxyl, or aromatic; E is N,

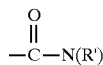

where R' is hydrogen or methyl, or S; and Y is a hydroxyalkyl phosphine of the formula P(A—OH)$_n$ where (n=1, 2, or 3) and where A is —CH$_2$, —C$_2$H$_4$, or iso- or normal— C$_3$H$_6$— and detecting for presence of the compound.

The present invention also provides a multi-dentate ligand for use in constructing therapeutic and diagnostic radiopharmaceuticals having the structure:

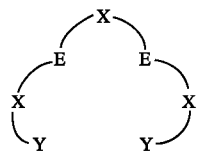

wherein X is (CHR)$_n$ where (n=0, 1, 2, or 3) and R is hydrogen, carboxyl, or aromatic; E is N,

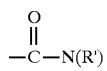

where R' is hydrogen or methyl, or S; and Y is a hydroxyalkyl phosphine of the formula P(A—OH)$_n$ where (n=1, 2, or 3) and where A is —CH$_2$, —C$_2$H$_4$, or iso- or normal- C$_3$H$_6$—.

The present invention also provides a method for separating uncoordinated hydroxyalkyl phosphine groups from hydroxyalkyl phosphine groups coordinated with metal atoms including the steps of reacting uncoordinated hydroxyalkyl phosphine groups with an amine to remove the uncoordinated groups thereby yielding substantially pure compounds.

BRIEF DESCRIPTION OF THE DRAWINGS

Other advantages of the present invention will be readily appreciated as the same becomes better understood by reference to the following detailed description when considered in connection with the accompanying drawings wherein:

FIGS. 16a–b are graphs which represent HPLC chromatograms of $P_2S_2$ complexes (a) $^{99m}$Tc-11 and (b) $^{99m}$Tc-12; and FIGS. 17a–b are graphs which represent HPLC chromatograms of

DETAILED DESCRIPTION OF THE PREFERRED EMBODIMENT

Figure 1:
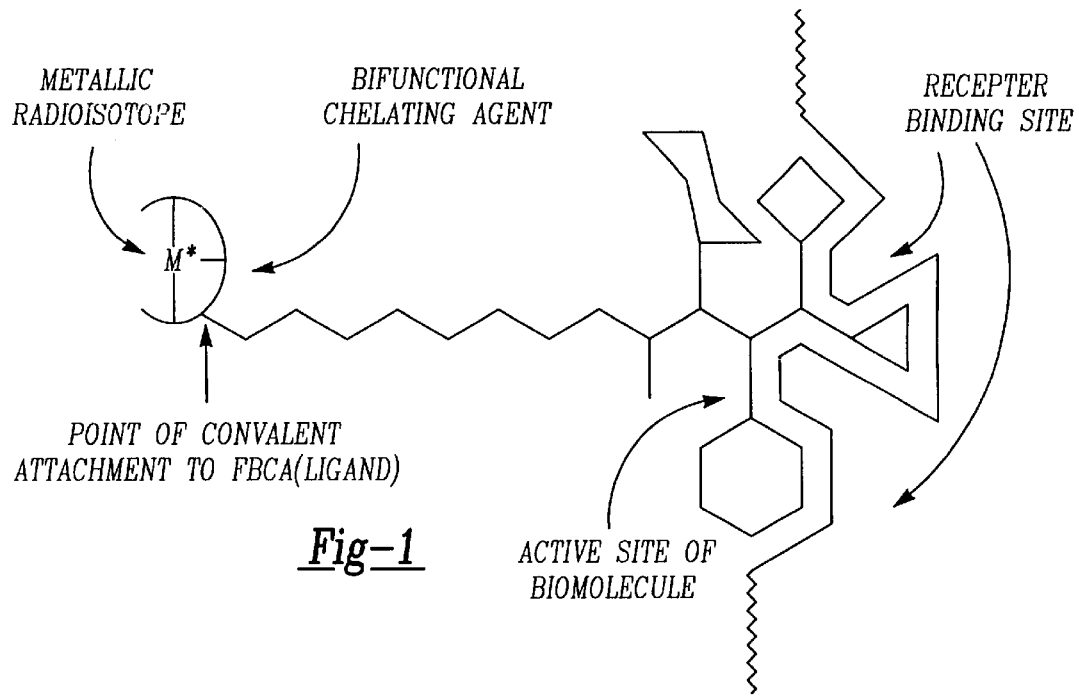
FIG. 1 is a diagram of a representative model of radiolabelling bioactive molecules.

Generally, the present invention provides compounds for use as a diagnostic or therapeutic pharmaceutical. The compounds can also be used for other pharmaceutical applications including MRI contrast agents. The novel compounds of the present invention provide labeled molecules which can be used as diagnostic and therapeutic radiopharmaceuticals.

The compounds include a transition metal complexed with at least one ligand including coordination of the metal to one or more hydroxyalkyl phosphine (HMP) donor groups. A phosphine-based ligand system is provided which typically contains between one and six hydroxyalkyl phosphine donor units for use in forming complexes with a variety of transition metals that have high in vitro and/or in vivo stability. The invention provides a hydroxyalkyl phosphine-based ligand system for use in forming complexes with a variety of transition metals that have high in vivo and/or in vitro stability in aerated aqueous solutions.

The compounds and method of producing the compounds of the present invention can be generally characterized by the formulas:

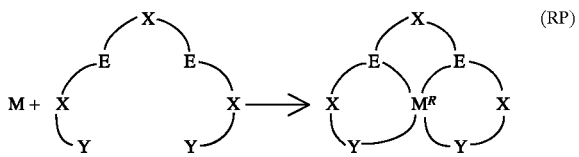

wherein, M is a transition metal, $M^R$ is a transition metal in a reduced state; X is $(CHR)_n$ where (n=0, 1, 2, or 3) and R is hydrogen, carboxyl, or aromatic; E is N,

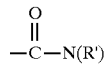

where R' is hydrogen or methyl, or S; and Y is a hydroxyalkyl phosphine of the formula $P(A-OH)_n$ where (n=1, 2, or 3) and where A is $-CH_2$, $-C_2H_4$, or iso- or normal-$C_3H_6$. In a preferred embodiment of the present invention, A is methyl.

The ligand is complexed with the transition metal, generally from the group including $^{186/188}$Re, $^{105}$Rh, and $^{99m}$Tc. These complexes contain greater than or equal to ($\geq$) 1:1 ligand-to-metal ratios which is formed making the resulting chelates small and well-defined. These specific combinations permit the formation of the complexes in a one step, high yield reaction as described below, especially for use with readily available chemical forms of the radionuclides.

For example, $^{99m}$TcO$_4^-$, ReO$_4^-$ chelates or $^{105}$Rh-chloride can be used. It has been determined that these types of hydroxyalkyl phosphine ligands form highly stable chelates with a variety of transition metals that have radioactive isotopes which include $\gamma$ and $\beta$ emitting isotopes such as $^{186}$Re, $^{188}$Re, $^{109}$Pd, $^{105}$Rh, etc., or for diagnostic use such as with $^{99m}$Tc radiopharmaceuticals.

More specifically, the present invention provides methods to formulate multi-dentate $^{99m}$Tc- or $^{186/188}$Re-labeled molecules (chelates) for use as diagnostic or therapeutic radiopharmaceuticals, respectively. The ligands used in this technology include one or more hydroxyalkyl phosphine donor groups that can be used in reducing $^{99m}$Tc- or $^{186/188}$Re and/or coordinating $^{99m}$Tc, $^{186/188}$Re, or $^{105}$Rh. The hydroxyalkyl phosphine group(s) on the ligand are soluble in aqueous solutions and exhibit minimal or no significant oxidation by $O_2$. That is, the invention provides small air stable and water soluble phosphine based ligands for use in forming complexes with $^{99m}$Tc- or $^{186/188}$Re in high yields that have high in vitro and in vivo stability which are not sensitive to oxidation in the presence of $O_2$. $^{99m}$Tc or $^{186/188}$Re reactants can be in the form of oxides (including $^{99m}$TcO$_4^-$ or $^{186/188}$ReO$_4^-$) as well as in other forms of the metals.

The chelates made in accordance with the present invention have been found to be stable in aqueous solutions, serum and other body fluids. This is critical in order to solve the problems of prior art agents which did not form stable chelates thereby having an inherent loss of control of localization of the radionuclide paramagnetic metal. Further, compounds made in accordance with the present invention can be chemically modified, as discussed below, to provide for specificity of localization, increased physical half-life of the radionuclide, improved pharmacokinetics, and increased selectivity of target tissues, such as tumors, over normal tissue, such as bone marrow, kidney, G.I. tract, liver etc.

The compounds made in accordance with the present invention are not only stable in neutral aqueous solutions, but have also been found to be stable in acidic and basic aqueous media. Again, this is critical with regard to localization of the compound in areas of the body having different pH's, as well as being stable through different administration routes, such as oral administration.

The ligands produced in accordance with the present invention are multi-dentate (more than one donor atom per ligand molecule).

The general types of hydroxyalkyl phosphine containing ligands include bidentate-bishydroxyalkyl phosphine ligands, and multi-dentate (i.e., number of chelating atoms or group $\geq$3) containing $\geq$1 hydroxyalkyl phosphine groups per metal. These ligands are used to form the stable, water soluble $^{99m}$Tc, $^{186/188}$Re, and $^{105}$Rh chelates of the present invention.

In addition to the use of hydroxymethyl phosphine ligands by themselves to form $^{99m}$Tc chelates for radiopharmaceutical preparations, hydroxyalkyl phosphine ligands can also be used in conjunction with other ligands used to chelate $^{99m}$Tc, $^{186/188}$Re, and $^{105}$Rh.

For example, the mono-dentate phosphine ligand tris (3-methoxy-1-propyl) phosphine was used in conjunction with 1,2-bis (dihydro-2,2,5,5-tetramethyl-3-furanone-4-methyleneamino) ethane to complex $^{99m}$Tc to form a ($^{99m}$Tc-Q12) lipophilic-cationic (+1) complex. This complex is being evaluated for use as a myocardial perfusion radiopharmaceutical (Marmion et al., 1994). In this complex, the mono-dentate phosphine ligand is bound in the trans positions to the metal (Deutsch, 1993; Marmion et al., 1994). The ether side chains on this phosphine ligand increase the lipophilicity of the $^{99m}$Tc chelate in order to improve myocardial uptake. The hydroxyalkyl phosphine ligands described in the present invention can be used in a similar manner. In contrast to the prior art monodentate phosphine ligands, the hydroxyalkyl phosphine ligand increases aqueous solubility of the complex for improved clearance into the urine via the kidneys.

Bi-dentate hydroxyalkyl phosphine ligands used produced in accordance with the present invention are characterized by the following formula:

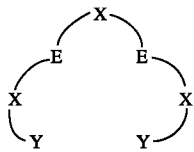

wherein X is $(CHR)_n$ where (n=0, 1, 2, or 3) and R is hydrogen, carboxyl, or aromatic; E is N,

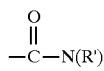

where R' is hydrogen or methyl, or S; and Y is a hydroxyalkyl phosphine of the formula $P(A-OH)_n$ where (n=1, 2, or 3) and where A is $-CH_2-$, $-C_2H_4-$, or iso- or normal-$C_3H_6-$.

The functionalities on X and/or E can be used to change the chemical characteristics (e.g., polarity, charge, etc.) of the final $^{99m}$Tc- or $^{186/188}$Re-chelate or for linking the chelate to a bio-selective targeting moiety (e.g., MAb, receptor agent), and R can be selected from the group consisting of H, an alkyl group ($C_1$–$C_4$), an aromatic group, and/or contain a functional group such as —OH, —NH$_2$, —COOH, —SH, and other groups used for conjugation of uncomplexed ligand or "preformed" $^{99m}$Tc or $^{186/188}$Re complex of the BFCA to the biomolecular targeting structure.

Methods used for conjugation of chelates to biomolecules, such as peptides, proteins, and antibodies, can involve the activation (e.g., to activated esters, N-hydroxysuccinimides, benzyl isothiocyanate, alkyl halides, cylohexyldiimide, etc.) of functional groups that have been previously described (Meares et al., 1988; Parker, 1990; Wilbur, 1992).

Formation of $^{99m}$Tc (and $^{186/188}$ReO$_4^-$) can be performed by reduction of $^{99m}$TcO$_4^-$ by excess of the phosphine ligand, an external reducing agent, e.g., Sn(II) or by transchelation.

In an embodiment of the present invention, multi-dentate hydroxyalkyl phosphine based ligands can be used to form $^{99m}$Tc or $^{186/188}$Re complexes in aqueous systems by transchelation from weaker donor chelates (e.g., $^{99m}$Tc(V)-glucoheptonate, $^{186/188}$Re(V)-citrate, $^{99m}$Tc-P(CH$_2$OH)$_3$), following reduction with external reducing agents (e.g., Sn$^{+2}$), or without external reducing agents. This approach utilizes ligand frameworks containing greater than or equal to ($\geq$) one (1) hydroxyalkyl phosphine donor group(s).

In one such embodiment, a hydroxyalkyl phosphine donor group on a multi-dentate ligand backbone is utilized so that the phosphine functionality of the molecule reduces $^{99m}$TcO$_4^-$ or $^{186/188}$ReO$_4^-$ and the other intramolecular phosphines or other donor atoms (e.g., —N, —O, —P or —S atoms) interact to form stable chelates with the reduced radiometals.

Most of the hydroxyalkyl phosphine containing ligands used to form BFCAs are multi-dentate (i.e., $\geq$3 donor atoms) and, generally, form 1:1 ligand-to-metal complexes with the reduced (i.e., oxidation states <+7) $^{99m}$Tc, $^{186/188}$Re, and $^{105}$Rh.

Hydroxyalkyl phosphine ligands with lower denticity can form $^{99m}$Tc or $^{186/188}$Re chelates with metal-to-ligand ratios greater than (>) 1:1 which also can be utilized in the formation of radiopharmaceuticals.

Generally, multi-dentate phosphine-based ligands are a preferred embodiment of the present invention since they are capable of forming 1:1 metal-to-ligand ratio complexes with $^{99m}$Tc or $^{186/188}$Re. The ability to form 1:1 ratio metal-to-ligand complexes permits formation of $^{99m}$Tc or $^{186/188}$Re chelates that form an essential component of well-defined diagnostic or therapeutic radiopharmaceuticals.

The hydroxyalkyl phosphine based ligands are advantageous since they permit labeling of compounds with $^{99m}$Tc or $^{186/188}$Re in aerated aqueous media in the neutral pH range. In addition, the hydroxyalkyl phosphine based ligands promote the formation of highly stable chelates by simply mixing $^{99m}$TcO$_4^-$ or $^{186/188}$ReO$_4^-$ with the ligand. This is advantageous since radiopharmaceuticals generally are prepared just prior to their administration in order to provide maximum isotope activity. This can occur over a wide pH range, in the presence of O$_2$, and in the absence of external reducing agents (e.g., Sn$^{+2}$). These properties make hydroxyalkyl phosphine based ligands particularly useful and versatile for the formulation of new and unique $^{99m}$Tc or $^{186/188}$Re commercial drug products for routine use in human patients.

Figure 4:
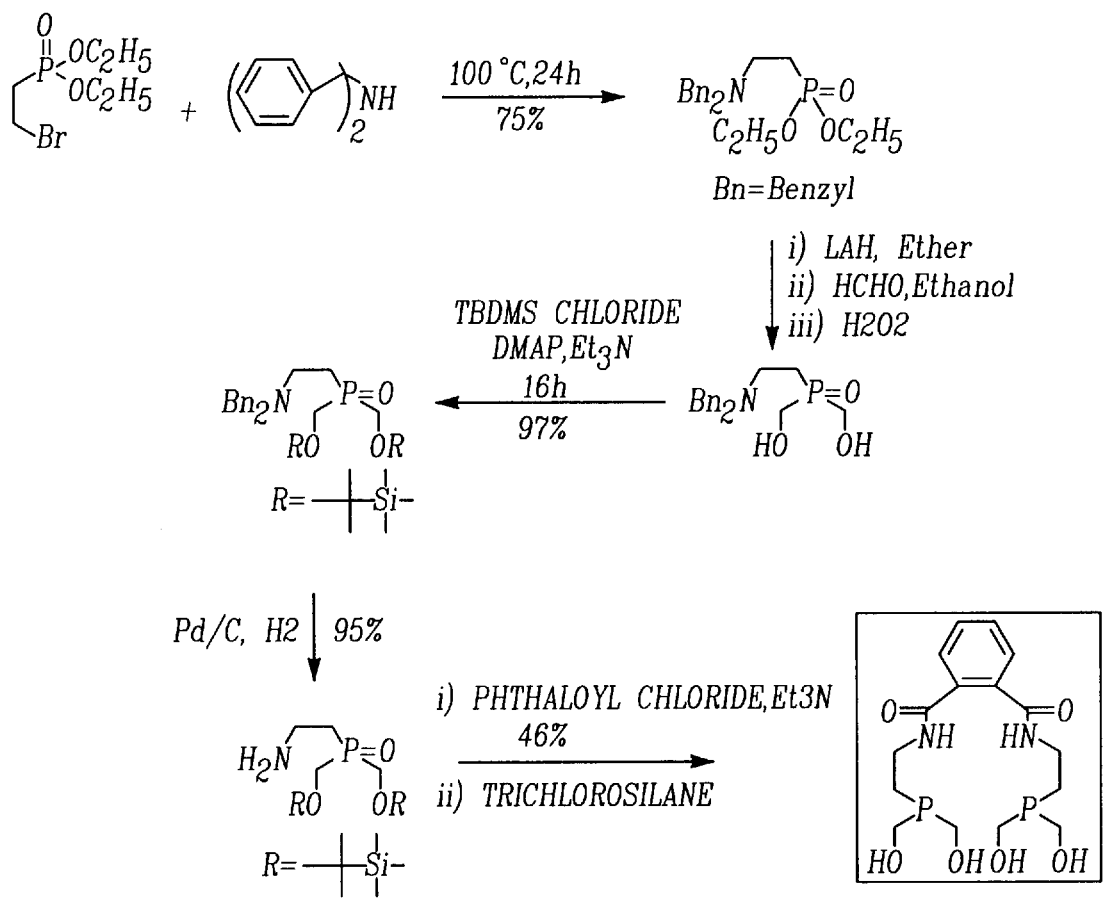
FIG. 4 illustrates a synthesis scheme for the synthesis of a diamido diphosphine of the general formula P$_2$N$_2$ in accordance with the present invention (compound 4) and also illustrates a synthesis strategy used for the reduction of phosphorus oxide (or sulfide) to the corresponding phosphine to produce P$_2$N$_2$ multi-dentate phosphines in accordance with the present invention.

Referring to FIG. 4, a synthesis scheme for synthesizing ligands according to the present invention is shown.

Multi-dentate ligands used in accordance with the present invention can be characterized by wide variety of formulae. One class of ligands includes ligand frameworks in which only phosphine groups are used as donor sets to coordinate $^{99m}$Tc or $^{186/188}$Re. The other class utilizes ligand backbones containing the hydroxyalkyl phosphine group(s) along with other donor atoms (e.g., S, N, P, or O) or groups (e.g., amines, amides, thiols, carboxyls or hydroxyls) are used to coordinate the metals.

The chelating groups can include two donor atoms which are hydroxymethyl phosphine P-atoms and two donor atoms which are atoms other than P-atoms and have the formula:

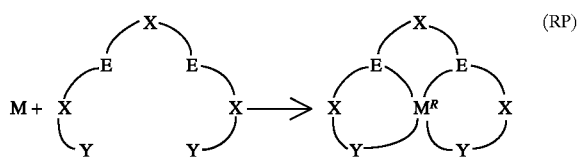

wherein, M is a transition metal, $M^R$ is a transition metal in a reduced state; X is $(CHR)_n$ where (n=0, 1, 2, or 3) and R is hydrogen, carboxyl, or aromatic; E is N,

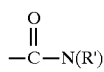

where R' is hydrogen or methyl, or S; and Y is a hydroxyalkyl phosphine of the formula $P(A\text{—}OH)_n$ where (n=1, 2, or 3) and where A is —$CH_2$, —$C_2H_4$, or iso- or normal-$C_3H_6$—. In a preferred embodiment of the present invention, A is methyl.

Applicants have discovered and demonstrated herein that a new class of chelating bisphosphines of the type: $((HOH_2C)_2PCH_2CH_2P(CH_2OH)_2$(HMPE) and $(HOH_2C)_2PC_6H_4P(CH_2OH)_2$ (HMPB)) are oxidatively stable in air and also in aqueous solutions.

Figure 13:
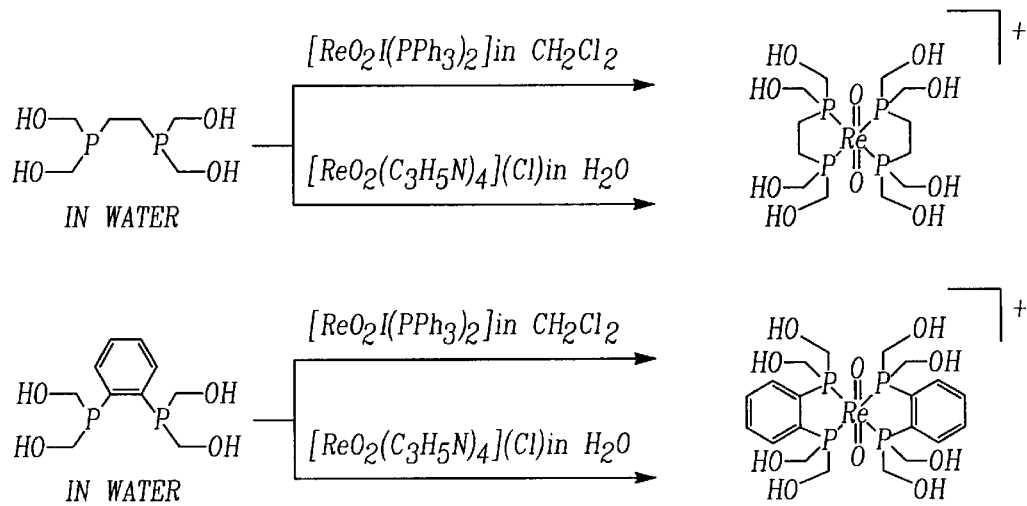
FIG. 13 illustrates a synthesis scheme for the synthesis of rhenium complexes in accordance with the present invention.

These ligands also produce water-soluble (and kinetically inert) complexes with a number of early (Re(V) and 99mTc (V)) and late (Rh(I), Pd(II), Pt(II), Ag(I), and Au(I)) transition metals (Berning et al., 1996, Berning et al., In Press, Berning et al., In Press, Berning et al., 1995, Ellis et al., 1992, Harrison et al., 1989, Hoye et al., 1993, Reddy et al., 1995, Reddy et al., 1996, Reddy et al., 1996). Detailed radiochemical investigations of THP, HMPB, and HMPE with Tc-99m have demonstrated that hydroxymethyl-functionalized phosphines (HMP) not only produce $^{99m}Tc$-complexes with high in vivo stability, but also that the complexes are efficiently cleared from non-target tissues with a high degree of excretion into the urine (Berning et al., 1996, Berning et al. 1995). However, our detailed studies, including synthetic and X-ray crystallographic investigations, of the reactions of HMPB and HMPE with various Re(V) precursors have indicated that these ligands have strong propensities to form complexes with two ligands coordinating to one Re(V) center as outlined in Scheme 1 of FIG. 13 (Reddy et al., 1996). In order to develop an effective bifunctional chelating agent (BFCA) for use in labeling biomolecules, it is essential that the metal:ligand ratio be 1:1. The HMPB and HMPE ligands, although unsuitable for BFCAs, may have useful implications in nuclear medicine if new ligands are designed incorporating —$P(CH_2OH)_2$ groups within their backbone. Therefore, the possibility of appending HMP groups to dithioether frameworks (FIG. 1) was explored so that the combined ligating characteristics of sulfur and $P^{III}$ centers could provide metal complexes with 1:1 metal to ligand ratio (Smith et al., In Press, Smith et al., Submitted for publication). The in vitro and in vivo radiochemical investigations of technetium-99m with this new class of ligands is disclosed herein. The chemical properties of the resulting complexes are compared to those of the known rhenium(V) analogues.

These properties coupled with the high in vitro/in vivo stability of Tc-99m complexes derived from HMPE and HMPB, presented prospects for further ligand modifications of (hydroxymethyl) phosphine-based ligands. Applicants describe herein (a) the synthesis of a new series of water-soluble ligands based on dithio-bisphosphine backbones, $[(HOH_2C)_2P(CH_2)_2S(CH_2)_3S(CH_2)_2P(CH_2OH)_2(1)$, $(HOH_2C)_2PCH_2CH_2S(CH_2)_4SCH_2CH_2P(CH_2OH)_2$ (4) and $(HOH_2C)_2PCH_2CH_2CH_2S(CH_2)_3SCH_2CH_2CH_2P(CH_2OH)_2]$ (7), (b) the coordination chemistry of these ligands with Re(V) and the ligands $(HOH_2C)_2P(CH_2)_2S(CH_2)_3S(CH_2)_2P(CH_2OH)_2$ (11) and $(HOH_2C)_2P(CH_2)_3S(CH_2)_3S(CH_2)P(CH_2OH)_2$ (12) with $^{99m}Tc$ demonstrating the importance of ligand chain size to produce complexes with 1:1 metal to ligand ratios, and (c) X-ray crystal structures of $[ReO_2(HOH_2C)_2P(CH_2)_2S(CH_2)_3S(CH_2)_2P(CH_2OH)_2]_2Cl_2$ (8), $[ReO_2(HOH_2C)_2P(CH_2)_2S(CH_2)_4S(CH_2)_2P(CH_2OH)_2]_2Cl_2$ (9), and $[ReO_2(HOH_2C)_2P(CH_2)_3S(CH_2)_3S(CH_2)_3P(CH_2OH)_2]Cl$ (10). In vitro studies demonstrating the kinetic inertness of new water-soluble Re (V) complexes derived from dithiobisphosphine ligands are described below.

Compounds containing hydroxyalkyl phosphine donor groups made in accordance with the present invention can also be chemically modified or linked with site specific biomolecules to produce specificity of tissue localization, improved pharmacokinetics, and increased selectivity of target tissues such as tumors over normal tissues which include, but are not limited to, bone marrow, kidney, G.I. tract, and liver.

The above formulas characterize the present invention as being very modifiable in order to specifically tailor the ligand for chelation with a specific radionuclide and localization at a specific target organ.

For example, the ligand can be conjugated to proteins or antibodies and can use side chains previously used for linking monoclonal antibodies. For example, conjugation reactions can involve reactive groups such as benzyl isothiocyanate, bromoacetamide, activated esters, N-hydroxysuccinimides, cleavable ester linkages, and aldehydes. Accordingly, a single monoclonal antibody or several monoclonal antibodies can be added to the metal-ligand complex to provide specificity of the binding of the ligand metal complex to specific surface antigen or target tissue.

As discussed above, other side chain modifications can be accomplished to make the chelate more polar and hydrophilic. For example, charged groups such as carboxyl or hydroxyl groups can be added at the various R groups appended to the phosphine groups. This additional small change in the compounds providing charged/polar groups increases the hydrophilic character of the resulting chelate. This produces more rapid and selective clearance from the blood and nontarget tissue. This modification is highly desirable for the promotion of efficient clearance of radioactivity from nontarget tissues, such as blood, liver, kidney, and spleen following catabolism of conjugated radiolabeled monoclonal antibodies that are presently used for therapy.

Alternatively, the hydrophobicity of the chelate can be varied incrementally by varying the alkyl chain length of the side chains appended to the phosphine groups. For example, the alkyl groups on the phosphine moiety can be derivatized with for example methyl, ethyl, and normal- or iso-propyl. This is desirable because with some chelates, particularly those labeled with $^{99m}Tc$, an increase in the hydrophobicity of the chelate plays a major role in targeting uptake in selective tissues, such as in brain, heart and lung. Addition of alkyl groups to the chelating backbone increases the lipid solubility of the chelate. If the resulting chelate is neutral, either brain, heart, or lung imaging agents can be developed.

An alternative to varying the alkyl chain length of the R and R' groups appended to the phosphine moieties is to add other functional groups, such as —OH, —SH, —$NH_2$, —COOH, activated esters, N-hydroxysuccinimides benzyl isothiocyanate, alkyl halides, or cylclohexyldimide. The use of ether substitutions instead of the alkyl side chains will increase lipophilicity but also improves the rate of clearance of the chelate from the blood and other non-target tissues.

All of the aforementioned modifications demonstrate the flexibility of compounds made in accordance with the present invention and further the ability to modify these compounds to alter the binding, elimination, and absorption of the compounds in order to tailor the compounds for specific organ targeting, dosing, and metabolism.

The compounds produced in accordance with the present invention can be utilized by methods well known in the art as radio-pharmaceuticals for either radio-imaging or therapeutic treatment of diseases such as cancers, infections, neurological disorders, cardiac diseases, and further includes a wide variety of disorders that are currently evaluated in nuclear medicine laboratories. $^{99}$Tc can be used for all diagnostic imaging studies while $^{105}$Rh and $^{186/188}$Re can only be used therapeutically primarily for the treatment of cancers.

The compounds produced in accordance with the present invention are administered and dosed in accordance with good medical practice, taking into account the clinical condition of the individual patient, the site and method of administration, scheduling of administration, and other factors known to medical practitioners. The "effective amount" for purposes herein is thus determined by such considerations as are known in the art.

In the method of the present invention, the metal-hydroxyalkyl containing compounds (complexes) can be administered in various ways. It should be noted that the compounds can be administered as the compound or as pharmaceutically acceptable salt and can be administered alone or in combination with pharmaceutically acceptable carriers. The compounds can be administered orally or parenterally including intravenous, intraperitoneally, intranasal and subcutaneous administration. Implants of the compounds are also useful. The patient being treated is a warm-blooded animal and, in particular, mammals including man.

When administering the metal-hydroxyalkyl phosphine containing compounds parenterally, the pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like.

According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the metal-hydroxyalkyl phosphine containing compounds can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as polymer matrices, liposomes, and microspheres. An implant suitable for use in the present invention can take the form of a pellet which slowly dissolves after being implanted or a biocompatible delivery module well known to those skilled in the art. Such well known dosage forms and modules are designed such that the active ingredients are slowly released over a period of several days to several weeks.

The compounds of the present invention are administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the present invention, the compounds can be administered in various ways. It should be noted that the compounds can be administered as the compound or as pharmaceutically acceptable salt and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. The patient being treated is a warm-blooded animal and, in particular, mammals including man.

When administering the compounds of the present invention parenterally, the compounds will be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the compounds of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. No. 5,225,182; U.S. Pat. No. 5,169,383; U.S. Pat. No. 5,167,616; U.S. Pat. No. 4,959,217; U.S. Pat. No. 4,487,603; U.S. Pat. No. 4,486,194; U.S. Pat. No. 4,447,233; U.S. Pat. No. 4,447,224; U.S. Pat. No. 4,439,196; and U.S. Pat. No. 4,475,196. Many other such implants, delivery systems, and modules are well known to those skilled in the art.

A pharmacological formulation of the compounds of the present invention utilized in the present invention can be administered orally to the patient. Conventional methods such as administering the compounds in tablets, suspensions, solutions, emulsions, capsules, powders, syrups and the like are usable. Known techniques which deliver the compounds orally or intravenously and retain the biological activity are preferred.

For delivery within the CNS, pharmacological formulations that cross the blood-brain barrier can be administered. (Betz et al., 1994; Brem et al., 1993) Such formulations can take advantage of methods now available to produce chimeric peptides in which the present invention is coupled to a brain transport vector allowing transportation across the barrier. (Pardridge, et al., 1992; Pardridge, 1992; Pardridge, et al., 1993)

In one embodiment, the compounds can be administered initially by intravenous injection to bring blood levels of compounds to a suitable level. The patient's blood levels are then maintained by an oral dosage form, although other forms of administration, dependent upon the patient's condition and as indicated above, can be used. The quantity of compound to be administered will vary for the patient being treated and will vary from about 100 ng/kg of body weight to 100 mg/kg of body weight per day and preferably will be from 10 $\mu$g/kg to 10 mg/kg per day.

Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are well known to those skilled in the art.

Figure 2:
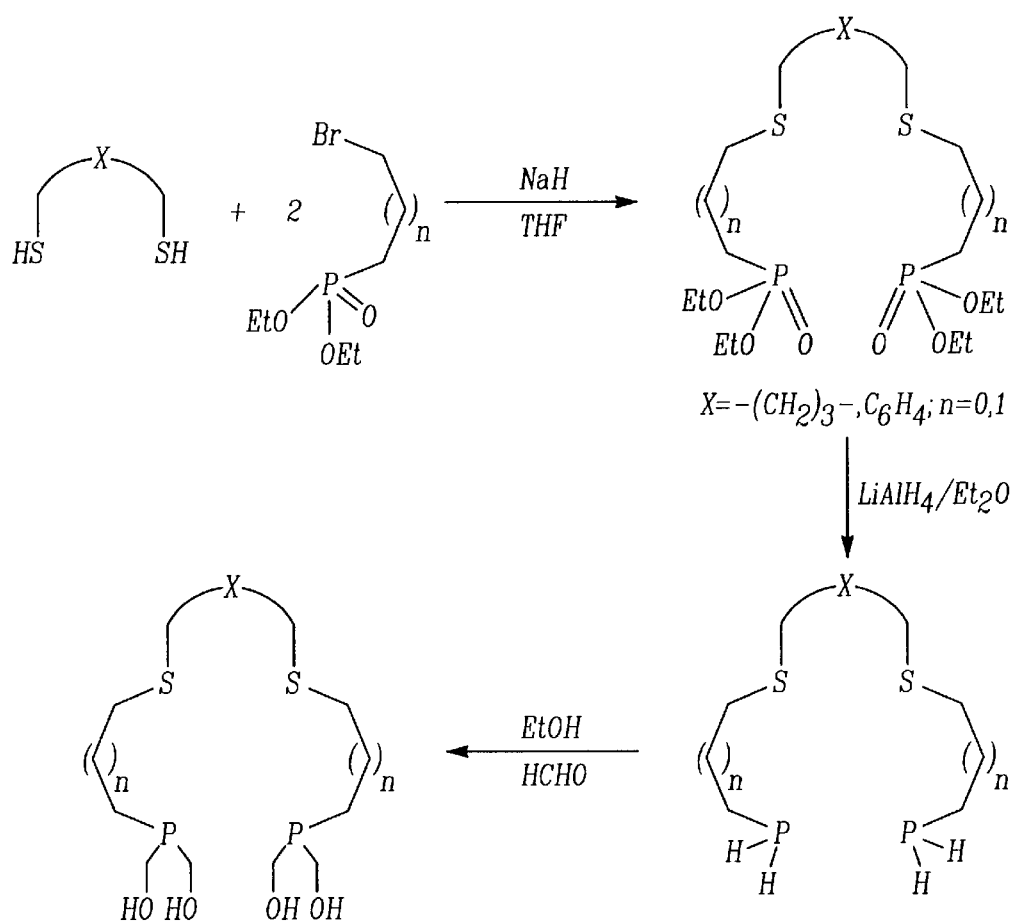
FIG. 2 illustrates a synthesis scheme for the synthesis of dithio-bisphosphanes of the general formula P$_2$S$_2$ in accordance with the present invention (compounds 1 and 2)
Figure 3:
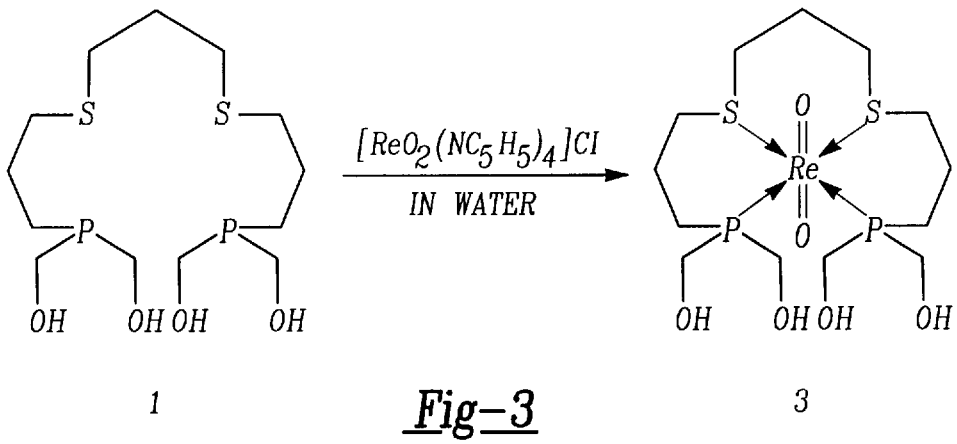
FIG. 3 illustrates a synthesis scheme for the synthesis of a rhenium complex in accordance with the present invention (compound 3)

Various HMP-based multi-dentate phosphines and their methods of synthesis in accordance with the present invention are illustrated in FIGS. 2–4.

Formation of $^{99m}$Tc (and $^{186/188}$ReO$_4^-$) can be performed by reduction of $^{99m}$TcO$_4^-$ by excess of the phosphine ligand, an external reducing agent, e.g., Sn(II) or by transchelation from a donor $^{99m}$Tc or $^{186/188}$Re synthon.

In a further embodiment of the present invention, multi-dentate hydroxyalkyl phosphine based ligands can be used to form $^{99m}$Tc or $^{186/188}$Re complexes in aqueous systems by transchelation from weaker donor chelates (e.g., $^{99m}$Tc(V)-glucoheptonate, $^{186/188}$Re(V)-citrate), following reduction with external reducing agents (e.g., Sn$^{+2}$), or without external reducing agents. This approach utilizes ligand frameworks containing greater than or equal to ($\geq$) one (1) hydroxyalkyl phosphine donor group(s). In one such embodiment, a hydroxyalkyl phosphine donor group on a multi-dentate ligand backbone is utilized so that the phosphine functionality of the molecule reduces $^{99m}$TcO$_4^-$ or $^{186/188}$ReO$_4^-$ and the other intramolecular phosphines or other donor atoms (e.g., —N, —O, —P or —S atoms) interact to form stable chelates with the reduced radiometals.

Most of the hydroxyalkyl phosphine containing ligands used to form BFCAs are multi-dentate (i.e., $\geq$3 donor atoms) and, generally, form 1:1 ligand-to-metal complexes with the reduced (i.e., oxidation states <+7) $^{99m}$Tc and $^{186/188}$Re as shown in FIG. 3.

The present invention also provides a method for separating uncoordinated hydroxyalkyl phosphine groups from hydroxyalkyl phosphine groups coordinated with metal atoms by reacting the uncoordinated hydroxyalkyl phosphine groups with an amine to remove the uncoordinated groups thereby yielding a substantially hydroxyalkyl phosphine-metal compound.

Generally, this method allows for the separation of metal-hydroxymethyl phosphine (HMP) complexes such as complexes of $^{99m}$Tc-(or $^{186/188}$Re) complexes with ligands containing HMP groups. That is, the method allows for the separation of complexes where all of the HMP groups on the ligand backbone are coordinated to the metal from ligands from uncoordinated HMP groups that are not complexed with the metal. This method allows for the simple and rapid removal of any excess uncomplexed ligands with HMP groups from solutions containing $^{99m}$Tc (or $^{186/188}$Re) complexed with these ligands to obtain $^{99m}$Tc (or $^{186/188}$Re) products including radiopharmaceuticals, and high-specific activities. This separation is made possible by the discovery that HMP groups that are not coordinated to the metal, i.e., $^{99m}$Tc (or $^{186/188}$Re), will efficiently react with amines while HMP groups coordinated to the metals will not react with amines.

Utilization of this technology is well suited for applications in routine radiopharmaceutical preparations where $^{99m}$Tc (or $^{186/188}$Re) labeled agents, after removal of excess uncomplexed HMP-containing molecules, can be administered to human patients.

In a preferred embodiment of this method, the preferred group utilized for the removal of the uncoordinated HMP's would include amine functionalities (i.e., primary or secondary amines) which can be appended to a solid surface, such as a standard separation column or bed material, i.e., resins or other solid matrices. Using amines bound to resins or other solid matrices allows the separation of any uncomplexed ligands, containing one or more HMP groups not coordinated to the metal, in a facile operation. For example, the $^{99m}$Tc (or $^{186/188}$Re) labeled compound or radiopharmaceutical could be formed, via an appended ligand backbone containing HMP groups that will coordinate the metal, in a sterile aqueous solution, such as 0.9% NaCl, and then the solution could be passed through a sterile column containing a solid support with excess amine groups attached to its surface. As the solution passes through the column, any compounds with uncomplexed HMP groups would be covalently bound to the column, while all HMP-containing compounds in which the HMP groups are coordinated to the metal would pass through the column into the eluate. The utility of this method is demonstrated below in the example section for a mono-dentate HMP ligand, tris (hydroxymethyl) phosphine (THP).

EXAMPLES

LIGANDS SYNTHESIZED

Example 1

Dithio-bisphosphane Ligands 1 and 2 (FIG. 2)

The dithio-bisphosphane ligands produced in accordance with the present invention can be characterized by the following formula

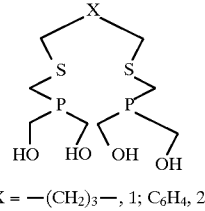

$X = -(CH_2)_3-$, 1; $C_6H_4$, 2 where X can be further modified to incorporate an aliphatic or aromatic group functionalized with —COOH, —NCS, or succinimide functionalities for attachment to biomolecules.

The dithiobiophosphanes of formula 1 and 2, as shown in FIG. 2, were prepared by methods outlined below:

Synthesis of $(EtO)_2(O)PCH_2CH_2S(CH_2)_3SCH_2CH_2P(O)(OEt)_2$:

A sample of 60% NaH in mineral oil (95 mmol) was placed in a 2-neck round bottom flask and charged with dry hexane (20 mL). This solution was allowed to stir for ten minutes, after which the hexane-mineral oil layer was completely removed. The flask was then charged with dry tetrahydrofuran (100 mL), followed by dropwise addition of $HS(CH_2)_3SH$ (46 mmol) with constant stirring. The resulting solution was cooled at 0° C. and $BrCH_2CH_2P(O)(OC_2H_5)_2$ (95 mmol) was added dropwise with constant stirring over a period of 30 minutes. Excess NaH was quenched by addition of 50 mL of deionized water. The solution was extracted from ethyl acetate (3×50 mL) and washed with a saturated sodium chloride solution. The organic layer was dried over anhydrous sodium sulfate. Upon filtering, the solvent was removed in vacuo to afford compound 5 in 90% yield along with a trace amount of diethyl vinylphosphonate. The compounds were separated on a silica gel column (20 cm; 60 mesh) using 90:10 ethyl acetate to hexane solvent mixture. Removal of the solvent in vacuo, afforded compound 5 as a viscous, yellow-green oil with an overall yield of 88%. High resolution FAB/MS Anal. Calcd. for $C_{15}H_{34}O_6P_2S_2$: 436.1272; Found: [M+H$^+$], m/z= 437.1350. $^1$H NMR (CDCl$_3$): δ 1.34 (t, $^3J_{HH}$=9.0 Hz, 12H, OCH$_2$C$\underline{H}_3$), 1.87 (qn, 2H, CH$_2$C$\underline{H}_2$CH$_2$), 2.03 (m, 4H, PC$\underline{H}_2$CH$_2$), 2.65 (t, $^3J_{HH}$=9.0 Hz, 4H, C$\underline{H}$CH$_2$C$\underline{H}_2$), 2.74 (m, 4H, PCH$_2$C$\underline{H}_2$), 4.11 (m, 8H, OC$\underline{H}_2$CH$_3$). $^{13}$C NMR (CHCl$_3$): δ 16.3 (d, $^3J_{PC}$=4.5 Hz, OCH$_2$$\underline{C}$H$_3$), 24.8 (d, $^2J_{PC}$=3.0 Hz, PCH$_2$$\underline{C}$H$_2$), 26.6 (d, $^1J_{PC}$=136.6 Hz, P$\underline{C}$H$_2$CH$_2$), 28.5 (s, CH$_2$$\underline{C}$H$_2$CH$_2$), 30.5 (s, $\underline{C}$H$_2$CH$_2$CH$_2$), 61.6 (d, $^2J_{PC}$=6.0 Hz O$\underline{C}$H$_2$CH$_3$). $^{31}$P NMR (CDCl$_3$): δ 29.1 (s).

Synthesis of $H_2PCH_2CH_2S(CH_2)_3SCH_2CH_2PH_2$:

Compound 5 (18 mmol) was placed in 75 mL of dry diethyl ether and cooled to 0° C. An either solution of 1.0M lithium aluminum hydride (45 mmol, 45 mL) was slowly added dropwise to this solution with constant stirring. An aqueous solution of 6N hydrochloric acid (50 mL) was added dropwise to the solution to quench any remaining LiAlH$_4$. The ether layer was separated by cantellation and the solvent was removed in vacuo to afford compound 7 in quantitative yield as a colorless, viscous oil. $^1$H NMR (CDCl$_3$): δ 1.83 (m, 6H, PC$\underline{H}_2$CH$_2$, CH$_2$C$\underline{H}_2$CH$_2$), 2.70 (m, 12H, PH$_2$, C$\underline{H}_2$CH$_2$C$\underline{H}_2$, PCH$_2$C$\underline{H}_2$). $^{13}$C NMR (CDCl$_3$): δ 14.8 (d, $^1J_{PC}$=11.3 Hz, P$\underline{C}$H$_2$CH$_2$), 29.1 (s, CH$_2$$\underline{C}$H$_2$CH$_2$), 30.6 (s, $\underline{C}$H$_2$CH$_2$CH$_2$), 35.1 (s, PCH$_2$$\underline{C}$H$_2$). $^{31}$P NMR (CDCl$_3$): δ-137.1 (s).

Synthesis of $(HOH_2C)_2PCH_2CH_2S(CH_2)_3SCH_2CH_2P(CH_2OH)_2$ (1) ($P_2S_2$)

Aqueous formaldehyde (78 mmol) was placed in 50 mL of oxygen free ethanol and purged with nitrogen gas for two hours at 25° C. Compound 7 (18 mmol) was then added dropwise to the solution via syringe with constant stirring at 25° C. The reaction was complete in twelve hours, as monitored by 31P NMR spectroscopy. Removal of the solvent in vacuo afforded compound 1 in near quantitative yield, as a colorless, viscous oil. High resolution FAB/MS Anal. Calcd. for $C_{11}H_{26}O_4P_2S_2$: 348.0748; Found: [M+H$^+$], m/z=349.0826. Anal. Calcd. for $C_{11}H_{26}O_4P_2S_2$: C, 37.92; H, 7.53: Found: C, 37.12; H, 6.76. $^1$H NMR (D$_2$O): δ 1.80 (m, 6H, PC$\underline{H}_2$CH$_2$, CH$_2$C$\underline{H}_2$CH$_2$), 2.57 (m, 8H, C$\underline{H}_2$CH$_2$C$\underline{H}_2$, PCH$_2$C$\underline{H}_2$), 3.93 (m, 8H, PC$\underline{H}_2$OH). $^{13}$C NMR (D$_2$O): δ 19.6 (d, $^2J_{PC}$=9.1 Hz, PCH$_2$$\underline{C}$H$_2$), 27.7 (d, $^1J_{PC}$=18.2 Hz, P$\underline{C}$H$_2$CH$_2$), 28.1 (s, CH$_2$$\underline{C}$H$_2$CH$_2$), 29.7 (s, $\underline{C}$H$_2$CH$_2$CH$_2$) 57.8 (d, $^1J_{PC}$=9.8 Hz, P$\underline{C}$H$_2$OH). $^{31}$P NMR (D$_2$O): δ-25.0 (s).

Synthesis of $C_6H_4\{1,2-SCH_2CH_2P(O)(OEt)\}_2$

A sample of 60% NaH in mineral oil (32 mmol) was placed in a 2-neck round bottom flask and charged with dry hexane (20 mL). This solution was allowed to stir for ten minutes, after which the hexane-mineral oil layer was completely removed. The flask was then charged with dry tetrahydrofuran (100 mL), followed by dropwise addition of 1,2-HS(C$_6$H$_4$)SH (14 mmol) with constant stirring. The resulting solution was cooled at 0° C. and BrCH$_2$CH$_2$P(O)(OC$_2$H$_5$)$_2$ (30 mmol) was added dropwise with constant stirring over a period of 30 minutes. Excess NaH was quenched by addition of 50 mL of deionized water. The solution was extracted from the ethyl acetate (3×50 mL) and washed with a saturated sodium chloride solution. The organic layer was dried over anhydrous sodium sulfate. Upon filtering, the solvent was removed in vacuo to afford 6 in 94% yield along with a trace amount of diethyl vinylphosphonate. The compounds were separated on a silica gel column (20 cm; 60 mesh) using 90:10 ethyl acetate to hexane solvent mixture. Removal of the solvent in vacuo, afforded compound 6 as a viscous, yellow-green oil with an overall yield of 91%. High resolution FAB/MS Anal. Calcd. for $C_{18}H_{32}O_6P_2S_2$: 470.1115; Found: [M+H$^+$], m/z= 471.1119. $^1$H NMR (CDCl$_3$): δ 1.27 (t, $^3J_{HH}$=9.0 Hz, 12H, OCH$_2$C$\underline{H}_3$), 2.02 (m, 4H, PC$\underline{H}_2$CH$_2$), 3.06 (m, 4H, PCH$_2$C$\underline{H}_2$), 4.05 (m, 8H, OC$\underline{H}_2$CH$_3$), 7.2 (m, 4H, C$_6$H$_4$). $^{13}$C NMR (CDCl$_3$): δ 16.3 (d, $^3J_{PC}$=6.0 Hz, OCH$_2$$\underline{C}$H$_3$), 25.8 (d, $^1J_{PC}$=136 Hz, P$\underline{C}$H$_2$CH$_2$), 26.2 (s, PCH$_2$$\underline{C}$H$_2$), 61.7 (d, $^2J_{PC}$=6.0 Hz, O$\underline{C}$H$_2$CH$_3$). $^{31}$P NMR (CDCl$_3$): δ29.4 (s).

Synthesis of $C_6H_4\{1,2-SCH_2CH_2PH_2\}_2$

Compound 6 (12 mmol) was placed in 75 mL of dry diethyl ether and cooled to 0° C. An ether solution of 1.0M lithium aluminum hydride (31 mmol, 31 mL) was slowly added dropwise to this solution with constant stirring. An aqueous solution of 6N hydrochloric acid (50 mL) was added dropwise to the solution to quench any remaining LiAlH$_4$. The ether layer was separated by cantellation and the solvent was removed in vacuo to afford compound 8 in quantitative yield as a colorless, viscous oil. $^1$H NMR (CDCl$_3$): δ1.81 (s, 4H, PC$\underline{H}_2$CH$_2$), 2.47 (s, 2H, PH$_2$), 3.07

(m, 6H, PH$_2$, PCH$_2$C$\underline{H}_2$), 7.21 (m, 4H, C$_6$H$_4$). $^{13}$C NMR (CDCl$_3$): δ 14.2 (d, $^1J_{PC}$=15.1 Hz, PC$\underline{H}_2$CH$_2$), 36.4 (s, PCH$_2$C$\underline{H}_2$), 126.6 (s, C-m), 129.5 (s,C-o), 136.7 (s, C-S). $^{31}$P NMR (CDCl$_3$): δ-136.3 (s).

Synthesis of C$_6$H$_4${1,2-SCH$_2$CH$_2$P(CH$_2$OH)$_2$}$_2$ (2)

Aqueous formaldehyde (53 mmol) was placed in 50 mL of oxygen free ethanol and purged with nitrogen gas for two hours at 25° C. Compound 8 (12 mmol) was then added dropwise to the solution via syringe with constant stirring at 25° C. The reaction was complete in 30 hours, as monitored by $^{31}$P NMR spectroscopy. Removal of the solvent in vacuo afforded compound 2 in near quantitative yield, as a colorless, viscous oil. High resolution FAB/MS Anal. Calcd. for C$_{14}$H$_{24}$O$_4$P$_2$S$_2$: 382.0591; Found: [M+H$^+$], m/z= 383.0651. Anal. Calcd. for C$_{14}$H$_{24}$O$_4$P$_2$S$_2$: C, 43.97; H, 6.33; Found: C, 44.23; H, 5.80. $^1$H NMR (D$_2$O): δ 1.93 (m, 4H, PC$\underline{H}_2$CH$_2$), 3.09 (m, 4H, PCH$_2$C$\underline{H}_2$), 4.02 (d, $^2J_{PH}$=9.0 Hz, PCH$_2$OH), 7.23 (m, 4H, C$_6$H$_4$). $^{13}$C NMR (D$_2$O): δ 19.4 (d, $^2J_{PC}$=13.0 Hz.

A $^{99m}$Tc chelate with ligand (1) was prepared by mixing 0.1 ml of 0.9% aqueous NaCl (N. saline) containing $^{99m}$TcO$_4^-$ (0.5–5 mCi) with 0.4 ml of N. saline containing 1 mg/ml of P$_2$S$_2$ and incubated at room temperature (RT) for thirty minutes. The $^{99m}$Tc product was found to be hydrophilic and cationic by electrophoretic analysis. HPLC analyses were performed using a reversed-phase, PRP-1 column eluted using a gradient. Solvent A=100% 0.01M sodium phosphate at pH 7; solvent B=100% MeCN. The gradient profile was 100% A for two minutes post injection (P.I.) followed by a linear gradient from zero B to 100% B from two minutes to seven minutes P.I., followed by 100% B for an additional six minutes (i.e., until fifteen minutes P.I.). Two peaks were observed; one with a retention time of 1.3 minutes (same as $^{99m}$TcO$_4^-$) and the other at 6.57 minutes. The HPLC and electrophoretic analyses indicated that the $^{99m}$Tc chelate is a single species and is formed in >95% yields. This $^{99m}$Tc chelate was found to be stable in aqueous solutions at pH ranging from 4–11 and pH ranging from 7.4–7.8 at 37° C. for ≧24 hr as shown in Table 2.

The biodistribution of $^{99m}$Tc-P$_2$S$_2$ in anesthetized rats (Sprague-Dawley rats anesthetized intraperitoneally with 50 mg/kg of Na-pentobarbital) (see Table 5) at two minutes and thirty minutes post-injection (intravenous injection) showed the route of clearance is primarily into the urine via the kidneys. No evidence of in vivo dissociation of the chelate to form $^{99m}$TcO$_4^-$ is evident since the amount of $^{99m}$Tc activity found in the stomach was minimal (see Table 3). These data provide evidence that dithio-hydroxyalkyl phosphines can form $^{99m}$Tc-chelate(s) that have excellent in vitro (pH 4–11) and in vivo stability. Furthermore, the fact that a $^{99m}$Tc chelate was formed by simply mixing $^{99m}$TcO$_4^-$ with ligands 1 (or in saline is evidence that this phosphine ligand is capable of reducing $^{99m}$Tc from the +7 oxidation state in pertechnetate to a lower oxidation state that is able to chelate with other P$_2$S$_2$ molecules present in excess.

Example 2

Multidentate Diamido-biophosphine (Compound 4 in FIG. 4):

Diamido-biophosphine compound 4 was synthesized employing a four-step synthetic process as described below:
Experimental Details for the Synthesis of P$_2$N$_2$ Ligands:
Preparation of Diethyl-(2-N, N-dibenzylaminoethyl) phosphonate:

To Diethyl 2-bromoethyl phosphonate (50 g, 0.2 mole) in a single necked RB flask fitted with condenser was added dibenzyl amine (400 ml) while stirring at room temperature. The mixture was heated at 100° C. During a period of one hour the reaction mixture solidified and the heating was continued for twenty-four hours. Dichloromethane (300 ml) was added to the reaction flask and the dibenzylammonium bromide was filtered and washed thoroughly with dichloromethane (3×50 ml). The combined filterate was concentrated on a rotary evaporator. The pure phosphonate (55.4 g, 75%) was obtained by distillation under reduced pressure (180° C., 0.1 mm/Hg).

IR: v3028, 2982, 1601, 1452, 1250, 1028, 745, 700 cm$^{-1}$
$^1$H NMR: δ 7.16 (m, 10H), 3.84 (m, 4H), 3.44 (s, 4H), 2.67 (m, 2H), 1.83 (m, 2H), 1.15 (t, J$_1$=J$_2$=7.05 Hz)
$^{13}$C NMR: δ 138.63, 128.27, 127.79, 126.55, 60.95, 57.26, 45.95, 22.57 (d, J=136.5 Hz), 15.86
$^{31}$P NMR: δ 32.24

Preparation of (2-N, N-dibenzylaminoethyl)bis (hydroxymethyl)phosphine oxide:

Into a 250 ml RB flask fitted with reflux condenser was placed the phosphonate (7.24 g, 20 mmol) in dry ether (100 ml). The solution was cooled to 0° C. and LAH (30 ml, 1.0M in ether, 30 mmol) was added via syringe dropwise while stirring under N$_2$ atmosphere. After stirring at room temperature for two hours, a saturated solution of Na$_2$SO$_4$ (15 ml) was added at 0° C. to destroy the excess LAH. The ethereal layer was transferred via cannula to another 500 ml RB flask. The ether was removed under reduced pressure at room temperature. The residue was dissolved in degassed ethanol (50 ml) and was added to a solution of 37% formaldehyde (5 g, 61 mmol) in ethanol (75 ml). The mixture was stirred for four hours and 30% hydrogen peroxide (1 ml) was added. The mixture was stirred for another 30 minutes. The solvent was removed under reduced pressure at room temperature and the crude was purified on a silica gel column by eluting with 10% methanol-dichloromethane mixture to get 5.01 g in 75% yield.

$^1$H NMR: δ 7.27 (m, 10H), 5.69 (br s, 2H), 3.74 (q, 4H), 3.56 (s, 4H), 2.82 (m, 2H), 2.05 (m, 2H)
$^{13}$C NMR: δ 137.09, 129.29, 128.41, 127.46, 57.98, 57.21 (d), 45.60, 21.6 (d)
$^{31}$P NMR: δ 51.52
Mass: Calcd: 333.36; Found: 333.1

Protection of (2-N, N-dibenzylaminoethyl) bis (hydroxymethyl)phosphine oxide:

To a mixture of bis-hydroxy compound (2 g, 5.99 mmol), 4-dimethylaminopyridine (750 mg, 6.1 mmol) and triethyl amine (1.9 g, 18.7 mmol) in dichloromethane (50 ml) was added t-butyldimethylsilyl chloride (2.8 g, 18.57 mmol) at 0° C. under N$_2$ and stirred overnight at room temperature. The reaction mixture was diluted with dichloromethane (100 ml), washed with water (20 ml), brine (20 ml) and dried over anhydrous Na$_2$SO$_4$. The solvent was removed and the crude was charged on a silica gel column. The column was eluted with 30% ethyl acetate-hexane mixture to obtain (3.28 g) of silylated compound in 97% yield.

IR: v3028, 2930, 2857, 1472, 1255, 1188, 1099, 835, 781, 698 cm$^{-1}$
$^1$H NMR: δ 7.42 (m, 10H), 4.06 (m, 4H), 3.73 (s, 4H), 3.04 (m, 2H), 2.14 (m, 2H), 1.02 (m, 18H), 0.18 (d, 12H)
$^{13}$C NMR: δ 138.78, 128.55, 128.11, 126.85, 57.7 (d), 57.54, 45.57, 25.61, 20.3 (d), 18.03, −5.87
$^{31}$P NMR: δ 48.25
Mass: Calcd. 561.89, Found: 561.3

Preparation (2-Aminoethyl)bis(hydroxymethyl)phosphine oxide:

The dibenzylated compound (3 g), in ethanol (25 ml) was hydrogenated over Pd/C for two days. The solvent was removed under reduced pressure and used as such for the preparation of bisamide.

$^1$H NMR: δ 4.11 (m, 4H), 2.17 (br s, 2H), 2.07 (m, 2H), 0.99 (s, 18H), 0.20 (s, 12H)
$^{13}$C NMR: δ 58.1 (d), 35.20, 26.58 (d), 25.56, 18.03, −5.85
$^{31}$P NMR: δ 48.78
Mass: Calcd: 381.64, Found: 381.2
Preparation of diamide-diphosphine:

To a mixture of phthloyl dichloride (1.5 g, 7.38 mmol) and triethylamine (2.3 g, 22.72 mmol) in dry dichloromethane was added the hydrogenated compound (6.4 g, 16.76 mmol) under $N_2$. The mixture was stirred overnight at room temperature. Diluted with dichloromethane, washed with water and brine. Dried over anhydrous $Na_2SO_4$ and the solvent was removed under reduced pressure. The crude product was purified on a silica gel column by eluting with 2% methanol-dichloromethane mixture to get (3.1 g) of the bisamide in 46% yield.

IR: ν 3268, 3065, 2930, 2859, 1537, 1472, 1316, 1255, 1098, 1007, 838, 779 cm$^{-1}$
$^1$H NMR: δ 7.67 (m, 4H), 7.50 (m, 2H), 4.13 (m, 8H), 3.93 (m, 4H), 2.21 (m 4H), 0.99 (s, 36H), 0.20 (m, 24H)
$^{13}$C NMR: δ 168.65, 135.19, 130.02, 127.91, 57.97 (d), 33.54, 25.65, 22.41 (d), 18.13, −5.75
$^{31}$P NMR: δ 49.48
Mass: Calcd: 893.38, Found: 892.4

Trichlorosilane (3 ml) was added to the bisamide (250 mg, 0.27 mmol) under $N_2$. The mixture was stirred for 2 h and the progress of the reaction was monitored by $^{31}$P NMR. After completion of the reaction, the excess trichlorosilane was removed by passing a stream of $N_2$ gas. The residue was suspended in water and undissolved solid was filtered. The filterated was concentrated to get the crude phosphonium salt (100 mg).
$^{31}$P NMR: δ 29.5

Example 3

$^{99m}$Tc-chelates of the $N_2P_2$ ligand 4 were prepared by two different methods: (i) by simply mixing 0.1 ml of N. saline containing $TcO_4^-$ (0.5–5 mCi) with 0.4 ml of N. saline containing 1 mg/ml of compound 4 and incubated for one hour; (ii) by ligand exchange reactions in which $^{99m}$Tc-glucoheptonate (or $^{99m}$Tc citrate) were used as complexing agents to compound 4. The $^{99m}$Tc-$N_2P_2$ complex was formed at neutral (pH 6–7) by mixing 0.5 ml of the ligand solution in water (1 mg/ml) with 0.5 ml of an aqueous solution of $^{99}$Tc-glucoheptonate (or $^{99m}$Tc-citrate). The $^{99m}$Tc-$N_2P_2$ complexation yields at different time intervals for the $^{99m}$Tc-citrate exchange reactions are summarized in Table 4.

The yields of $^{99m}$Tc $N_2P_2$ complex produced via the direct addition of $^{99m}$TcO$_4^-$ with an aqueous solution of $N_2P_2$ ligand 4 was also high (~95–98%). The products were analyzed by electrophoresis and HPLC. HPLC analysis was performed by reversed phase (PRP-1 column) chromatography using the gradient elution system previously described. The $^{99m}$Tc-chelates formed with both $^{99m}$Tc-citrate and $^{99m}$Tc-glucoheptonate exchange labeling reactions and also from the direct addition of $^{99m}$TcO$_4^-$ with $N_2P_2$ compound 4 showed similar retention times of 6.3–6.45. This indicates the formation of singular chemical species in the exchange labeling and direct labeling reactions. The probable structure of this complex is depicted through the rhenium analogue in FIG. 3.

The biodistribution of $^{99m}$Tc-$N_2P_2$ in anesthetized rats (Sprague-Dawley rats anesthetized intraperitoneally with 50 mg/kg of Na-pentobarbital) (see Table 5) at two minutes and thirty minutes post-injection (intravenous injection) showed the route of clearance is primarily into the urine via the kidneys. No evidence of in vivo dissociation of the chelate to form $^{99m}$TcO$_4^-$ is evident since the amount of $^{99m}$Tc activity found in the stomach was minimal (see Table 5). These data provide evidence that diamido-hydroxyalkyl phosphines can form $^{99m}$Tc-chelate(s) that have excellent in vitro (pH 4–11) and in vivo stability. Furthermore, the fact that a $^{99m}$Tc chelate was formed by simply mixing $^{99m}$TcO$_4^-$ with $N_2S_2$ ligand 4 in saline is evidence that this phosphine ligand is capable of reducing $^{99m}$Tc from the +7 oxidation state in pertechnetate to a lower oxidation state that is able to chelate with other $N_2P_2$ molecules present in excess.

Example 4

Formation of Complex with Rhenium:

The complex of $P_2S_2$ ligand 1 was made by the method depicted in FIG. 3 using the following procedure:

An aqueous solution (10 mL) of compound 1 (1.75 mmol) was added dropwise to an aqueous solution (50 mL) of $ReO_2(py)_4Cl$ (1.75 mmol) at 25° C. with constant stirring. The reaction mixture was heated to ~80° C. for 30 minutes as of which the reaction color changed from bright orange to light brown. The resultant reaction mixture was 80% pure by $^{31}$P NMR. The reaction mixture was concentrated in vacuo and redissolved in a small amount of DMSO. A small amount of acetonitrile was then used to precipitate the product exclusively as observed by $^{31}$P NMR. The brown precipitate was washed with ether (3×5 mL), redissolved in deionized water and allowed to evaporate slowly at room temperature to afford compound 3 as a brown, viscous oil. Low resolution FAA/MS Anal. Calcd. for $C_{11}H_{26}O_6P_2S_2Re$: 567.0204; Found: [M+H+], m/z=567.0204. Anal. Calcd. for $C_{11}H_{26}O_6P_2S_2ReCl$: C, 21.93; H, 4.35; Found: C, 22.65, H, 4.24. $^1$HNMR (D$_2$O): δ 2.36–2.52 (m, 6H, $CH_2CH_2CH_2$, $PCH_2CH_2$), 3.15–3.22 (m, 8H, $PCH_2CH_2$, $CH_2CH_2CH_2$), 4.36–4.55 (m, 8H, $PCH_2OH$). $^{13}$C NMR (D$_2$O): δ 22.1 (d, $^1J_{PC}$=33.8 Hz, $PCH_2CH_2$), 24.9 (s, $CH_2CH_2CH_2$), 33.7 (s, $PCH_2CH_2$), 34.5 (s, $CH_2CH_2CH_2$), 56.0 (d, $^1J_{PC}$=37.7 Hz, $PCH_2OH$). δ$^{31}$P NMR (D$_2$O): δ 38.6 (s).

Example 5

An 0.9% aqueous NaCl solution containing 1 mg/ml of THP a pH 7–7.4 was prepared. To 1 ml of the above solution was added $^{99m}$TcO$_4^-$ from a $^{99}$Mo/$^{99m}$Tc generator supplied by Mallinckrodt Medical International. 1 mCi $^{99m}$TcO$_4^-$ in 0.1 ml of an eluate directly from a $^{99}$Mo/$^{99m}$Tc radionuclide generator, that was used for formulation of $^{99m}$Tc-radiopharmaceuticals for human uses, supplied by Mallinckrodt Medical, Inc. After incubating one hour at room temperature, $^{99m}$Tc-THP complex was formed (i.e., $^{99m}$TcO$_2$(THP)$_4^+$) in >95% yields. This solution was then passed through an Aminopropyl-Waters-Sep-Pak-Vac containing 500 mg of the sorbent followed by washing the column with 8 ml 0.9% aqueous NaCl solutions, five times. The fraction of uncomplexed THP that was eluted through this Sep-Pak was determined by $^{31}$P NMR. The fraction of $^{99m}$Tc-THP that was found in the eluate was determined radiometrically. As a blank, the 1 mg/ml solution of THP was also passed through a column containing 500 mg of 60–200 mist silica gel. The results of this study are shown in Table 1. It was shown that >99% of the uncomplexed THP was attached to the column, presumably covalently linked to the $NH_2$-groups. Because of the relative insensitivity of the $^{31}$P NMR, the quantity or concentrations of uncoordinated THP ligands in the eluate was at the detection limit. Thus, it was possible that significantly less than 1% THP was eluted. In the blank, where the same solution was passed through a silica gel column >99% THP was found in the eluate.

It is important to recognize that formulations of $^{99m}$Tc (or $^{186/188}$Re) radiopharmaceuticals, much lower concentrations of ligands are used. In these cases, the fraction of uncomplexed THP (or HMP) functionalities that would bind to the solid matrix (via $NH_2$ groups) would be maximized. This is because the ratio of the number of $-NH_2$ groups on these columns relative to the number of HMP groups in the solvent would be much higher in radiopharmaceutical formulations than in these model studies conducted with THP.

Example 6

Experimental:

All reactions were carried out under purified nitrogen by standard Schlenk techniques. Solvents were purified by standard methods and distilled under nitrogen prior to use. $(HOH_2C)_2P(CH_2)_2S(CH_2)_3S(CH_2)_2P(CH_2OH)_2$ (1) was synthesized as previously described and used without further purification. $[ReO_2(C_5H_5N)_4]$ Cl was prepared according to literature procedure and used without further purification. (Beard et al., 1965) $Br(CH_2)_3PO(OC_2H_5)_2$ was synthesized by refluxing $P(OEt)_3$ in 10 mol excess of $Br(CH_2)_3Br$ for one hour and then purified by vacuum distillation. Nuclear magnetic resonance spectra were recorded on a Bruker ARX-300 spectrometer using $D_2O$ and $CDCl_3$ as solvents. The $^1H$ and $^{13}C$ chemical shifts are reported in ppm, downfield from internal standard $SiMe_4$. The $^{31}P$ NMR (121.5 MHz) spectra were recorded with 85% $H_3PO_4$ as an external standard and positive chemical shifts lie downfield of the standard. Elemental analyses were performed by Oneida Research Services, Inc. Whitesboro, N.Y. Mass spectral analyses were performed by the Washington University Resource for Biomedical and Bio-Organic Mass Spectrometry, St. Louis, Mo.

Synthesis of $(EtO)_2(O)PCH_2CH_2S(CH_2)_4SCH_2CH_2P(O)(OEt)_2$ (2):

A sample of 60% NaH in mineral oil (188 mmol) was placed in a 2-neck round bottom flask and charged with dry hexane (20 mL). This solution was allowed to stir ten minutes, after which the hexanemineral oil layer was removed by syringe. The flask was charged with dry tetrahydrofuran (100 mL), followed by dropwise addition of $HS(CH_2)_4SH$ (82 mmol) with constant stirring. The resulting solution was cooled at 0° C. and $BrCH_2CH_2P(O)(Oc_2H_5)_2$ (164 mmol) was added dropwise with constant stirring over a period of 30 minutes. Excess NaH was quenched by addition of 50 mL of deionized water. The solution was extracted from ethyl acetate (3×50 mL) and washed with a saturated sodium chloride solution. The organic layer was dried over anhydrous sodium sulfate. Upon filtering, the solvent was removed in vacuo to afford compound 2 in 90% yield along with a trace amount of diethyl vinylphosphonate. The compounds were separated on a silica gel column (20 cm; 60 mesh) using 90:10 ethyl acetate to hexane solvent mixture. Removal of the solvent in vacuo, afforded compound 2 as a viscous, yellow-green oil with an overall yield of 92% (36 g). Low resolution FAB/MS Anal. Calcd. for $C_{16}H_{36}O_6P_2S_2$: 450.1428. Found: $[M+H^+]$, m/z=451.2. $^1H$ NMR ($CDCl_3$): δ1.34 (t, $^3J_{HH}$=7.5 Hz, 12H, $OCH_2CH_3$), 1.70 (bs, 4H, $SCH_2C\underline{H}_2C\underline{H}_2CH_2S$), 2.03 (m, 4H, $PC\underline{H}_2CH_2$), 2.56 (bs, 4H, $SC\underline{H}_2CH_2CH_2C\underline{H}_2S$), 2.72 (m, 4H, $PCH_2C\underline{H}_2$), 4.11 (m, 8H, $OC\underline{H}_2CH_3$). $^{13}C$ NMR ($CDCl_3$): δ16.1 (d, $^3J_{PC}$=5.28 Hz, $OCH_2\underline{C}H_3$), 24.5 (d, $^2J_{PC}$=3.77 Hz, $PCH_2\underline{C}H_2$), 26.4 (d, $^1J_{PC}$=136.60 Hz, $P\underline{C}H_2CH_2$), 27.9 (s, $S\underline{C}H_2CH_2CH_2CH_2S$), 31.1 (s, $SCH_2\underline{C}H_2CH_2CH_2S$), 61.4 (d, $^2J_{PC}$=6.79 Hz, $O\underline{C}H_2CH_3$). $^{31}P$ NMR ($CDCl_3$): δ29.4(s).

Synthesis of $H_2PCH_2CH_2S(CH_2)_4SCH_2CH_2PH_2$ (3)

Compound 2 (31 mmol) was placed in 75 mL of dry diethyl ether and cooled to 0° C. An ether solution of 1.0M lithium aluminum hydride (78 mmol, 78 mL) was slowly added dropwise to this solution with constant stirring. An aqueous solution of 6N hydrochloric acid (50 mL) was added dropwise to the solution to quench any remaining $LiAlH_4$. The ether layer was separated by cannula and the solvent was removed in vacuo to afford compound 3 in 92% yield (7.8 g) as a colorless, viscous oil. $^1H$ NMR ($CDCl_3$): δ1.68 (m, 4H, $PC\underline{H}_2CH_2$), 1.76 (m, 4H, $SCH_2C\underline{H}_2C\underline{H}_2CH_2S$), 2.54 (m, 4H, $SC\underline{H}_2CH_2CH_2C\underline{H}_2S$), 2.68 (m, 4H, $PCH_2C\underline{H}_2$), 2.75 (dt, $^1J_{PH}$=1.95 1 Hz, $P\underline{H}_2$). $^{13}C$ NMR ($CDCl_3$): δ14.5 (d, $^1J_{PC}$=10.57 Hz, $P\underline{C}H_2CH_2$) 28.1 (s, $SCH_2\underline{C}H_2\underline{C}H_2CH_2$), 31.0 (s, $S\underline{C}H_2CH_2CH_2\underline{C}H_2S$), 34.7 (d, $^2J_{PC}$=1.51 Hz, $PCH_2\underline{C}H_2$). $^{31}P$ NMR ($CDCl_3$): δ—136.8 (s).

Synthesis of $(HOH_2C)_2PCH_2CH_2S(CH_2)_4SCH_2CH_2P(CH_2OH)_2$ (4)

Aqueous formaldehyde (124 mmol) was placed in 50 mL of oxygen free ethanol and purged with nitrogen gas for two hours at 25° C. Compound 3 (29 mmol) was added dropwise to the solution via syringe with constant stirring at 25° C. The reaction was complete in one hour, as monitored by $^{31}P$ NMR spectroscopy. Removal of the solvent in vacuo afforded compound 4 in 93% yield (10.5 g) as a colorless, viscous oil. Low resolution FAB/MS Anal. Calcd. for $C_{12}H_{28}O_4P_2S_2$: 362.1 Found: $[M+H^+]$, m/z=395.1. $^{31}P$ NMR ($D_2O$): δ-25.5 (s). For characterization purposes, the hydroxymethyl phosphine compound 4 was converted to its corresponding phosphonium chloride salt by addition of 3N HCl. The reaction mixture was concentrated in vacuo and loaded onto a Water's Sep-Pak 35 cc (10 g) C18 cartridge. The pure phosphonium salt was isolated as a clear, viscous oil. $^1H$ NMR ($D_2O$): δ1.54 (m, 4H, $SCH_2C\underline{H}_2C\underline{H}_2CH_2S$), 2.52 (m, 4H, $PC\underline{H}_2CH_2$), 2.59 (m, 4H, $PCH_2C\underline{H}_2$), 4.53 (m, 12H, $PC\underline{H}_2OH$). $^{13}C$ NMR ($D_2O$): δ14.9 (d, $^1J_{PC}$=37.73 Hz, $P\underline{C}H_2CH_2$), 22.7 (d, $^2J_{PC}$=5.28 Hz, $PCH_2\underline{C}H_2$), 27.2 (s, $SCH_2\underline{C}H_2\underline{C}H_2CH_2S$), 30.2 (s, $S\underline{C}H_2CH_2CH_2\underline{C}H_2S$), 50.3 (d, $^1J_{PC}$=52.83 Hz, $P\underline{C}H_2OH$). $^{31}P$ NMR ($D_2O$): δ28.3 (s).

Synthesis of $(EtO)_2(O)PCH_2CH_2CH_2S(CH_2)_3SCH_2CH_2CH_2P(O)(OEt)_2$ (5)

A sample of 60% NaH in mineral oil (184 mmol) was placed in a 2-neck round bottom flask and charged with dry hexane (20 mL). This solution was allowed to stir 10 minutes, after which the hexane-mineral oil layer was removed by syringe. The flask was charged with dry tetrahydrofuran (100 mL), followed by dropwise addition of $HS(CH_2)_3SH$ (92 mmol) with constant stirring. The resulting solution was cooled at 0° C. and $BrCH_2CH_2CH_2P(O)(OC_2H_5)_2$ (184 mmol) was added dropwise with constant stirring over a period of 30 minutes. Excess NaH was quenched by addition of 50 mL of deionized water. The solution was extracted from ethyl acetate (3×50 mL) and washed with a saturated sodium chloride solution. The organic layer was dried over anhydrous sodium sulfate. The final product was purified on a silica gel column (20 cm; 60 mesh) using 90:10 ethyl acetate to hexane solvent mixture. Removal of the solvent in vacuo, afforded compound 5 as a viscous, yellow-green oil with an overall yield of 88% (38 g). Low resolution FAB/MS Anal. Calcd. for $C_{17}H_{38}O_6P_2S_2$: 464.2 Found: $[M+M^+]$, mz=465.2. $^1H$ NMR ($CDCl_3$): δ1.25 (t, $^3J_{HH}$=9.0 Hz, $OCH_2C\underline{H}_3$), 1.80 (m, 10H, $PCH_2C\underline{H}_2CH_2$, $PCH_2CH_2C\underline{H}_2$, $SCH_2C\underline{H}_2CH_2S$), 2.53 (m, 8H, $PC\underline{H}_2C\underline{H}_2CH_2$ $SC\underline{H}_2CH_2C\underline{H}_2S$), 4.01 (m, 8H, $OC\underline{H}_2CH_3$). $^{13}C$ NMR ($CDCl_3$): δ15.9 (d, $^3J_{PC}$=5.28 Hz, $OCH_2\underline{C}H_3$), 21.9 (d, $^3J_{PC}$4.52 Hz, $PCH_2CH_2\underline{C}H_2$), 23.9 (d, $^1J_{PC}$=141.88 Hz, $P\underline{C}H_2CH_2CH_2$), 28.6 (s, $SCH_2\underline{C}H_2CH_2S$), 29.9 (s, $S\underline{C}H_2CH_2\underline{C}H_2S$), 31.8 (d, $^2J_{PC}$=17.34 Hz, $PCH_2\underline{C}H_2CH_2$), 60.9 (d, $^2J_{PC}$6.03 Hz, $O\underline{C}H_2CH_3$). $^{31}P$ NMR ($CDCl_3$): δ31.8 (s).

Synthesis of $H_2PCH_2CH_2CH_2S(CH_2)_3SCH_2CH_2CH_2PH_2$ (6)

Compound 5 (32 mmol) was placed in 75 mL of dry diethyl ether and cooled to 0° C. An ether solution of 1.0M lithium aluminum hydride (80 mmol, 80 mL) was slowly added dropwise to this solution with constant stirring. An aqueous solution of 6N hydrochloric acid (50 mL) was added dropwise to the solution to quench any remaining LiAlH$_4$. The ether layer was separated by cannula and the solvent was removed in vacuo to afford compound 6 in 94% yield (7.8 g) as a colorless, viscous oil. $^1$H NMR (CDCl$_3$): δ1.59 (m, 4H, PC$\underline{H}_2$CH$_2$CH$_2$), 1.81 (m, 6H, SCH$_2$C$\underline{H}_2$CH$_2$, SC$\underline{H}_2$CH$_2$CH$_2$S, 2.58 (m, 8H, PCH$_2$C$\underline{H}_2$CH$_2$, PCH$_2$CH$_2$C$\underline{H}_2$) 2.69 (dt, $^1J_{PC}$=192.1 Hz, P$\underline{H}_2$. $^{13}$C NMR (CDCl$_3$): δ12.9 (d, $^1J_{PC}$=9.06 Hz, P$\underline{C}$H$_2$CH$_2$CH$_2$), 29.2 (s, SCH$_2$$\underline{C}$H$_2$CH$_2$S), 30.7 (s, S$\underline{C}$H$_2$CH$_2$$\underline{C}$H$_2$S), 32.5 (d, $^2J_{PC}$=6.04 Hz, PCH$_2$$\underline{C}$H$_2$CH$_2$), 32.6 (d, $^3J_{PC}$=3.02 Hz, PCH$_2$CH$_2$$\underline{C}$H$_2$). $^{31}$P NMR (CDCl$_3$): δ−137.5.

Synthesis of $(HOH_2C)_2PCH_2CH_2CH_2S(CH_2)_3SCH_2CH_2CH_2P(CH_2OH)_2$ (7)

Aqueous formaldehyde (131 mmol) was placed in 50 mL of oxygen free ethanol and purged with nitrogen gas for two hours at 25° C. Compound 6 (30 mmol) was added dropwise to the solution via syringe with constant stirring at 25° C. The reaction was complete in one hour, as monitored by $^{31}$P NMR spectroscopy. Removal of the solvent in vacuo afforded compound 7 in 95% yield (10.9 g) as a colorless, viscous oil. Low resolution FAB/MS Anal. Calcd. for C$_{13}$H$_{30}$O$_4$P$_2$S$_2$: 376.1 Found: [M+H$^+$], m/z=409.1. $^{31}$P NMR (D$_2$O): δ−25.6 (s). For characterization purposes, the hydroxymethyl phosphine compound 7 was converted to its corresponding phosphonium chloride salt by addition of 3N HCl. The reaction mixture was concentrated in vacua and loaded onto a Water's Sep-Pak 35 cc (10 g) C18 cartridge. The pure phosphonium salt was isolated as a clear, viscous oil. $^1$H NMR (D$_2$O): δ1.78 (m, 2H, SCH$_2$C$\underline{H}_2$CH$_2$S), 1.94 (m, 4H, PC$\underline{H}_2$CH$_2$CH$_2$), 2.41 (m, 4H, PCH$_2$CH$_2$C$\underline{H}_2$), 2.63 (m, 8H, PCH$_2$C$\underline{H}_2$CH$_2$ SC$\underline{H}_2$CH$_2$C$\underline{H}_2$), 4.60 (m, 12H, PC$\underline{H}_2$OH). $^{13}$C NMR D$_2$O): δ13.2 (d, $^1J_{PC}$=40.75 Hz, P$\underline{C}$H$_2$CH$_2$CH$_2$), 21.5 (d, $^3J_{PC}$=4.5 Hz, PCH$_2$CH$_2$$\underline{C}$H$_2$), 29.1 (s, SCH$_2$$\underline{C}$H$_2$CH$_2$S), 30.2 (s, S$\underline{C}$H$_2$CH$_2$$\underline{C}$H$_2$S, 32.2 (d, $^2J_{PC}$=15.85 Hz, PCH$_2$$\underline{C}$H$_2$CH$_2$), 50.6 (d, $^1J_{PC}$=54.34 Hz, P$\underline{C}$H$_2$OH). $^{31}$P NMR (D$_2$O): δ28.8 (s).

Synthesis of $[ReO_2(HOH_2C)_2P(CH_2)_2S(CH_2)_3S(CH_2)_2P(CH_2OH)_2]_2Cl_2$=(8)

An aqueous solution (10 mL) of (HOH$_2$C)$_2$P(CH$_2$)$_2$S(CH$_2$)$_3$S(CH$_2$)$_2$P(CH$_2$OH)$_2$ (1.8 mmol) was added dropwise to an aqueous solution (50 mL) of ReO$_2$(C$_5$H$_5$N)$_4$Cl (1.7 mmol) at 25° C. with constant stirring. The reaction mixture was heated to ~80° C. for 30 minutes as of which the reaction color changed from bright orange to light brown. The reaction mixture was concentrated in vacuo and loaded onto a Water's Sep-Pak Vac 35 cc (10 g) C18 cartridge. The pure reaction product was isolated as a green microcrystalline solid. The product was reconstituted in methanol/diethyl ether (4:1) and allowed to evaporate slowly at room temperature to afford compound 8 as a green crystalline solid in 84% yield (1.72 g). Anal. Calcd. For C$_{22}$H$_{52}$O$_{12}$P$_4$S$_4$Re$_2$Cl$_2$: C, 21.93; H, 4.35. Found: C, 22.65; H, 4.24. $^1$H NMR (D$_2$O): δ2.44 (m, 12H, SCH$_2$C$\underline{H}_2$CH$_2$S, PC$\underline{H}_2$CH$_2$), 3.19 (m, 16H, PCH$_2$C$\underline{H}_2$, SC$\underline{H}_2$CH$_2$C$\underline{H}_2$S), 4.46 (m, 16H, PC$\underline{H}_2$OH). $^{13}$C NMR (D$_2$O): δ22.1 (d, $^1J_{PC}$=33.8 Hz, P$\underline{C}$H$_2$CH$_2$), 24.9 (s, CH$_2$$\underline{C}$H$_2$CH$_2$), 33.7 (s, PCH$_2$$\underline{C}$H$_2$), 34.5 (s, S$\underline{C}$H$_2$CH$_2$$\underline{C}$H$_2$S), 56.0 (d, $^1J_{PC}$=37.7 Hz, P$\underline{C}$H$_2$OH). $^{31}$P NMR (D$_2$O): δ38.6 (s).

Synthesis of $[ReO_2(HOH_2C)_2P(CH_2)_2S(CH_2)_4S(CH_2)_2P(CH_2OH_2]_2(ReO_4^-)_2$ (9)

A solid sample of (HOH$_2$C)$_2$P(CH$_2$)$_2$S(CH$_2$)$_4$S(CH$_2$)$_2$P(CH$_2$OH)$_2$ (1.32 mmol) was added to an aqueous solution (50 mL) of ReO$_2$ (C$_5$H$_5$N)$_4$Cl (1.2 mmol) at 25° C. with constant stirring. The reaction mixture was heated to ~80° C. for 30 minutes as of which the reaction color changed from bright orange to light brown. The reaction mixture was concentrated in vacuo and loaded onto a Water's Sep-Pak Vac 35 cc (10 g) C18 cartridge. The pure reaction was isolated as a green microcrystalline solid. The product was reconstituted in water/methanol (4:1) and allowed to evaporate slowly at room temperature to afford compound 9 as a green microcrystalline solid in 40% yield (0.8 g). Anal. Calcd. For C$_{24}$H$_{56}$O$_{20}$P$_4$S$_4$Re$_4$: C, 17.35; H, 3.40. Found: C, 17.34; H, 3.31. $^1$H NMR (D$_2$O): δ2.05 (bs, 8H, PC$\underline{H}_2$CH$_2$), 2.42 (m, 8H, SCH$_2$C$\underline{H}_2$C$\underline{H}_2$CH$_2$S), 3.05 (m, 16H, PCH$_2$C$\underline{H}_2$, SC$\underline{H}_2$CH$_2$CH$_2$C$\underline{H}_2$S), 4.41 (m, 16H, PCH$_2$OH). $^{13}$C NMR D$_2$O) δ21.9 (d, $^1J_{PC}$=33.96 Hz, P$\underline{C}$H$_2$CH$_2$), 26.2 (s, SCH$_2$$\underline{C}$H$_2$$\underline{C}$H$_2$CH$_2$S), 34.5 (s, PCH$_2$$\underline{C}$H$_2$), 37.0 (s, S$\underline{C}$H$_2$CH$_2$CH$_2$$\underline{C}$H$_2$S), 55.9 (d, $^1J_{PC}$=37.73 Hz, P$\underline{C}$H$_2$OH). $^{31}$P NMR (D$_2$O): δ37.5 (s).

Synthesis of $[ReO_2(HOH_2C)_2P(CH_2)_3S(CH_2)_3S(CH_2)_3P(CH_2OH)_2]Cl$ (10)

An aqueous solution (10 mL) of (HOH$_2$C)$_2$P(CH$_2$)$_2$S(CH$_2$)$_4$S(CH$_2$)$_2$P(CH$_2$OH) (1.06 mmol) was added dropwise to an aqueous solution (50 mL) of ReO$_2$(C$_5$H$_5$N)$_4$Cl (0.926 mmol) at 25° C. with constant stirring. The reaction mixture was heated to ~80° C. for 30 minutes as of which the reaction color changed from bright orange to light brown. The reaction mixture was concentrated in vacuo and loaded onto a Water's Sep-Pak Vac 35 cc (10 g) C18 cartridge. The pure reaction product was isolated as a green microcrystalline solid. The product was reconstituted in methanol/diethyl ether (4:1) and allowed to evaporate slowly at room temperature to afford compound 10 as a green microcrystalline solid in 80% yield (0.47 g). Anal. Calcd. For C$_{13}$H$_{30}$O$_6$P$_2$S$_2$ReCl: C, 24.76; H, 4.80. Found: C, 24.77; H, 4.73. $^1$H NMR (D$_2$O): δ2.53 (m, 10H, PC$\underline{H}_2$CH$_2$CH$_2$ PCH$_2$C$\underline{H}_2$CH$_2$, SCH$_2$C$\underline{H}_2$CH$_2$S, 3.18 (bs, 4H, PCH$_2$CH$_2$C$\underline{H}_2$), 3.47 (m, 4H, SC$\underline{H}_2$CH$_2$C$\underline{H}_2$), 4.43 (m, 8H, PC$\underline{H}_2$OH). $^{13}$C NMR (D$_2$O) δ17.5 (d, $^1J_{PC}$=37.74 Hz, P$\underline{C}$H$_2$CH$_2$CH$_2$), 20.4 ( PCH$_2$$\underline{C}$H$_2$CH$_2$), 23.6 (s, SCH$_2$$\underline{C}$H$_2$CH$_2$S), 36.3. (s, PCH$_2$CH$_2$$\underline{C}$H$_2$), 37.0 (s, S$\underline{C}$H$_2$C H$_2$$\underline{C}$H$_2$S), 58.3 (d, $^1J_{PC}$=37.74 Hz, P$\underline{C}$H$_2$OH). $^{31}$P NMR (D$_2$O): δ−8.56 (s).

HPLC Analysis of Complexes 8, 9, and 10

All of the complexes 8, 9, and 10 were dissolved in deionized water and prefiltered through a 0.22 μm Cameo syringe filter. High performance liquid chromatography (HPLC) analysis was performed using an analytical PRP-1 column (Hamilton poly(styrene-divinylbenzene), 100Å). The mobile phase consisted of a gradient system with solvent A corresponding to water with 0.1% trifluoroacetic acid and solvent B corresponding to acetonitrile with 0.1% trifluoroacetic acid. The mobile phase started with 100% A for two minutes followed by a linear gradient from 0% B to 100% B from two to seven minutes. The gradient remained at 100% B for an additional two minutes before being ramped to 0% B at time 20 minutes for column equilibration. The flow rate of the mobile phase was 1.5 mL/min. The chart speed of the integrator was 0.5 cm/min. Detection was accomplished using an in-line Waters 486 Tunable Absorbance Detector preset to 380 nm.

X-ray Data Collection and Processing

The crystal data and the details of data collection for complexes 8, 9, and 10 are listed in Tables 6–12. Clear, yellowish green crystals of complexes 8, 9, and 10 suitable for X-ray diffraction were obtained by slow evaporation from the appropriate solvent systems as described in the experimental section. Intensity data were collected on a Siemens SMART CDD system using the omega scan mode. Data were corrected for absorption using the program SAD-ABS which is based on the method of Blessing. (Blessing, 1995) Crystal decay was less than one percent and a correction deemed unnecessary. The structures were solved by direct methods using SHELXS-86 and refined by the full-matrix least square method on $F^2$ using SHELXL-93. (Sheldrick, 1990, Sheldrick, 1993).

For compound 8, all non-hydrogen atoms, with the exception of the lattice water oxygen atom, were refined anisotropically. Ethylenic hydrogen atoms were placed in calculated positions with their thermal parameters fixed at values of 1.2 those of their parent atoms. The hydroxyl hydrogen atoms were located in difference Fourier maps and refined with their O—H distances constrained to 1.0±0.–0.02 Å and with independent isotropic thermal parameters. The water hydrogen atoms were similarly located and refined with O—H distances constrained to 1.0±0.02Å and the H—H distance to 1.62±0.02Å (the hydrogen thermal parameters were fixed at a value of 1.2 times that of their parent oxygen atom).

For compound 9, all non-hydrogen atoms, with the exception of the perrhenate oxygen atoms, were refined anisotropically. Ethylenic and hydroxyl hydrogen atoms were placed in calculated positions with their thermal parameters fixed at values of 1.2 times those of their parent atoms. The hydroxyl hydrogen atoms were placed by modeling the hydroxyl ski moieties as rigid groups, maximizing the electron density at the calculated hydrogen positions. The oxygen atoms of both of the perrhenate anions were disordered and the Re-O distances were restrained to 1.71 (2)Å. (Orpen et al., 1989). In addition, all of the perrhenate O—O distances were restrained to 2.79 (2)Å in order to impart tetrahedral geometry to the anions, and, the oxygen atoms were assigned a common isotropic thermal parameter.

For compound 10, all non-hydrogen atoms were refined anisotropically and C—H hydrogen atoms were placed in calculated positions. Hydroxyl hydrogen atoms belonging to the ligand were located in difference electron density maps and refined with their O—H distances restrained to 1.0±0.01Å. For hydrogen atoms placed in calculated positions, all isotropic thermal parameters were fixed at values of 1.2 those of their parent atoms. The methanolic hydroxyl hydrogen atom was not located and thus omitted from the structure refinement.

Other pertinent details relating to data collection, structure solution, and refinement are given in Tables 6–12.

In Vitro Stability Studies of Complexes 8, 9, and 10

Appropriate sample sizes of complexes 8, 9, and 10 were dissolved in 10 mL of deionized water to afford solution concentrations of ~0.01M. To these solutions was added 15 mL of a 1.0M cysteine solution also in water. The solutions were allowed to stir at room temperature overnight. The reaction progress for potential ligand displacement was monitored by $^{31}$P NMR spectroscopy at various timepoints over a twenty-four hour study period.

Results and Discussion

Figure 10:
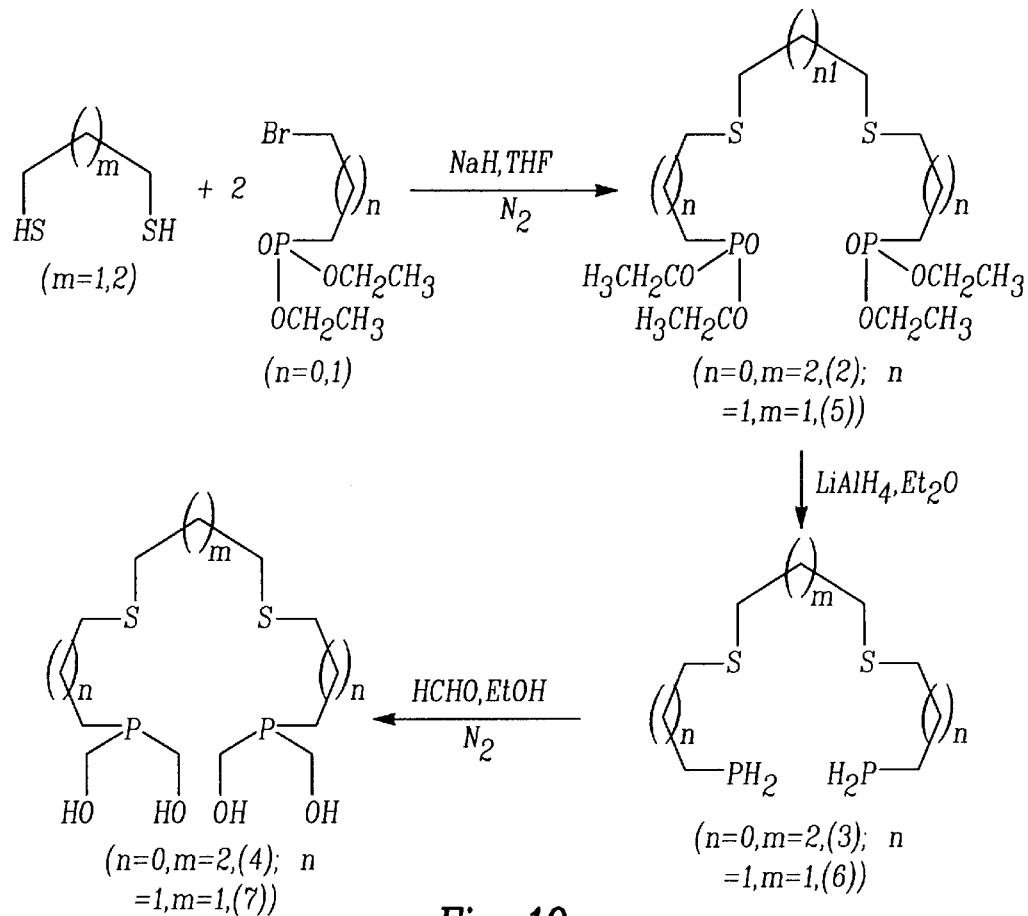
FIG. 10 illustrates a synthesis scheme for the synthesis of a dithio-diphosphine of the general formula $P_2S_2$ in accordance with the present invention.

The synthesis of the thioether-functionalized bisphosphines 1, 4, and 7 was accomplished in a two step procedure as shown in Scheme 1 of FIG. 10. Compound 1 was synthesized as previously reported and used without further purification. The thioether-functionalized bisphosphonates $(EtO)_2(O)PCH_2CH_2S(CH_2)_4SCH_2CH_2P(O)(OEt)_2$ (2) and $(Eto)_2(O)PCH_2CH_2CH_2S(CH_2)_3SCH_2CH_2CH_2P(O)(OEt)_2$ (5) were prepared via the reaction of the dithiols $HS(CH_2)_4$ SH and $HS(CH_2)_3SH$ with the appropriate phosphonate precursors $BrCH_2CH_2P(O)(OEt)_2$ and is $BrCH_2CH_2CH_2P(O)(OEt)_2$ in the presence of NaH in freshly distilled THF. The phosphine hydrides $H_2PCH_2CH_2S(CH_2)_4SCH_2CH_2PH_2$ (3) and $H_2PCH_2CH_2CH_2S(CH_2)_3SCH_2CH_2CH_2PH_2$ (6) were prepared by reduction of the bisphosphonates 2 and 5 in diethyl ether using lithium aluminum hydride. The hydroxymethyl phosphine ligands 4 and 7 were prepared by formylation of the P—H bonds of 2 and 5 in oxygen-free ethanol in the presence of aqueous formaldehyde.

The new compounds 2–7 were characterized by $^1$H, $^{13}$C, and $^{31}$P NMR spectroscopy. For characterization purposes, compounds 4 and 7 were converted to their corresponding phosphonium salts in the presence of excess formaldehyde and 3N HCl as shown in Equation 1.

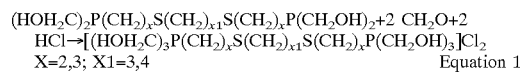

$(HOH_2C)_2P(CH_2)_xS(CH_2)_{x1}S(CH_2)_xP(CH_2OH)_2 + 2\ CH_2O + 2\ HCl \rightarrow [(HOH_2C)_3P(CH_2)_xS(CH_2)_{x1}S(CH_2)_xP(CH_2OH)_3]Cl_2$
X=2,3; X1=3,4                                  Equation 1

FAB mass spectrometry was used to identify the molecular ions for all of the compounds excluding the bisphosphine hydrides 3 and 6. Parent ions at [M+H$^+$], m/z=451.2 and [M+H$^+$], m/z=465.2 were observed for the bisphosphonate compounds 2 and 5 respectively. Compounds 2 and 5 resonated as singlet signals at 29.4 and 31.8 in the $^{31}$P NMR spectrum. The formation of the thioether-functionalized bisphosphine hydrides 3 and 6 from their corresponding bisphosphonates 2 and 5 was monitored by $^{31}$P NMR spectroscopy. The phosphine hydrides 3 and 6 resonated as singlet signals in the $^{31}$P NMR spectrum at –136.8 and –137.5 ppm, respectively. The new hydroxymethyl phosphine ligands 4 and 7 show parent ions at [M+H$^+$], m/z= 395.1 and [M+H$^+$], m/z=409.1, corresponding to the phosphine oxides, respectively. Each of the dithio-bisphosphine ligands resonated as singlet signals in the $^{31}$P NMR spectrum at –25.5 and –25.6 ppm, respectively.

The water solubility of ligands 1, 4, and 7 necessitated the development of their coordination chemistry in aqueous media. Compound 1, in water, upon interaction with [ReO$_2$(C$_5$H$_5$N)$_4$Cl, in refluxing water, produced the diatonic complex [ReO$_2$(HOH$_2$C)$_2$P(CH$_2$)$_2$S(CH$_2$)$_3$S(CH$_2$)$_2$P(CH$_2$OH)$_2$]$_2$Cl$_2$ (8) in 84% yield as shown in FIG. 3. The total reaction time was ~30 minutes. The chemical constituency of complex 8 was verified by $^1$H, $^{13}$C, and $^{31}$P NMR spectroscopies as well as elemental analyses. Compound 8 resonated as a singlet signal at 38.6 ppm in the $^{31}$P NMR spectrum.

Compound 4, in water, upon interaction with [ReO$_2$(C$_5$H$_5$N)$_4$]Cl, in refluxing water, produced the dicationic complex [ReO$_2$(HOH$_2$C)$_2$P(CH$_2$)$_2$S(CH$_2$)$_4$S(CH$_2$)$_2$P(CH$_2$OH)$_2$]$_2$Cl$_2$ (9) in 40% yield as shown in FIG. 3. The total reaction time was ~30 minutes. The chemical constituency of complex 9 was verified by $^1$H, $^{13}$C, and $^{31}$P NMR spectroscopies as well as elemental analyses. Compound 9 resonated as a singlet signal at 37.5 ppm in the $^{31}$P NMR spectrum.

Compound 7, in water, upon interaction with [ReO$_2$(C$_5$H$_5$N)4]Cl, in refluxing water, produced the cationic complex [ReO$_2$(HOH$_2$C)$_2$P(CH$_2$)$_3$S(CH$_2$)$_3$S(CH$_2$)$_3$P(CH$_2$OH)$_2$]Cl (10) in 80% yield. The total reaction time was ~30 minutes. The chemical constitution of complex 10 was confirmed by $^1$H, $^{13}$C, and $^{31}$P NMR spectroscopies and elemental analyses. Compound 10 resonated at –8.6 ppm in the $^{31}$P NMR spectrum.

All of the complexes 8, 9, and 10 were analyzed by HPLC in order to further establish the purity of the complexes.

Figure 5A:
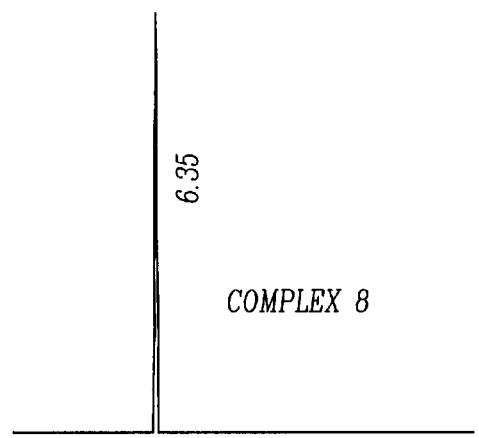
FIGS. 5a–c are graphs which represent HPLC analyses of (a) complex 8, (b) complex 9, and (c) complex 10.
Figure 5B:
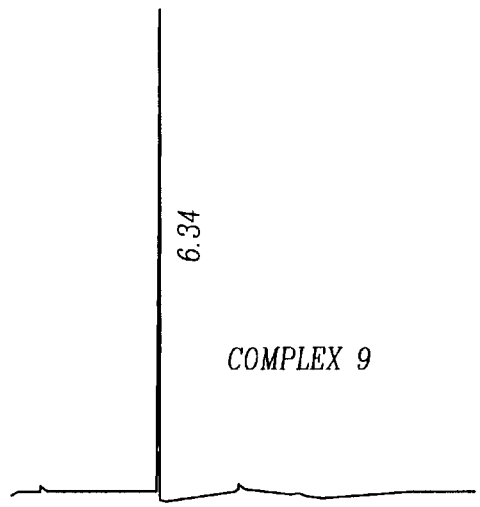
Figure 5C:
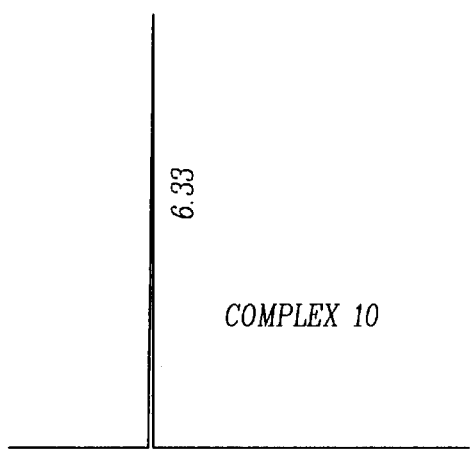

Each of the complexes eluted as a singular species, demonstrating ~98% purity as shown in FIGS. 5a–c.

X-ray Crystallographic Investigations of compounds 8, 9 and 10

Figure 7:
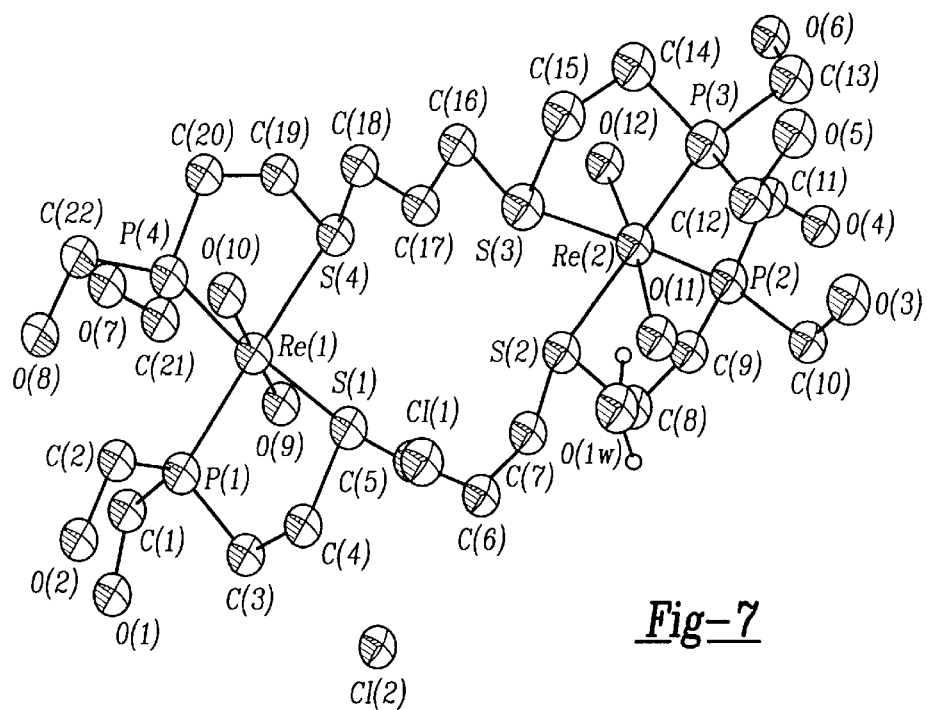
FIG. 7 is and ORTEP drawing of complex 8 showing a 50% probability ellipsoids.

X-ray crystallographic analysis of compound 8 enabled applicants to further determine the molecular composition of this compound. Slow evaporation of a methanol/diethyl ether (4:1) solution of compound 8 produced single crystals suitable for X-ray crystallographic analysis. An ORTEP diagram of compound 8 is shown in FIG. 7. Selected bond distances and bond angles are listed in Table 7. The unit cell consists of four independent molecules each containing one water of crystallization. There are no unusual inter- or intra-molecular interactions. The geometry around the rhenium centers is octahedral. The structure reveals a bimetallic complex with two independent, coordinating, ligands. As revealed by the structure, one phosphorus and one sulfur of each ligand is coordinated to the metal center in a chelating fashion, while the other phosphorus and sulfur of the same ligand is coordinated to the other metal center in a cis arrangement via two five-membered $PCH_2CH_2SRe(V)$ metallocycles, respectively. The two oxygen atoms of the dioxorhenium center are essentially trans to one another. The Re1- P1 and Re1-P4 distances are 2.4110(9) and 2.4052(10) Å, respectively. The Re2- P2 and Re2-P3 distances are 2.3962(10) and 2.4004(9)Å, respectively. The Re1-S1 and Re1- S4 distances are 2.5337(9) and 2.5543(9)Å, respectively. The Re2- S2 and Re2- S3 distances are 2.5343(9) and 2.5804(10)Å, respectively. The average P—Re—P bond angle is 100.01°. The average S—Re—S bond angle is 95.93°. The average of the four P—Re—S bond angles is 82.09°, respectively.

Figure 8:
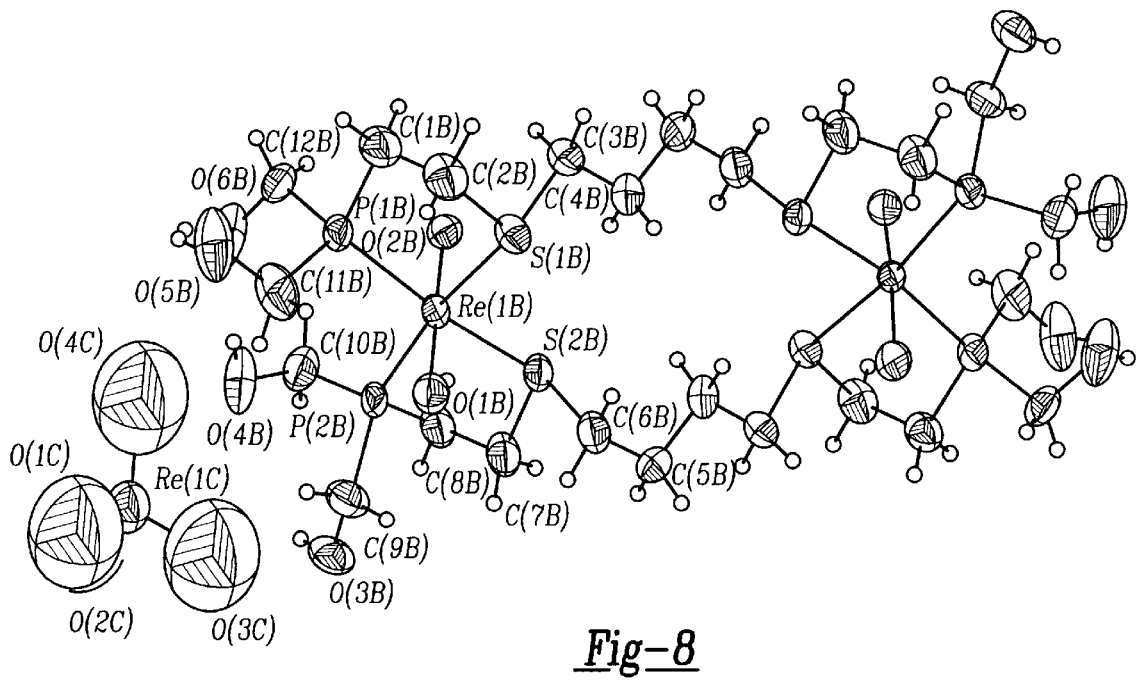
FIG. 8 is and ORTEP drawing of complex 9 showing a 50% probability ellipsoids.

Slow evaporation of water/methanol (4:1) from a solution of compound 9 afforded quality crystals suitable for X-ray crystallographic studies. An ORTEP diagram of compound 9 is shown in FIG. 8. Selected bond distances and bond angles are listed in Table 8. The unit cell consists of two independent molecules. There are no unusual inter- or intra-molecular interactions. The geometry about the rhenium centers is octahedral. As with complex 8, the structure of complex 9 reveals a bimetallic complex with two independent, coordinating, ligands. However, the counterions of complex 9 are distorted perrhenate anions. The octahedral geometry around the metal centers is further defined by coordination of on set of $P^{III}$ and S from two different ligands in a cis arrangement to produced a bimetallic Re(V) complex with four $PCH_2CH_2SRe(V)$ five-membered metallocycles. The two oxygen atoms of the dioxorhenium center are essentially trans to one another. The Re1a- P1a and Re1a- P2a distances are 2.414 and 2.410Å, respectively. The Re1b- P1b and Re1b- P2b distances are 2.405 and 2.421Å, respectively. The Re1a- S1a and Re1a-S2a distances are 2.515 and 2.536Å, respectively. The Re1b-S1b and Re1b- S2b distances are 2.538 and 2.510 Å, respectively. The average P—Re—P bond angle is 101.17°. The average S—Re—S bond angle is 95.11°. The average of the four P—Re—S bond angles is 82.20°, respectively.

Figure 9:
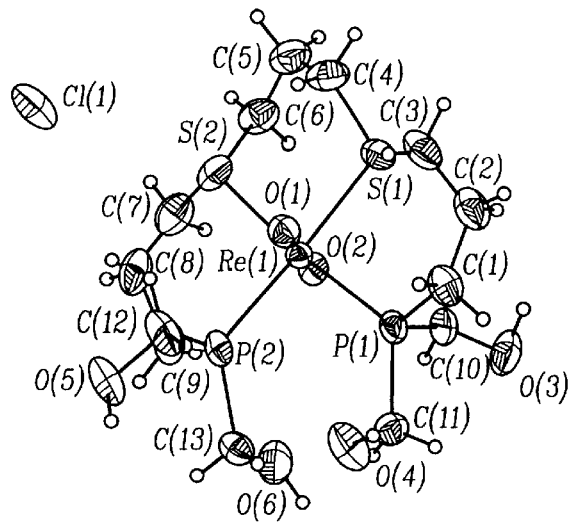
FIG. 9 is and ORTEP drawing of complex 10 showing a 50% probability ellipsoids.

The molecular structure of compound 10 was also confirmed by X-ray crystallographic analysis. An ORTEP diagram of compound 10 is shown in FIG. 9, and the selected bond distances and bond angles are listed in Table 9. The unit cell consists of four independent molecules each containing one methanol of crystallization. There are no unusual inter- or intra-molecular interactions. As revealed by the structure, compound 10 is a monometallic-monoligated complex. The geometry around the rhenium center is octahedral with the metal flapped across $P^{III}$ and S in a cis arrangement to produce two six-membered metallocycles. As revealed by the structure, the two oxygen atoms of the dioxorhenium center are essentially trans to one another. The Re- P1 and Re P2 distances are 2.4248(10) and 2.4176Å, respectively. The Re- S1 and Re- S2 distances are 2.5503 (10) and 2.5323(10)Å, respectively. The P—Re—P bond angle is 100.84°(3). The S—Re—S bond angle is 88.10°(4). The P1- Re- S1 and P2- Re- S2 bond angles are 84.07°(3) and 87.02°(4), respectively.

Conformation of Rings in Rhenium (V) Complexes Derived from 232, 242, (Compounds 8 and 9) and 333 (Compound 10) Dithiobisphosphine Backbones In all of the three structures of compounds 8–10, it may be somewhat misleading to describe the ring conformations using the traditional "chair", "boat", and "envelope" terminology owing to the large differences in the bond lengths between the atoms making up the rings. For each ring in compounds 8, 9, and 10, the displacement of the carbon atoms form the plane through the ring's S, Re, and P atoms have been calculated. (Nardelli, 1983). This plane can be considered to be a rigid reference for each ring by virtue of the near planar coordination of the sulfur and phosphorus atoms about the metal center while the constraints on the S—C, C—C and P—C bonds give rise to ring distortion.

In the complex 8, each of the four unique five-membered rings Re1-P1-C3-C4-S1, Re1-P4-C20-C19-S4, Re2-P3-C14-C15-S3, and Re2-P2-C9-C8-S2 can be described as envelopes with flaps derived from C3–C4, C19–C20, C8–C9, and C14–C15, respectively. Each of the four rings are in the same molecule of the asymmetric unit.

The structure of the 242 $S_2P_2$ Re complex 9 has four unique five-membered rings, two each in the half-molecules, constituting the asymmetric unit. The conformation of rings in complex 9 are essentially similar to those described for complex 8 except that the ring four (4), consisting of Re1b-P2b-C8b-C7b-S2b, may best be described as a twisted envelope (therefore no flap).

The three six-membered rings in complex 10, Re1-P1-C1-C2-C3 , Re1-S1-C4-C5-C6-S2 , and Re1-S2-C7-C8-C9-P2 , are in the distorted chair, severely-twisted chair, and distorted chair conformations, respectively.

In Vitro Stability Studies of complexes of compounds 8, 9, and 10

Figure 6:
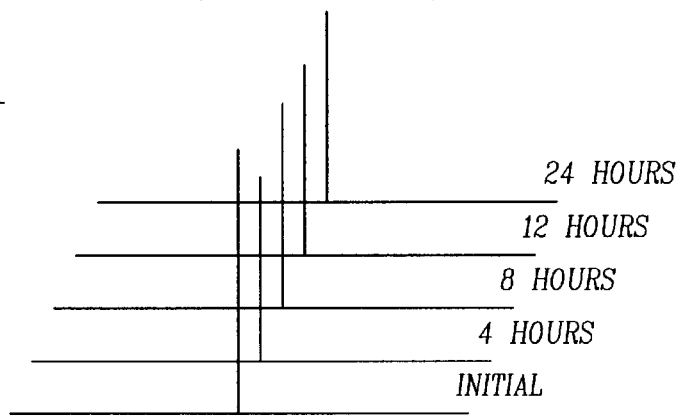
FIG. 6 is a graph illustrating stability profiles of complex 10 in a 1.0M cysteine solution over a twenty four hour time period.

In order to determine the in vitro stability of the rhenium $S_2P_2$ complexes 8, 9, and 10, the solutions of each were allowed to incubate at 25° C. in an aqueous solution of cysteine. Typically, compounds 8–10 (~0.01M) were allowed to interact with a 1M cysteine solution. $^{31}P$ NMR Spectroscopic data of aliquots of each sample, taken at different time intervals, indicated no observable ligand exchange or complex decomposition. $^{31}P$ NMR spectra of complex 10 over a twenty-four hour time period, as shown in FIG. 6, demonstrated the unusual kinetic inertness of this class of Re(V), water-soluble complexes.

Conclusions

Figure 11:
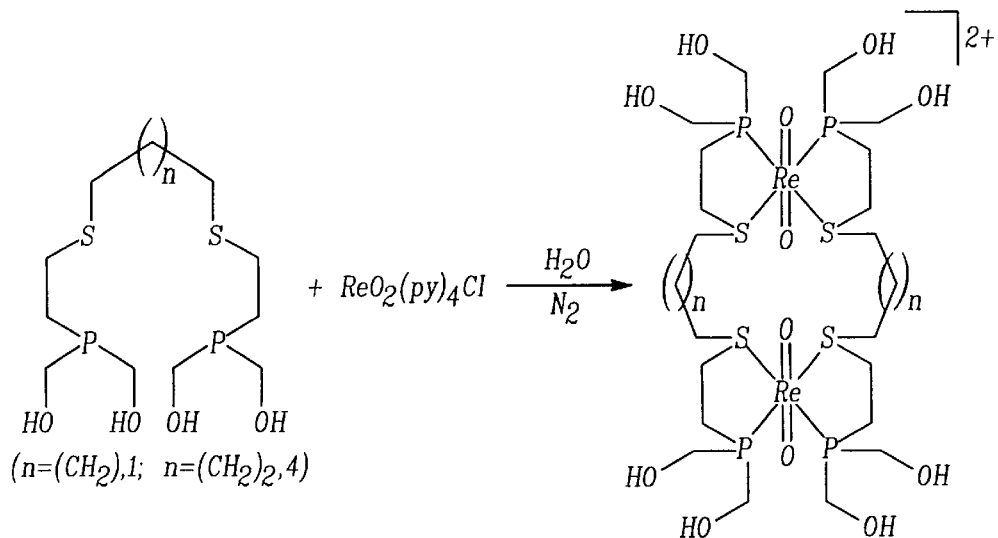
FIG. 11 illustrates a synthesis scheme for the synthesis of regio- and stereo-selective to give bimetallic complexes with octahedral coordination around Re(V), compounds 8 and 9.
Figure 12:
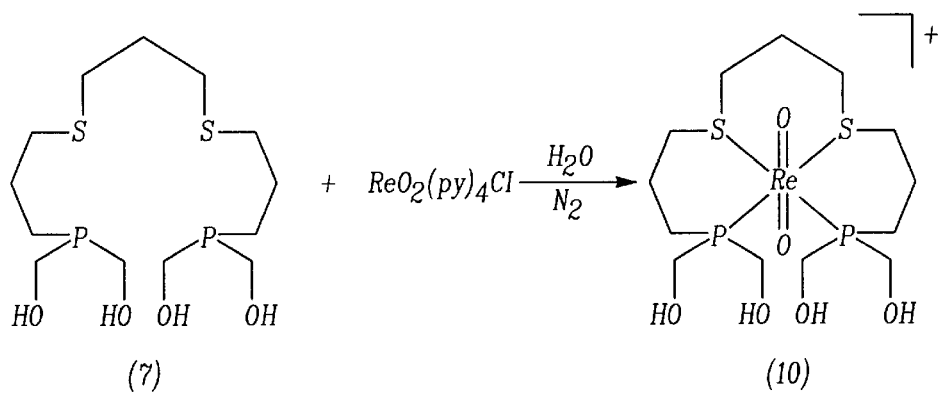
FIG. 12 illustrates a synthesis scheme for the synthesis of regio- and stereo-selective to give bimetallic complexes with an octahedrally-coordinated monometallic complex of Re(V), compound 10.

It is important to recognize that the reactions described in Schemes 2 and 3 of FIGS. 11 and 12, respectively, are regio- and stereo-selective to give bimetallic complexes with octahedral coordination around Re(V) (e.g. compounds 8 and 9) and a octahedrally-coordinated monometallic complex of Re(V) (e.g. compound 10), respectively. The fact that no traces of a bimetallic complex of the type of compound 8 or 9 was observed in the reaction of the 333 $S_2P_2$ ligand 7 with $[ReO_2(C_5H_5N)]_4Cl$ (Scheme 3 of FIG. 12), even in the presence of excess ligand, demonstrated a strong kinetic propensity in forming the monometallic Re(V) complex 10 via the six-membered metallocycles. However, in sharp contrast, reactions of the 232 and 242 $S_2P_2$ ligands 1 and 4 with $[ReO_2(C_5H_5N)]_4Cl$, as described in Scheme 2 of FIG. 11, produced the bimetallic complexes 8 and 9 as the singular chemical species with no traces of a monometallic complex of the type of compound 10. These observations signify the importance of ligand chain length, particularly the alkane chain size separating the $P^{III}$ and S centers, on the overall coordination chemistry with Re(V).

Preliminary studies on the reactions of the $P_2S_2$ ligand 7 with $^{99m}TcO_4^-$ and $^{99m}Tc$-citrate indicated the formation of the corresponding $^{99m}Tc$ complex in ~98% yield. Biodistribution studies of this complex in Sprague-Dawley rats indicated its high in vivo stability and efficient clearance from the body. Liquid chromatographic studies of urinary samples excised from the bladder further demonstrated the in vivo stability as well as lack of decomposition of the complex.

$S_2P_2$ ligands functionalized with active sites (e.g. —COOH or —NCS) so that these ligands and their $^{188}Re/^{99m}Tc$ complexes can be incorporated on specific biomolecules may be used in the design and development of biomolecular labelled radiopharmaceuticals for use in cancer diagnosis and therapy.

Example 7

Figure 15:
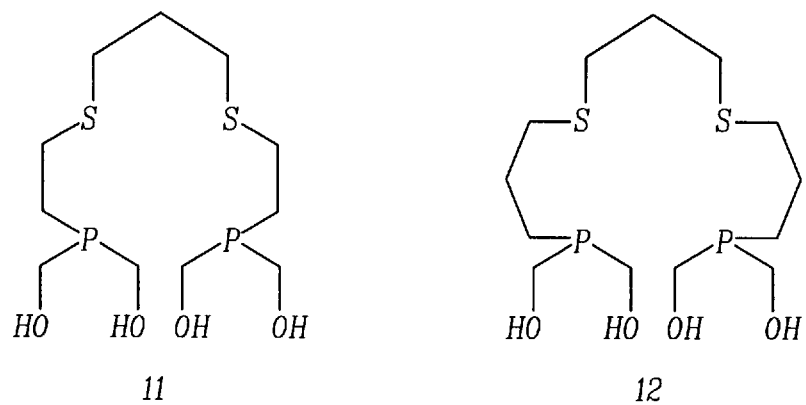
FIG. 15 illustrates dithiois bis(hydroxymethyl) phosphine ligands 11 and 12.

Materials and Methods $(HOH_2C)_2P(CH_2)_2S(CH_2)_3S(CH_2)_2P(CH_2OH)_2$, (11) and $(HOH_2C)_2P(CH_2)_3S(CH_2)_3S(CH_2)P(CH_2OH)_2$, (12) as shown in FIG. 15 were synthesized as previously reported and used without further purification. Technetium-99m was eluted from a $^{99}Mo/^{99m}Tc$ generator provided by Mallinckrodt Medical, Inc. Thin layer chromatography (TLC) analysis of the labeled compounds was performed on Selecto Scientific flexible TLC plates (Silica gel 60A, 2.5×7.5 cm) purchased from Fisher Scientific. Quantitation of the distribution of activity on the TLC plates was measured using a BIOSCAN System 200 Imaging Scanner. HPLC analysis of the labeled compounds was performed on a Waters 600E system equipped with a Waters 486 tunable absorbance detector and a 746 integrator. HPLC chromatographic solvents were purchased from Fisher Scientific and used without further purification. All other chemicals were purchased from Aldrich Chemical Company and used without further purification.

EXPERIMENTAL

Labeling of 11 and 12 with Tc-99m

A. Direct Labeling Procedure: The Tc-99m complexes of 11 and 12 were prepared by addition of 500 μL of ligand (0.1 to 5 mg/mL) to 500 μL of $^{99m}TcO_4^-$ (10–20 mCi) in isotonic saline (Scheme 2 of FIG. 14). The solutions were vortexed and allowed to incubate at 70° C. at normal pH (~7.0–7.4) for ten minutes. The solutions were allowed to stand at room temperature for ca. thirty minutes before further analyses were made.

B. Transchelation Labeling Procedure: $^{99m}Tc$-Citrate was prepared by addition of one mL of 0.1M Sodium Citrate to one mL of $^{99m}TcO_4^-$ at room temperature (Scheme 2 of FIG. 14). To this solution was added 10 μL of saturated stannous tartrate. The resulting $^{99m}Tc$-citrate complex was allowed to incubate at room temperature for ca. fifteen minutes before further use. The translabeled Tc-99m complexes of 11 and 12 were prepared by addition of 500 μL of ligand (0.2 to 0.01 mg/mL) to 500 μL of $^{99m}Tc$-Citrate. The resulting complexes were allowed to incubate at room temperature for ca. thirty minutes before further analysis.

HPLC Analysis of Tc-99m Labeled Dithio-Bisphosphines 11 and 12

All samples were prefiltered through a 0.22 μm Cameo syringe filter. High performance liquid chromatography (HPLC) analysis was performed using an analytical PRP-1 column (Hamilton, 5 μm). The mobile phase consisted of a gradient system with solvent A corresponding to water with 0.1% trifluoroacetic acid and solvent B corresponding to acetonitrile with 0.1% trifluoroacetic acid. The mobile phase started with 100% A from zero to two minutes followed by a linear gradient from 0% B to 100% B from two to seven minutes. The gradient remained at 100% B for an additional two minutes before being ramped to 0% B at time twenty minutes for column equilibration. The flow rate of the mobile phase was 1.5 mL/min. The chart speed of the integrator was 0.5 cm/min. Detection was accomplished radiometrically using an in-line NaI detector for the $^{99m}Tc$-complexes.

pH Studies of Tc-99m Labeled Dithio-Bisphosphines 11 and 12

The pH of the above $^{99m}Tc$-$S_2P_2$ complexes was adjusted to various levels using 0.1M NaOH or 0.1M HCl. Stability of the $^{99m}Tc$-$S_2P_2$ complexes at pH 3, 5, 7, and 9 was determined by monitoring the yields of the each of the complexes at various timepoints (0.5, 1, 3, 5, and 24 h) post-complexation. Five μL of the complex was spotted near the origin of a silica gel strip and developed in 0.9% saline, ethyl acetate, and acetone. Determination of the $R_f$'s and quantitation of the migration of activity on the strips was performed by counting each strip for one minute using a BIOSCAN System 200 Imaging Scanner. $^{99m}TcO_4^-$ had a $R_f$ value of approximately one in normal saline and acetone and a $R_f$ value of zero in ethyl acetate. The $^{99m}Tc$-$S_2P_2$ complexes had a $R_f$ value of zero in each of the three solvents. The absence of $^{99m}TcO_2$ was verified by subsequent analysis of each complex via HPLC. The chloroform-saline partition coefficients of the $^{99m}Tc$-$S_2P_2$ complexes were determined by vortexing a mixture of one mL normal saline at pH=7 containing $^{99m}Tc$-$S_2P_2$ with one mL of chloroform for one minute. Fifty microliters of each layer (N=5) were counted in a NaI well counter.

In Vivo Studies of Tc-99m Labeled Dithio-Bisphosphines 11 and 12

The biodistribution studies of the technetium-99m complexes of 11 and 12 were determined in Sprague-Dawley (150–250 g) rats anesthetized with sodium pentobarbital (50 mg/kg IP). The rats were injected with 5–10 μCi (185–370 kBq) of complex in 50 μL of N. saline via a cannulated right jugular vein. Tissues and organs were excised from the animals following at thirty minutes, one hour, and two hours post-injection (p.i.). Subsequently, the tissues and organs were weighed and counted in a NaI well counter and the percent injected dose (% ID) and % ID/g of each organ or tissue calculated. The % ID in whole blood was estimated assuming a whole blood volume of 6.5% the total body weight.

In order to determine the in vivo stability of each of the complexes, a urine analysis was performed. In this study, approximately 50 μCi (1850 kBq) of the technetium-99m complexes of 11 and 12 were injected into Sprague-Dawley rats anesthetized as before. The animals were sacrificed at two hours p.i. The bladder of each animal was removed and a sample of the urine was obtained for analysis. HPLC analysis of the urine samples was performed and compared to the HPLC chromatograms of the administered complexes.

RESULTS

Figure 14:
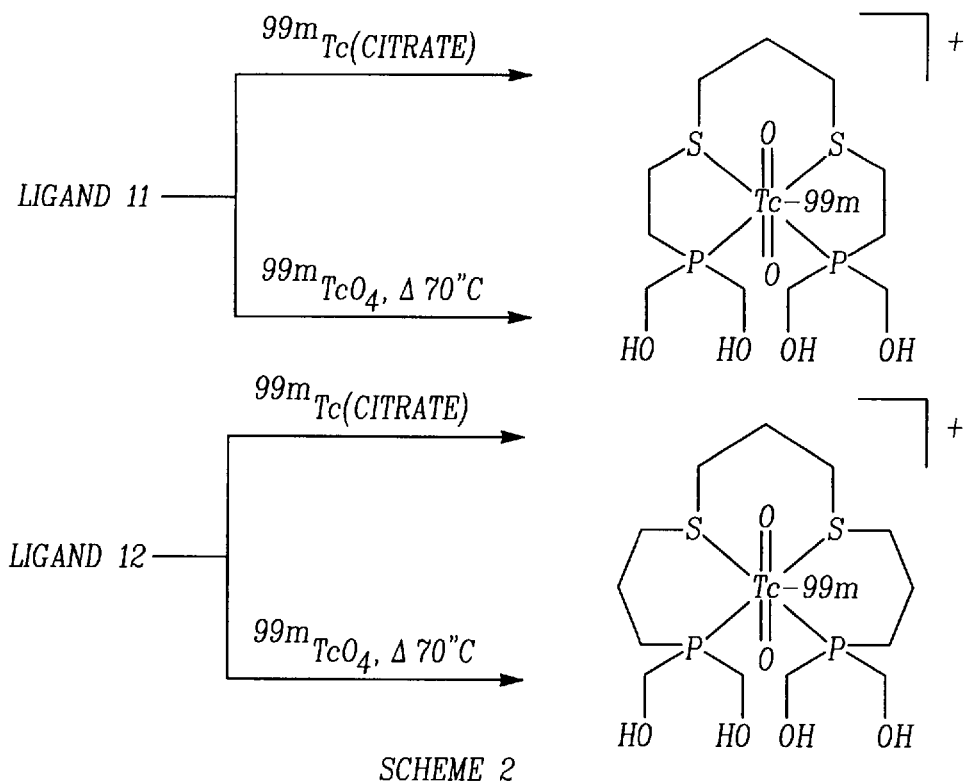
FIG. 14 illustrates a synthesis scheme for the synthesis of technetium complexes in accordance with the present invention.

The technetium-99m complexes of 11 and 12 were produced in high yields (>95%) upon simple mixing of pertechnetate with 0.1 to 5 mg/mL of 11 and 12 or by transchelation via $^{99m}$Tc-Citrate with 11 and 12 (Scheme 2 of FIG. 14). All reactions were performed at natural pH. $^{99m}$Tc-P$_2$S$_2$ complexes were formed at 25° C. in ca. 1.5 hours. A temperature dependent study of 11 using the direct labeling procedure verified ~70° C. to be the optimum temperature for complexation. All other direct labeling procedures of 11 and 12 were carried out at this temperature. All transmetallation studies were performed at room temperature. The resulting complexes were analyzed by TLC and HPLC. The pH stability profiles (see Tables 13 and 14) indicate that each of the complexes are stable in N. saline over a wide range of pH for up to twenty-four hours.

Referring to FIGS. 16a–b, HPLC chromatograms are shown for the technetium-99m complexes of 11(a) and 12(b). Each of the chromatograms show a single species with retention times of 6.39 and 6.34 minutes, respectively. The chromatograms of the transchelated reactions indicate that identical species are obtained with ligand concentrations as low as 0.01 mg/mL (~2.5×10$^{-5}$M). Collection and counting of the peak eluants for each of the complexes indicated that >95% of the activity loaded onto the column came off as singular species. Under identical conditions, pertechnetate and $^{99m}$Tc-Citrate eluted with retention times of 1.34 and 0.93 minutes, respectively. The chloroform-saline partition coefficients of the $^{99m}$Tc-complexes of 11 and 12 were each <0.0001±0.0001. This indicated the extreme hydrophilic nature of the complexes formed.

Biodistribution studies in anesthetized rats showed that both technetium-99m complexes of 11 and 12 cleared efficiently from the bloodstream via the hepatobiliary and renal-urinary pathways (see Tables 15 and 16) within two hours post-injection ((i.e., 1.20±0.23% ID for $^{99m}$Tc-11 and 0.98±0.26% ID of $^{99m}$Tc-12 remaining in whole blood at two hours p.i.). However, a notable difference between the two ligand systems is observed. The majority of the activity for complexes of 11 was excreted into the urine (i.e., 68.72±2.54% ID at two hours p.i.). Approximately 20% of the $^{99m}$Tc-11 complex cleared via the hepatobiliary pathway within two hours of injection (see Table 15 ).

Figure 17A:
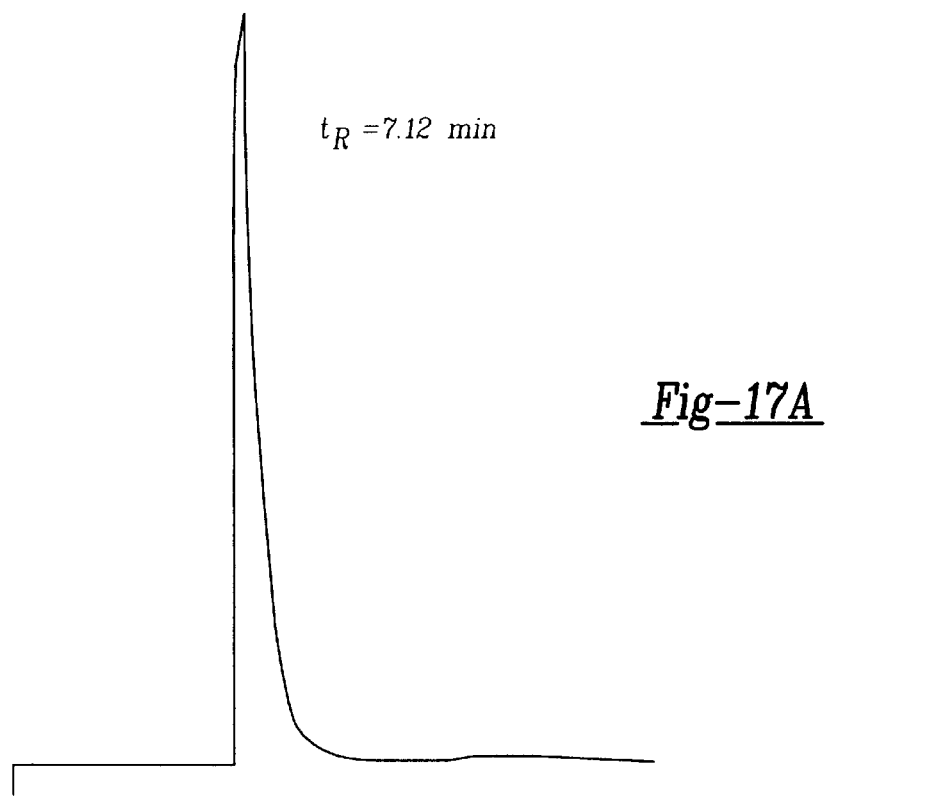
Figure 17B:
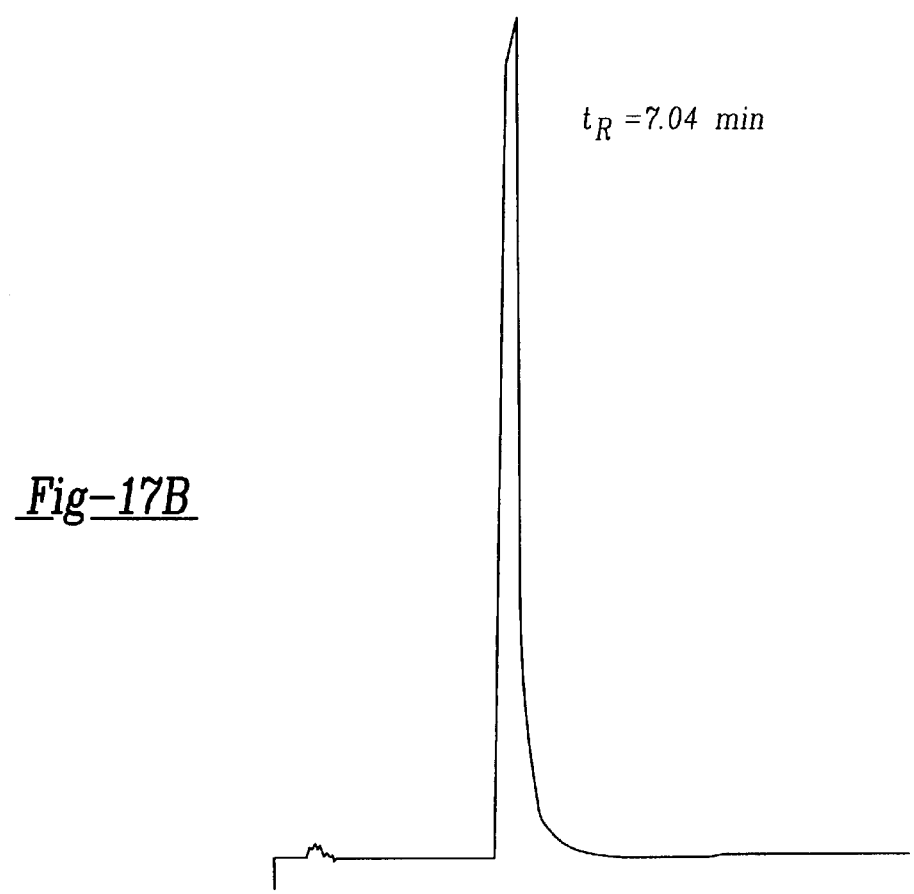

However, the hepatobiliary system is the predominant pathway of excretion for the $^{99m}$Tc-12 complex as shown in Table 16. The majority of the activity for the complexes of 12 was excreted via the bile into the small intestine. Approximately 25% of $^{99m}$Tc-12 was found in the urine at two hours post injection. Referring to FIGS. 17a–b, the $^{99m}$Tc-activity excreted into the urine was collected and subjected to HPLC analysis in order to evaluate the in vivo stability of the complex. There was no significant difference in the radiochromatograms of the collected samples (a) and the injected complex (b).

DISCUSSION

Applicants have synthesized and reported on the coordination chemistry of dithiobis(hydroxymethyl) phosphines with the early and late transition metals Pd, Pt, and Re. Early studies demonstrated the potential utility of dithiobis (hydroxymethyl)phosphines as bifunctional chelating agents for the labeling of biomolecules such as peptides or monoclonal antibodies. For example, transition metal complexes containing one ligand per metal center were obtained for each of the ligands 11 and 12. For the rhenium complexes, an interesting coordination chemistry for ligands 11 and 12 was observed. Ligand 11, when reacted with [ReO$_2$(C$_5$H$_5$N)$_4$](Cl) under refluxing conditions, produced a dinuclear complex, with two ligands and two metal centers. The formation of the rigid, 5-membered ring does not allow for the "wrapping around" of the propane bridge to form a mononuclear complex. In sharp contrast, ligand 12 produced a dioxo mononuclear species when reacted with the same Re(V) precursor. The contrast in coordination chemistries must, in fact, be due to the additional carbons in the aliphatic backbone of 12. The presence of these carbons not only allows for "wrapping around" of the ligand about the metal center, but also allows for increased stability by the formation of three six-membered rings. All of the rhenium complexes have been shown to be stable by $^{31}$P NMR to ligand challenge studies (e.g. 1.0M cysteine) in excess of twenty-four hours. All of the complexes have been characterized by $^{31}$P, $^{13}$C, $^{1}$H, 1R, and FAB mass spectroscopy. The molecular constitution of these complexes has further been confirmed by C, H analysis and X-ray crystallographic analysis.

To characterize the chemistry of technetium with ligands 11 and 12 at the tracer level, both chemical and in vivo studies of $^{99m}$Tc-11 and $^{99m}$Tc-12 were performed. These studies showed that single, hydrophilic species are obtained by simple mixing of pertechnetate with ligands 11 and 12 at concentrations as low as 0.1 mg/mL (~3×10$^{-4}$M). It is presumed that ligands 11 and 12 act as formal two electron reducing agents in the presence of $^{99m}$Tc(VII)O$_4^-$. Upon reduction of Tc(VII) to Tc(V), the P$^{III}$ centers, which are in excess, are oxidized to their corresponding phosphine oxides (P$^V$) (Clark and Podbielski, 1987). Upon reduction of $^{99m}$TcO$_4^-$ with saturated stannous tartrate, yields in excess of 95% are obtained at ligand concentrations as low as 0.01 mg/mL (2.5×10$^{-5}$M).

For the labeling of specific biomolecular compounds, the harsh conditions of direct labeling may not be suitable. For example, the intense heat or presence of stannous ion may damage the biomolecule of interest (Hnatowich, 1990, Rhodes et al., 1993). Ligand exchange (i.e. transchelation with $^{99m}$Tc-citrate), is an alternative approach for such labeling procedures. Accordingly, the labeling of ligands 11 and 12 via $^{99m}$Tc-citrate was investigated. Identical products to those produced by direct labeling, as demonstrated by HPLC, were obtained at ligand concentrations as low as 0.01 mg/mL (2.5×10$^{-5}$M). The chromatographic properties of $^{99m}$Tc-11 and $^{99m}$Tc-12 provide evidence that similar chemical structures to those of Re(V), which contain a dioxo core and P and S donor atoms in the equatorial plane, are obtained.

Pharmacokinetic studies of $^{99m}$Tc-11 and $^{99m}$Tc-12 demonstrated that each of the complexes clear efficiently from the bloodstream. The primary route of clearance for $^{99m}$Tc-11 is via the kidneys into the urine (68.7±2.5%) with approximately 20% ID clearing through the hepatobiliary pathway (see Table 15). In contrast, $^{99m}$Tc-12's primary route of clearance is via the hepatobiliary system (62.87±3.3%) with approximately 25.64±1.13% ID clearing into the urine. The notable difference in the routes of clearance can be explained by the fact that 11 and 12 differ in the number of aliphatic CH$_2$'s contained in the backbones of the ligands. Ligand 12, which contains an additional CH$_2$ linkage between the S and P donor atoms, adds additional hydrophobicity to the $^{99m}$Tc-complex, thus its clearance primarily from the hepatobiliary system. The effective clearance from blood and other nontarget organs clearly reflects the degree of polarity and solubility imparted upon the $^{99m}$Tc-complexes by the hydroxymethyl moieties. Little, if any, in vivo decomposition of the complexes occurred as was evident by minimal Tc-99m activity accumulation in the stomach. In vivo stability was further demonstrated by the lack of chemical alteration of the complexes extracted from the urinary bladder. Such stability is presumably due to the "macrocyclic" nature of the ligands.

CONCLUSION

These results indicated that the incorporation of the sulfurs and (hydroxymethyl)phosphine donors into the ligand backbone served to produce $^{99m}$Tc complexes with high in vitro and in vivo stability. It is remarkable that these complexes do not decompose even upon extensive heating and pH conditions. The presence of the hydroxymethyl groups on the phosphine donor atoms of 11 and 12 was presumably responsible for the effective clearance of $^{99m}$Tc-11 and $^{99m}$Tc-12 from blood and nontarget tissue. Furthermore, the lack of nonspecific in vivo uptake, as demonstrated in this example, demonstrated the utility of large, aliphatic, water-soluble phosphine ligands to be used as chelating moieties for various radionuclides.

Throughout this application various publications are referenced by citation or number. Full citations for the publications referenced by number are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

Elution Profile of THP[a] and $^{99m}$Tc-THP Complexes Through Amine Based Column[b]

| Compound | Elution (%) | Blank (%)[c] |
|---|---|---|
| THP[d] | <2 | >99 |
| $^{99m}$Tc-THP | 98.5 ± 5[e] | |

[a]-THP is an acronym for Tris(Hydroxymethyl)Phosphine
[b]-Waters Sep-Pak Vac amino propyl column containing 500 mg of the sorbent
[c]-Silica gel (60–200 mesh) column containing 500 mg of the sorbent
[d]-Yield of THP was determined by $^{31}$P NMR
[e]-Percent elution after 5 (8 ml) washings

TABLE 2

Stability Studies of Tc-99m $S_2P_2$

| Concentration (mg/ml)/ | Time (hrs.) | | | | |
|---|---|---|---|---|---|
| | 0.5 | 1 | 3 | 5 | 24 |
| 5.0 | 88 ± 1.3 | 95 ± 1.1 | 96 ± 0.9 | 96 ± 1.1 | 98 ± 1.1 |
| 2.5 | 79 ± 1.4 | 95 ± 1.3 | 96 ± 1.2 | 97 ± 1.3 | 98 ± 0.9 |
| 1.0 | 52 ± 1.8 | 81 ± 1.6 | 95 ± 1.5 | 98 ± 1.1 | 99 ± 1.2 |
| 0.5 | 36 ± 2.1 | 63 ± 1.4 | 92 ± 1.2 | 98 ± 1.3 | 99 ± 1.0 |
| 0.1 | 23 ± 1.7 | 50 ± 1.9 | 97 ± 1.7 | 98 ± 1.3 | 99 ± 1.2 |

$TcO_4^-$ (0.1 ml) was added to the ligand (0.1 ml) and diluted with water to give the final ligand concentration shown above

TABLE 3

Biodistribution Data of Tc-$S_2P_2$ Complex

| | Complex | | |
|---|---|---|---|
| | $^{99m}$Tc-S2P2 15 min n = 5 | $^{99m}$Tc-S2P2 1 hr n = 5 | $^{99m}$Tc-S2P2 2 hr n = 5 |
| Organ | (% Dose) | | |
| Brain | 0.04 ± 0.00 | 0.01 ± 0.00 | 0.00 ± 0.00 |
| Blood | 6.79 ± 0.22 | 2.05 ± 0.31 | 1.20 ± 0.23 |
| Heart | 0.13 ± 0.02 | 0.03 ± 0.01 | 0.02 ± 0.00 |
| Lung | 0.61 ± 0.21 | 0.76 ± 0.71 | 0.64 ± 0.11 |
| Liver | 10.42 ± 0.75 | 3.03 ± 0.35 | 2.62 ± 0.20 |
| Spleen | 0.07 ± 0.01 | 0.06 ± 0.00 | 0.06 ± 0.01 |
| Stomach | 1.08 ± 0.70 | 0.74 ± 0.47 | 0.56 ± 0.30 |
| Large Intestine | 0.68 ± 0.19 | 0.27 ± 0.11 | 0.25 ± 0.13 |
| Small Intestine | 14.92 ± 1.36 | 17.36 ± 1.65 | 17.66 ± 1.67 |
| Kidneys | 4.46 ± 0.59 | 2.85 ± 0.32 | 2.42 ± 0.34 |
| Bladder | 22.68 ± 5.50 | 65.72 ± 2.49 | 68.72 ± 2.54 |
| Muscle | 0.06 ± 0.01 | 0.02 ± 0.00 | 0.01 ± 0.00 |
| Carcass | 44.28 ± 5.43 | 8.85 ± 1.76 | 6.86 ± 1.53 |

TABLE 4

Complexation of $^{99m}$Tc-$N_2P_2$ via Ligand Exchange from $^{99m}$Tc-Citrate

| | Time (hrs.) | | | | |
|---|---|---|---|---|---|
| Conc. (mg/ml) | 0.5 | 1 | 3 | 5 | 24 |
| 5.00 | 96 ± 1 | 96 ± 1 | 96 ± 1 | 96 ± 1 | 96 ± 2 |
| 2.50 | 95 ± 1 | 95 ± 1 | 95 ± 1 | 95 ± 1 | 94 ± 2 |
| 1.00 | 95 ± 1 | 95 ± 1 | 95 ± 1 | 95 ± 1 | 95 ± 2 |
| 0.50 | 94 ± 1 | 95 ± 1 | 95 ± 1 | 95 ± 1 | 95 ± 2 |
| 0.10 | 83 ± 1 | 85 ± 1 | 85 ± 1 | 84 ± 1 | 81 ± 2 |
| 0.01 | 68 ± 1 | 70 ± 1 | 70 ± 1 | 72 ± 2 | 71 ± 2 |

The $^{99m}$Tc-$N_2P_2$ complex was formed at a neutral pH (pH=6–7) by mixing 0.5 ml of the ligand and a 0.5 ml solution of $^{99m}$Tc-Citrate (10–20 mCi) to give the final concentration of the ligand as shown above.

TABLE 5

Biodistribution Data of $^{99m}$Tc-$N_2P_2$ Complex

| | Complex | | |
|---|---|---|---|
| | $^{99m}$Tc-N2P2 30 min n = 4 | $^{99m}$Tc-N2P2 1 hr n = 4 | $^{99m}$Tc-N2P2 2 hr n = 5 |
| Organ | (% Dose) | | |
| Brain | 0.04 ± 0.00 | 0.03 ± 0.01 | 0.01 ± 0.00 |
| Blood | 6.91 ± 0.79 | 3.66 ± 0.54 | 1.62 ± 0.25 |
| Heart | 0.15 ± 0.01 | 0.07 ± 0.02 | 0.03 ± 0.00 |
| Lung | 0.49 ± 0.08 | 0.29 ± 0.11 | 0.17 ± 0.03 |
| Liver | 1.94 ± 0.21 | 1.55 ± 0.19 | 1.16 ± 0.07 |
| Spleen | 0.06 ± 0.00 | 0.04 ± 0.00 | 0.03 ± 0.00 |
| Stomach | 0.54 ± 0.20 | 0.75 ± 0.41 | 0.33 ± 0.10 |
| Large Intestine | 0.57 ± 0.10 | 0.35 ± 0.04 | 0.19 ± 0.04 |
| Small Intestine | 3.24 ± 0.52 | 4.16 ± 0.82 | 4.24 ± 0.43 |
| Kidneys | 3.12 ± 0.55 | 3.20 ± 0.43 | 2.76 ± 0.28 |
| Bladder | 49.20 ± 5.12 | 63.91 ± 4.66 | 78.72 ± 1.59 |
| Muscle | 0.07 ± 0.02 | 0.04 ± 0.01 | 0.02 ± 0.00 |
| Carcass | 39.84 ± 4.34 | 25.12 ± 4.93 | 12.10 ± 1.17 |

TABLE 6

Crystal Data for Complexes 8, 9, and 10

| | $C_{22}H_{54}Cl_2O_{13}P_4Re_2S_4$(8) | $C_{24}H_{56}O_{20}P_4Re_4S_4$(9) | $C_{14}H_{34}ClO_7P_2ReS_2$(10) |
|---|---|---|---|
| formula | | | |
| space group | P $2_1$/c | P $-1$ | P $2_1$/n |
| fw | 1222.07 | 1661.61 | 662.15 |
| a, Å | 10.7982(5) | 10.3762(5) | 10.6224(6) |
| b, Å | 23.486(1) | 12.1099(6) | 12.5532(8) |
| c, Å | 15.4408(8) | 18.7555(9) | 18.5767(11) |
| α, deg | 90 | 90.259(1) | 90 |
| β, deg | 94.539(1) | 91.900(1) | 103.6630(10) |
| γ, deg | 90 | 104.965(1) | 90 |
| T, K | 293(2) | 293(2) | 293(2) |
| λ, Å | 0.71070 | 0.71070 | 0.71070 |
| Z | 4 | 2 | 4 |
| F(000) | 2392 | 1568 | 1240 |
| V, Å$^3$ | 3905.1(3) | 2275.3(2) | 2407.0(2) |
| $\rho_{calc}$, g/cm$^3$ | 2.079 | 2.425 | 1.739 |
| $\rho_{obsd}$, g/cm$^3$ | not measured | not measured | not measured |
| μ, mm$^{-1}$ | 6.764 | 10.999 | 5.488 |
| $R_1$, $wR_2$ | 0.0246, 0.0574 | 0.0546, 0.1412 | 0.0261, 0.0656 |

$R_1$ factor definition: $R_1 = \Sigma||F_o| - |F_c||/\Sigma|F_o|$.
SHELXL - 93 $wR_2$ factor definition: $wR_2 = [\Sigma w(F_o^2 - F_c^2)^2/\Sigma w(F_o^2)^2]^{1/2}$.
Weighting scheme: $w = 1/[\sigma 2(F_o)^2 + (np)^2 + 0.00p]$, $p = (max(F_o^2) + 2F_c^2)/3$.

TABLE 7

Selected Bond Distances (Å) and Angles (deg) for 8.

| | | | |
|---|---|---|---|
| Re1—O10 | 1.774(3) | Re1—O9 | 1.775(3) |
| Re1—P4 | 2.4052(10) | Re1—P1 | 2.4110(9) |
| Re1—S4 | 2.5543(9) | Re1—S1 | 2.5337(9) |
| Re2—O12 | 1.763(3) | Re2—O11 | 1.781(3) |
| Re2—P3 | 2.4004(9) | Re2—P2 | 2.3962(10) |
| Re2—S3 | 2.5804(10) | Re2—S2 | 2.5343(9) |
| O10—Re1—O9 | 178.47(12) | O12—Re2—O11 | 174.25(13) |
| P4—Re1—P1 | 100.34(3) | P2—Re2—P3 | 99.68(3) |
| S1—Re1—S4 | 95.90(3) | S2—Re2—S3 | 95.95(3) |
| P1—Re1—S1 | 81.92(3) | P2—Re2—S2 | 82.79(3) |
| P4—Re1—S4 | 82.07(3) | P3—Re2—S3 | 81.57(3) |

TABLE 8

Selected Bond Distances (Å) and Angles (deg) for 9.

| | | | |
|---|---|---|---|
| Re1a—O1a | 1.754(8) | Re1a—O2a | 1.798(8) |
| Re1a—P1a | 2.414(3) | Re1a—P2a | 2.410(3) |
| Re1a—S1a | 2.515(3) | Re1a—S2a | 2.536(3) |
| Re1b—O1b | 1.749(7) | Re1b—O2b | 1.786(7) |
| Re1b—P1b | 2.405(3) | Re1b—P2b | 2.421(3) |
| Re1b—S1b | 2.538(3) | Re1b—S2b | 2.510(3) |
| O1a—Re1a—O2a | 177.2(3) | O1b—Re1b—O1b | 176.1(4) |
| P1a—Re1a—P2a | 99.67(10) | P1b—Re1b—P2b | 102.66(10) |
| S1a—Re1a—S2a | 95.98(9) | S1b—Re1b—S2b | 94.23(9) |
| P1a—Re1a—S1a | 81.76() | P1b—Re1b—S1b | 82.80(10) |
| P2a—Re1a—S2a | 83.18(9) | P2b—Re1b—S2b | 81.07(9) |

TABLE 9

Selected Bond Distances (Å) and Angles (deg) for 10.

| | | | |
|---|---|---|---|
| Re—O1 | 1.757(3) | Re—O2 | 1.782(3) |
| Re—P1 | 2.4248(10) | Re—P2 | 2.4176(10) |
| Re—S1 | 2.5503(10) | Re—S2 | 2.5323(11) |
| O1—Re—O2 | 174.70(12) | P1—Re—P2 | 100.84(3) |
| S1—Re—S2 | 88.10(4) | P2—Re—S2 | 87.02(4) |
| P1—Re—S1 | 84.07(3) | P1—Re—S2 | 172.03(4) |
| P2—Re—S1 | 174.98(3) | | |

TABLE 10

Atomic Coordinates (× 10$^4$) and equivalent isotropic displacement parameters (Å$^2$ × 10$^3$) for 8.

| | x | y | z | $U_{eq}$ |
|---|---|---|---|---|
| Re1 | 7399(1) | −354(1) | 1602(1) | 16(1) |
| Re2 | 3313(1) | 1613(1) | 3752(1) | 18(1) |
| Cl1 | 8225(1) | 829(1) | 5186(1) | 58(1) |
| Cl2 | 9841(1) | 1730(1) | 755(1) | 41(1) |
| S1 | 7735(1) | 494(1) | 2607(1) | 24(1) |
| S2 | 4775(1) | 1660(1) | 2548(1) | 22(1) |
| S3 | 4195(1) | 679(1) | 4430(1) | 24(1) |
| S4 | 5054(1) | −223(1) | 1316(1) | 21(1) |
| P1 | 9635(1) | −391(1) | 1794(1) | 19(1) |
| P2 | 2530(1) | 2480(1) | 3100(1) | 21(1) |
| P3 | 2061(1) | 1563(1) | 4966(1) | 22(1) |
| P4 | 6988(1) | −1179(1) | 701(1)( | 22(1) |
| O1 | 11657(3) | −345(2) | 902(2) | 44(1) |
| O2 | 11506(3) | −848(2) | 2827(2) | 41(1) |
| O3 | 2386(3) | 3075(1) | 4589(2) | 35(2) |
| O4 | 547(3) | 3063(2) | 2396(2) | 45(1) |
| O5 | 2153(3) | 1799(1) | 6691(2) | 37(1) |
| O6 | −312(3) | 1693(2) | 4251(2) | 48(1) |
| O7 | 7292(3) | −1572(2) | −911(2) | 49(1) |
| O8 | 9004(3) | −1846(2) | 1038(2) | 40(1) |
| O9 | 7558(2) | 80(1) | 677(2) | 25(1) |
| O10 | 7201(2) | −780(1) | 2530(2) | 26(1) |
| O11 | 4484(2) | 1974(1) | 4419(2) | 26(1) |
| O12 | 2254(2) | 1196(1) | 3098(2) | 28(1) |
| C1 | 10435(3) | −562(2) | 827(2) | 26(1) |
| C2 | 10205(4) | −882(2) | 2656(3) | 29(1) |
| C3 | 10155(4) | 322(2) | 2117(3) | 28(1) |
| C4 | 9418(4) | 542(2) | 2851(3) | 34(1) |
| C5 | 7400(4) | 1123(2) | 1941(3) | 29(1) |
| C6 | 7350(4) | 1660(2) | 2487(3) | 29(1) |
| C7 | 6321(4) | 1654(2) | 3109(3) | 28(1) |
| C8 | 4694(4) | 2413(2) | 2234(3) | 30(1) |
| C9 | 3357(4) | 2620(2) | 2130(3) | 28(1) |
| C10 | 2845(4) | 3117(2) | 3754(3) | 28(1) |
| C11 | 873(4) | 2525(2) | 2727(3) | 34(1) |
| C12 | 2850(4) | 1876(2) | 5956(2) | 30(1) |
| C13 | 494(4) | 1879(2) | 4955(3) | 33(1) |
| C14 | 1926(4) | 803(2) | 5204(3) | 30(1) |
| C15 | 3207(4) | 535(2) | 5316(3) | 31(1) |
| C16 | 3706(4) | 114(2) | 3675(2) | 24(1) |
| C17 | 4458(4) | 150(2) | 2886(3) | 30(1) |
| C18 | 4304(4) | −373(2) | 2304(3) | 25(1) |
| C19 | 4548(4) | −815(2) | 606(3) | 29(1) |
| C20 | 5332(4) | −1341(2) | 724(3) | 32(1) |

TABLE 10-continued

Atomic Coordinates ($\times 10^4$) and equivalent isotropic displacement parameters ($\text{Å}^2 \times 10^3$) for 8.

| | x | y | z | $U_{eq}$ |
|---|---|---|---|---|
| C21 | 7306(4) | −1064(2) | −436(3) | 35(1) |
| C22 | 7696(4) | −1864(2) | 1010(3) | 32(1) |
| O1W | 6207(6) | 1752(3) | 5758(4) | 97(2) |

$U_{eq}$ is defined as one third of the trace of the orthogonalized Uij tensor.

TABLE 11

Atomic Coordinates ($\times 10^4$) and equivalent isotropic displacement parameters ($\text{Å}^2 \times 10^3$) for 9.

| | x | y | z | $U_{eq}$ |
|---|---|---|---|---|
| Re1a | 10674(1) | −3048(1) | 8909(1) | 28(1) |
| S1a | 11881(3) | −1115(2) | 9411(2) | 41(1) |
| S2a | 8554(3) | −3227(2) | 9585(2) | 38(1) |
| P1a | 12802(3) | −2886(3) | 8378(2) | 40(1) |
| P2a | 9389(3) | −4781(2) | 8327(2) | 35(1) |
| O1a | 11247(8) | −3732(7) | 9629(4) | 44(2) |
| O2a | 10055(8) | −2307(6) | 8200(4) | 42(2) |
| O3a | 10724(12) | −5092(9) | 7188(6) | 74(3) |
| O4a | 8806(11) | −7079(7) | 8263(5) | 63(3) |
| O5a | 13568(44) | −1841(25) | 7185(10) | 74(3) |
| O6a | 14836(12) | −3852(12) | 8395(8) | 100(4) |
| C1a | 13943(15) | −1624(16) | 8749(11) | 109(9) |
| C2a | 13601(15) | −1082(19) | 9312(14) | 131(11) |
| C3a | 11786(14) | −1067(10) | 10368(6) | 50(3) |
| C4a | 12424(14) | 157(10) | 10649(6) | 49(3) |
| C5a | 8355(12) | −1006(9) | 9542(7) | 43(3) |
| C6a | 7692(12) | −2200(9) | 9257(6) | 39(2) |
| C7a | 7444(13) | −4578(9) | 9249(7) | 50(3) |
| C8a | 7644(13) | −4823(11) | 8480(8) | 55(3) |
| C9a | 9501(15) | −4854(10) | 7363(6) | 55(3) |
| C10a | 9637(14) | −6143(9) | 8639(7) | 47(3) |
| C11a | 12965(18) | −2671(15) | 7424(8) | 76(5) |
| C12a | 13519(18) | −4091(19) | 8565(11) | 98(7) |
| Re1b | 9131(1) | 1673(1) | 6098(1) | 29(1) |
| S1b | 11300(3) | 2403(2) | 5460(2) | 42(1) |
| S2b | 8082(3) | 3161(2) | 5590(2) | 36(1) |
| P1b | 10340(3) | 452(2) | 6668(2) | 36(1) |
| P2b | 6908(3) | 960(2) | 6541(2) | 35(1) |
| O1b | 8668(8) | 784(6) | 5345(4) | 43(2) |
| O2b | 9695(8) | 2638(6) | 6834(4) | 43(2) |
| O3b | 4516(9) | −420(10) | 6045(6) | 69(3) |
| O4b | 6566(14) | −728(9) | 7478(8) | 95(4) |
| O5b | 10596(13) | −1726(9) | 6674(7) | 82(4) |
| O6b | 9170(12) | −506(10) | 7830(6) | 79(3) |
| C1b | 12113(12) | 1100(11) | 6521(8) | 53(3) |
| C2b | 12318(12) | 1482(12) | 5755(8) | 55(3) |
| C3b | 12208(12) | 3795(10) | 5802(6) | 45(3) |
| C4b | 11610(13) | 4710(10) | 5497(7) | 47(3) |
| C5b | 7528(13) | 4099(10) | 4328(6) | 48(3) |
| C6b | 8105(13) | 3165(9) | 4628(6) | 46(3) |
| C7b | 6299(12) | 2629(11) | 5713(8) | 54(3) |
| C8b | 6088(12) | 2116(10) | 6452(7) | 50(3) |
| C9b | 5912(13) | −176(11) | 5940(7) | 54(3) |
| C10b | 6536(14) | 434(11) | 7443(7) | 53(3) |
| C11b | 9925(15) | −996(11) | 6309(8) | 62(4) |
| C12b | 10314(13) | 310(10) | 7630(6) | 46(3) |
| Re1c | 6354(1) | −3723(1) | 6348(1) | 69(1) |
| O1c | 5000(23) | −4219(25) | 6893(14) | 314(6) |
| O2c | 6710(31) | −4870(18) | 5990(15) | 314(6 |
| O3c | 5949(30) | −2903(22) | 5690(13) | 314(6) |
| O4c | 7644(23) | −2974(24) | 6890(14) | 314(6) |
| Re1d | 14036(1) | 2456(1) | 8623(1) | 136(1) |
| O1d | 14741(28) | 3501(20) | 8059(14) | 314(6) |
| O2d | 14812(28) | 2519(26) | 9410(10) | 314(6) |
| O3d | 12358(17) | 2400(26) | 8708(17) | 314(6) |
| O4d | 13982(31) | 1170(17) | 8184(15) | 314(6) |

$U_{eq}$ is defined as one third of the trace of the orthogonalized Uij tensor.

TABLE 12

Atomic Coordinates ($\times 10^4$) and equivalent isotropic displacement parameters ($\text{Å}^2 \times 10^3$) for 10.

| | x | y | z | $U_{eq}$ |
|---|---|---|---|---|
| Re | 7095(1) | 1363(1) | 1458(1) | 28(1) |
| Cl | 8210(1) | 2168(1) | −1884(1) | 76(1) |
| S1 | 4646(1) | 1601(1) | 1218(1) | 45(1) |
| S2 | 6925(1) | 1855(1) | 116(1) | 48(1) |
| P1 | 6946(1) | 972(1) | 2713(1) | 30(1) |
| P2 | 9394(1) | 1140(1) | 1569(1) | 34(1) |
| O1 | 6799(3) | 28(2) | 1187(2) | 38(1) |
| O2 | 7264(3) | 2748(2) | 1669(2) | 38(1) |
| O3 | 6039(4) | 1996(3) | 3783(2) | 58(1) |
| O4 | 8903(3) | −431(2) | 3228(2) | 57(1) |
| O5 | 10395(3) | −165(3) | 1000(2) | 56(1) |
| O6 | 10472(4) | 1958(4) | 2898(2) | 75(1) |
| O7 | 11434(8) | −357(6) | 4337(4) | 157(3) |
| C1 | 5716(4) | −31(3) | 2752(3) | 46(1) |
| C2 | 4326(4) | 233(4) | 2353(3) | 56(1) |
| C3 | 4074(4) | 348(4) | 1528(3) | 59(1) |
| C4 | 4080(5) | 1344(4) | 225(3) | 59(1) |
| C5 | 4281(5) | 2259(5) | −260(3) | 67(2) |
| C6 | 5587(5) | 2792(4) | −67(3) | 61(1) |
| C7 | 8188(6) | 2807(4) | 93(3) | 62(1) |
| C8 | 9537(5) | 2354(5) | 298(3) | 63(1) |
| C9 | 10121(5) | 2192(4) | 1125(3) | 51(1) |
| C10 | 6449(4) | 2193(3) | 3118(2) | 39(1) |
| C11 | 8331(4) | 507(3) | 3433(2) | 42(1) |
| C12 | 9641(4) | −78(3) | 1071(3) | 49(1) |
| C13 | 10562(4) | 1046(5) | 2464(3) | 53(1) |
| C14 | 12670(12) | −598(10) | 4134(8) | 200(7) |

$U_{eq}$ is defined as one third of the trace of the orthogonalized Uij tensor.

TABLE 13

Radiochemical Purity (RCP) of $^{99m}$Tc-11 Determined at Various Times After Complexation at Various pH Values in N-Saline.[a]

| | Radiochemical Purity (%) Time (h) | | | |
|---|---|---|---|---|
| pH | 1 | 3 | 5 | 24 |
| 3 | 97 ± 1 | 96 ± 1 | 97 ± 1 | 96 ± 1 |
| 5 | 97 ± 2 | 98 ± 1 | 98 ± 1 | 96 ± 2 |
| 7 | 98 ± 1 | 98 ± 2 | 97 ± 1 | 96 ± 2 |
| 9 | 96 ± 1 | 97 ± 1 | 95 ± 2 | 96 ± 2 |
| 7.4 | 98 ± 1 | 98 ± 1 | 97 ± 1 | 97 ± 1 |

[a]The stability studies of pH values 3–9 in N. saline were conducted by incubation at room temperature (N = 4).

TABLE 14

Radiochemical Purity (RCP) of $^{99m}$Tc-11 Determined at Various Times After Complexation at Various pH Values in N-Saline.[a]

| | Radiochemical Purity (%) Time (h) | | | |
|---|---|---|---|---|
| pH | 1 | 3 | 5 | 24 |
| 3 | 97 ± 1 | 97 ± 2 | 97 ± 1 | 96 ± 1 |
| 5 | 97 ± 1 | 97 ± 1 | 97 ± 1 | 97 ± 1 |
| 7 | 96 ± 2 | 96 ± 2 | 96 ± 2 | 97 ± 2 |
| 9 | 97 ± 1 | 96 ± 1 | 97 ± 2 | 97 ± 1 |
| 7.4 | 96 ± 1 | 96 ± 1 | 95 ± 2 | 95 ± 3 |

[a]The stability studies of pH values 3–9 in N. saline were conducted by incubation at room temperature (N = 4).

TABLE 15

Biodistribution of $^{99m}$Tc-11 in Rats as a Function of Time After Intravenous Administration.

| Organ | 15 minutes | 1 hour | 2 hour |
|---|---|---|---|
| | Percent injected dose/organ[a] | | |
| Brain | 0.04 ± 0.00 | 0.01 ± 0.00 | 0.00 ± 0.00 |
| Blood[b] | 6.79 ± 0.22 | 2.05 ± 0.31 | 1.20 ± 0.23 |
| Heart | 0.13 ± 0.02 | 0.03 ± 0.01 | 0.02 ± 0.00 |
| Lung | 0.61 ± 0.21 | 0.76 ± 0.71 | 0.64 ± 0.11 |
| Liver | 10.42 ± 0.75 | 3.03 ± 0.35 | 2.62 ± 0.20 |
| Spleen | 0.07 ± 0.01 | 0.06 ± 0.00 | 0.06 ± 0.01 |
| Stomach | 1.08 ± 0.70 | 0.74 ± 0.47 | 0.56 ± 0.30 |
| Large Intestine | 0.68 ± 0.19 | 0.27 ± 0.11 | 0.25 ± 0.13 |
| Small Intestine | 14.92 ± 1.36 | 17.36 ± 1.65 | 17.66 ± 1.67 |
| Kidneys | 4.46 ± 0.59 | 2.85 ± 0.32 | 2.42 ± 0.34 |
| Urine | 22.68 ± 5.50 | 65.72 ± 2.49 | 68.72 ± 2.54 |

[a]Values represent the mean ± SD (n = 5) of the percent injected dose/organ (% ID/organ). Body weights of Sprague-Dawley rats ranged from 180–250 g.
[b]Total blood volume is estimated to be 6.5% of the body weight.

TABLE 16

Biodistribution of $^{99m}$Tc-12 in Rats as a Function of Time After Intravenous Administration.

| Organ | 15 minutes | 1 hour | 2 hour |
|---|---|---|---|
| | Percent injected dose/organ[a] | | |
| Brain | 0.03 ± 0.01 | 0.01 ± 0.00 | 0.00 ± 0.00 |
| Blood[b] | 3.82 ± 0.88 | 1.92 ± 0.64 | 0.98 ± 0.26 |
| Heart | 0.09 ± 0.00 | 0.05 ± 0.02 | 0.03 ± 0.00 |
| Lung | 0.59 ± 0.35 | 0.66 ± 0.19 | 0.57 ± 0.32 |
| Liver | 11.50 ± 1.18 | 12.98 ± 0.67 | 12.06 ± 2.40 |
| Spleen | 0.25 ± 0.04 | 0.60 ± 0.28 | 0.79 ± 0.30 |
| Stomach | 0.36 ± 0.36 | 0.57 ± 0.39 | 0.97 ± 0.59 |
| Large Intestine | 0.30 ± 0.05 | 0.16 ± 0.06 | 0.15 ± 0.00 |
| Small Intestine | 46.82 ± 3.13 | 49.19 ± 3.86 | 50.81 ± 4.38 |
| Kidneys | 2.59 ± 0.40 | 1.79 ± 0.39 | 1.61 ± 0.16 |
| Urine | 16.99 ± 2.72 | 23.34 ± 3.99 | 25.64 ± 1.13 |

[a]Values represent the mean ± SD (n = 5) of the percent injected dose/organ (% ID/organ). Body weights of Sprague-Dawley rats ranged from 180–250 g.
[b]Total blood volume is estimated to be 6.5% of the body weight.

REFERENCES

Abrams et al., "Technetium-99m-human polyclonal IgG radiolabeled via the Hydrazino Nicotinamide derivative for imaging focal sites of infection in rats" *J Nucl Med* 31: 2022–2028, 1990a.

Abrams et al., "Synthesis and crystal and molecular structure of a Technetium-Hydralazino complex [TcCl$_2$ (C$_8$H$_5$N$_4$)$_2$] G0.75C$_7$H$_8$" *Inorg Chim Acta* 173: 133–135, 1990b.

Archer et al., *In Technetium and Rhenium in Chemistry and Nuclear Medicine* -4; Nicolini, M., Bandoli, G. Mazzi, U., Eds.; Servizi Grafici Editoriali, Padova, 173 (1995).

Bandoli et al., *Inorg. Chem.*, 23, 2898 (1984).

Beard et al, *Inorg. Chem.*, 4, 797 (1965).

Berning et al., unpublished results.

Berning et al., *J. Nucl. Med. Biol.*, 23, 617 (1996).

Betz et al., "Basic Neurochem. Molecular Cell, (Raven Press Ltd, N.Y.) 5th Ed., 681–699, 1994.

Blessing, *Acta Crystallogr.*, Sect A, 51, 33 (1995).

Brem et al., "Polymers as controlled drug delivery devised for the treatment of malignant brain tumors" *Eur. J. Pharm. Biopharm* 39: 2–7 (1993).

Chianelli et al., "$^{99m}$Tc-interleukia-2: a new radiopharmaceutical for the in vivo detection of lymphocytic infiltration" *J Nucl Biol Ed* 38: 476, 1994.

Clarke and Podbielski, "Medical Diagnostic Imaging with Complexes of 99mTc", *Coord. Chem. Rev.*, 78, pp. 253–331 (1987).

DeRosch et al., *J. Nucl. Med.*, 33, 850 (1992).

Deutsch, "Aspects of the chemistry of technetium phosphine complexes" *Radiochim Acta* 63: 195–197, 1993.

Fritzberg et al., "Specific and stable labeling of antibodies with $^{99m}$Tc with a dimide dithiolate chelating agent" *Proc. Natl. Acad. Sci.*, USA 85: 4025–4029, 1988.

Greenwood and Earnshaw, *In Chemistry of the Elements:* Pergamon Press, New York, Chapter 12, 546–636 (1993).

Gustavson et al., "Synthesis of a new class of Tc-chelating agents" N$_2$S$_2$ monoaminemonoamide (MAMA) ligands" *Tetrahedron Lett*, 32: 5485–5488, 1991.

Higley et al., *J. Nucl. Med.*, 34, 30 (1993).

Hnatowich, "Antibody radiolabeling, problems and promises", *Nucl. Med. Biol.*, 17, pp. 49–55 (1990).

Ichimura et al., *Inorg. Chem.*, 23, 1272 (1984).

Jain et al, *J. Nucl. Med.*, 34, 1254, (1993).

Jurisson et al, "Coordination compounds in nuclear medicine" *Chem Rev* 93: 1137–1156, 1993.

Katti, *Current Science*, 70, 219 (1996).

Katti et al, *Chem. Soc. Rev.*, 97, (1995).

Kelly et al., *J Nucl Med* 34: 222–227, 1993.

Knight et al. "Thrombus imaging with $^{99m}$Tc synthetic peptides based upon the binding domain of a monoclonal antibody to activated platelets" *J Nucl Med* 35: 282–288, 1994.

Libson et al., *Inorg. Chem.*, 22(12), 1695 (1983).

Lister-James et al., "A structure-activity-relationship (SAR) study of somatostatin receptor-binding peptides radiolabeled with $^{99m}$Tc" *J Nucl Med*, 35: 257–258P, 1994.

Marmion et al., "Radiopharmaceutical Development of TechneScan Q12. In *Technetium and Rhenium in Chemistry and Nuclear Medicine*- 4; Nicolini, M., Bandoli, B., Mazi, U., Eds.; Servizi Grafici Editoriali, Padova, pp. 253–258 (1995).

Marmion et al., "Radiopharmaceutical development of TechneScan Q-12" *J Nucl Biol Med* 38: 455–456, 1994.

Mayer and Kaska, "Stereochemical control of transition metal complexes by polyphosphine ligands", *Chem. Rev.*, 94, pp. 1239–1272 (1994).

Meares et al., "Chelate radiochemistry: cleavable linkers lead to altered levels of radioactivity in the liver" *Int J Cancer* 2: 99–102, 1988.

Muna et al., "Synthesis, radiochemical and biological evaluation of $^{99m}$Tc[N4(O)Phe]-octreotide, a new octreotide derivative with high affinity for somatostatin receptors" *J Nucl Bio Med* 38: 452, 1994.

Nardelli *Comput. Chem.*, 7(3), 95 (1983).

Noch et al., "$^{99m}$Tc-N$_4$-Lys-Biotin, a new biotin derivative useful for pretargeted avidin-biotin immunoscintigraphy, synthesis, radiochemistry and biological evaluation" *J Nucl Biol Med* 38: 460, 1994.

Nowotnik and Nunn, "Technetium SPECT agents for imaging heart and brain" *DN* and *P* 5: 174–183, 1992.

Orpen et al., *Chem. Soc., Dalton Trans.*, S1 (1989).

Parker, "Tumor targeting with radiolabeled macrocycle-antibody conjugates" *Chem. Soc. Rev.* 19: 271–291, 1990.

Pardridge, et al., *West J. Med.* 156(3) pp. 281–286 (1992).

Pardridge, *Pharm. Toxicol.* 71(1): 3–10, 1992.

Partridge, et al., *Porch. Natl. Acad. SCI. USA* 90(7) pp. 2618–2622 (1993).

Pasqualine et al., "Bis(dithiocarbamot)nitrido $^{99m}$Tc radiopharmaceuticals: a class of neutral myocardial imaging agents" *J Nucl Med* 35: 334–331, 1994.

Rao et al., "Kinetics and mechanism of reactions of S-protected dithiol monoaminemonoamide (MAMA) ligands with technetium" *Nucl Med Biol,* 19: 889–895, 1992.

Reddy et al., *Inorg. Chem.,* 35, 1753 (1996).

Reddy et al, *J. Chem. Soc., Dalton Trans.,* 4459 (1996).

Reddy et al., *J. Chem. Soc., Dalton Trans.,* 1301 (1996).

Reddy et al., "Hydroxymethyl bis(phosphines) and their palladium(II) and platinum(II) complexes formed via biphasic reactions. Crystal structure of [Pd{HOH$_2$C)$_2$PC$_6$H$_4$P(CH$_2$OH)$_2$}$_2$]Cl$_2$. *J. Chem. Soc., Dalton Trans,* pp. 1301–1304 (1996).

Reddy et al., "Chemistry in Environmentally Benign Media. 3. Synthesis and Characterization of Rhenium(V) Complexes Derived from Novel Water-Soluble (Hydroxymethyl)phosphines. Crystal Structures of [Re(O)$_2${HOH$_2$C)$_2$PC$_6$H$_4$P(CH$_2$OH)$_2$}$_2$]I and [Re(O)$_2${HOH$_2$C)$_2$PCH$_2$CH$_2$P(CH$_2$OH)$_2$}$_2$]Cl", *Inorg. Chem.,* 35, pp. 1753–1757 (1996).

Reddy et al., *Inorg. Chim. Acta.,* 240, 367 (1995).

Refosco et al., *J. Chem. Soc. Dalton Trans.* 605 (1993).

Sheldrick, Program for Crystal Structure Refinement. University of Gottingen, Germany (1993).

Sheldrick, *Acta Crystallogr.,* A46, 467 (1990).

Smith et al., *J. Chem. Soc., Chem. Commun.,* 2557 (1996).

Smith et al,. *Inorg. Chem.* Submitted for Publication.

Tisato et al., *Inorg. Chem.,* 34, 1779 (1995).

Troutner, *Nucl Med Biol* 14: 171, 1987.

Vanderheyden et al., *Inorg. Chem.,* 24 1666 (1985).

Vanderheyden et al., *Inorg. Chem.,* 23, 3184 (1984). Volkert et al., "Therapeutic radio-nuclides: production and decay property considerations" *J Nucl Med* 32: 174–185, 1991.

Wilbur, "Radiohalogenation of proteins: an overview of radionuclides, labeling methods and reagents for conjugate labeling" *Bioconj Chem* 3: 433–470, 1992.

What is claimed is:

1. A method for radiological imaging, said method comprising the steps of:

administering an effective amount of a compound of the formula:

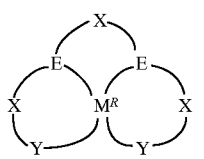 (RP)

wherein $M^R$ is a transition metal in a reduced state; X is (CHR)$_n$ where (n=0, 1, 2, or 3) and R is hydrogen, carboxyl, or aromatic; E is N,

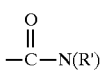

where R' is hydrogen or methyl, or S; and Y is a hydroxyalkyl phosphine of the formula P(A—OH)$_n$ where (n=1, 2, or 3) and where A is —CH$_2$, —C$_2$H$_4$, or iso- or normal- C$_3$H$_6$— and detecting for presence of the compound.

2. A method as set forth in claim 1, wherein said metal is a metallic isotope selected form the group including γ and β emitting isotopes, said compound being stable in aqueous solutions containing oxygen, serum and other body fluids.

3. A method as set forth in claim 2, wherein said metallic isotope is a radionuclide selected from the group including $^{186}$Re, $^{188}$Re, and $^{99m}$Tc, said compound being stable in aqueous solutions containing oxygen, serum and other body fluids.

4. A method as set forth in claim 1, wherein the compound includes a biomolecule attached to the complex.

5. A method as set forth in claim 4, wherein the biomolecule is a peptide.

6. A method as set forth in claim 5, including the step of covalently binding the peptide to the complex through at least one —NH$_2$ group present in the peptide involving formation of an amide bond by reacting an activated carboxyl group in the ligand with the peptide amino group.

7. A method of making a multi-dentate ligand-metal complex, said method including the following reactions:

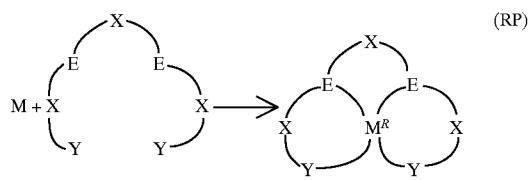

wherein, M is a transition metal, $M^R$ is a transition metal in a reduced state; X is (CHR)$_n$ where (n=0, 1, 2, or 3) and R is hydrogen, carboxyl, or aromatic; E is N,

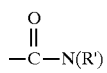

where R' is hydrogen or methyl, or S; and Y is a hydroxyalkyl phosphine of the formula P(A—OH)$_n$ where (n=1, 2, or 3) and where A is —CH$_2$, —C$_2$H$_4$, or iso- or normal —C$_3$H$_6$—.

8. A method as set forth in claim 7, wherein the transition metal is a metallic isotope selected from the group including γ and β emitting isotopes.

9. A method as set forth in claim 7, wherein the metallic isotope is a radionuclide selected from the group including $^{186}$Re, $^{188}$Re, and $^{99m}$Tc.

10. A method as set forth in claim 7 further including the step of attaching a biomolecule to the complex.

11. A method as set forth in claim 10, wherein the biomolecule is a peptide.

12. A method as set forth in claim 7 including the step of covalently binding the peptide to the complex through at least one —NH$_2$ group present in the peptide involving formation of an amide bond by reacting an activated carboxyl group in the ligand with the peptide amino group.

13. A method as set forth in claim 7 further including the step of attaching a protein or antibody to the complex.

14. A method as set forth in claim 7 further including the step of reacting uncoordinated hydroxyalkyl phosphine groups with an amine to remove the uncoordinated groups thereby yielding substantially pure compounds.

15. A method as set forth in claim 14 wherein the amine groups are affixed to a solid support.

16. A method as set forth in claim 15 wherein the solid support includes a separation column.

17. A method as set forth in claim 16 wherein said reacting step is further defined as passing the reaction mixture through a column having free amine groups affixed thereon.

18. A multi-dentate ligand for use in constructing therapeutic and diagnostic radiopharmaceuticals, said ligand having the structure:

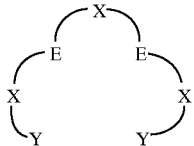

wherein X is $(CHR)_n$ where (n=0, 1, 2, or 3) and R is hydrogen, carboxyl, or aromatic; E is N,

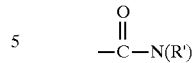

where R' is hydrogen or methyl, or S; and Y is a hydroxyalkyl phosphine of the formula $P(A—OH)_n$ where (n=1, 2, or 3) and where A is $—CH_2$, $—C_2H_4$, or iso- or normal $—C_3H_6—$.

19. A compound as set forth in claim 18 wherein A is $—CH_2$.

* * * * *